United States Patent [19]

Bradbury et al.

[11] Patent Number: 5,049,558
[45] Date of Patent: Sep. 17, 1991

[54] CEPHALOSPORIN DERIVATIVES

[75] Inventors: Robert H. Bradbury, Wilmslow, United Kingdom; Frederic H. Jung, Rilly La Montagne; Jean J. Lohmann, Hermonville, both of France; Peter R. Marsham, Poynton, United Kingdom; Georges Pasquet, Bazancourt, France

[73] Assignees: Imperial Chemical Industries PLC, London, England; ICI Pharma, Cergy Cedex, France

[21] Appl. No.: 409,290

[22] Filed: Sep. 19, 1989

Related U.S. Application Data

[63] Continuation of Ser. No. 738,646, May 28, 1985, abandoned.

[30] Foreign Application Priority Data

May 30, 1984 [EP] European Pat. Off. ............ 84401116

[51] Int. Cl.$^5$ .................. C07D 501/18; F61C 31/545
[52] U.S. Cl. .................................... 514/202; 514/201; 540/221; 540/222; 540/225
[58] Field of Search ................ 514/201, 202; 540/222, 540/221, 225

[56] References Cited

U.S. PATENT DOCUMENTS

| 4,489,072 | 12/1984 | Sadaki et al. | |
| 4,500,526 | 2/1989 | Imae et al. | 544/27 |
| 4,678,781 | 7/1987 | Jung | 514/200 |

FOREIGN PATENT DOCUMENTS

| 0018595 | 11/1980 | European Pat. Off. . |
| 0088853 | 9/1983 | European Pat. Off. . |
| 0127992 | 12/1984 | European Pat. Off. . |
| 0163190 | 12/1985 | European Pat. Off. . |
| 1155493 | 6/1969 | United Kingdom . |
| 2025398 | 1/1980 | United Kingdom . |
| 2036738 | 7/1980 | United Kingdom . |
| 2046261 | 11/1980 | United Kingdom . |
| 1604724 | 12/1981 | United Kingdom . |
| 2103205 | 2/1983 | United Kingdom . |

OTHER PUBLICATIONS

J. Med. Chem., 1975, 17, 1312–1315 (Nomura et al.).

Primary Examiner—Nicholas S. Rizzo
Attorney, Agent, or Firm—Cushman, Darby & Cushman

[57] ABSTRACT

A cephalosporin derivative of the formula I:

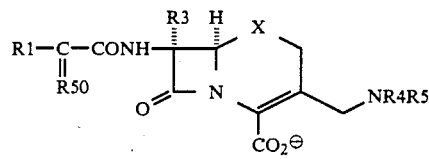

in which X is

S, O, CH$_2$ or SO, 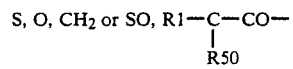

represents one of C-7 acyl groups known in the cephalosporin art, R3 is hydrogen or methoxy, R4 is hydrogen, optionally substituted alkyl or allyl, and R5 is an aromatic heterocyclic ring system which is linked via carbon, and which contains a quaternized nitrogen atom.

20 Claims, No Drawings

CEPHALOSPORIN DERIVATIVES

This is a continuation of application Ser. No. 06/738,646, filed May 28, 1985, which was abandoned upon the filing hereof.

This invention relates to cephalosporin derivatives which have antibacterial activity.

According to the invention there is provided a cephalosporin derivative of the formula I:

[Formula I—given hereafter]

in which X is sulphur, oxygen, methylene or sulphinyl (R or S configuration);

R1 is 2-aminothiazol-4-yl or 2-aminooxazol-4-yl each optionally substituted in the 5-position by fluorine, chlorine or bromine, or R1 is 5-aminoisothiazol-3-yl, 5-amino-1,2,4-thiadiazol-3-yl, 3-aminopyrazol-5-yl, 3-aminopyrazol-4-yl, 2-amino-pyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R50 is chloromethylene or a radical of the formula=N.0.R2, wherein R2 is hydrogen, (1–6C)alkyl, (3–8C)cyclo-alkyl, (1–3C)alkyl(3–6C)cycloalkyl, (3–6C)cycloalkyl(1–3C)alkyl, (3–6C)alkenyl, optionally substituted by carboxy, (5–8C)cycloalkenyl, (3–6C)alkynyl, (2–5C)alkylcarbamoyl, phenylcarbamoyl, benzylcarbamoyl, (1–4C)alkylcarbamoyl(1–4C)alkyl, di(1–4C)alkylcarbamoyl(1–4C)alkyl, (1–4C)haloalkyl-carbamoyl(1–4C)alkyl, triphenylmethyl, (1–3C)haloalkyl, (2–6C)hydroxyalkyl, (1–4C)alkoxy(2–4C-alkyl, (1–4C)alkylthio(2–4C)alkyl, (1–4C-alkanesulphinyl(1–4C)-alkyl, (1–4C)alkane-sulphonyl(1–4C)alkyl, (2–6C)aminoalkyl, (1–4C)alkyl-amino(1–6C)alkyl, (2–8C)dialkylamino(2–6-C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydro-furan-3-yl, or —R2 is the formula —(CH2)n—R6 in which n is 1 to 4 and R6 is piperidino, pyrrolidino, morpholino, piperazino or N-methylpiperazino, each value of R6 being optionally substituted by (1–4C)alkyl, phenyl or benzyl, or —R2 is of the formula —(CH2)m—W—R7 in which m is 0 to 3, W is sulphur or a direct bond, and R7 is phenyl or pyridinio(1–4C)alkylene or R7 is pyridyl, imidazolyl, 1,3,4-thiadiazolyl, tetrazolyl, 1-(1–4C)alkyltetrazolyl, thiazolyl, isothiazolyl or isoxazolyl in which the link with W is via a carbon or uncharged nitrogen, each value of R7 being optionally substituted, where possible, by one or two groups selected from (1–4C)alkyl, amino, hydroxy, carboxy, carbamoyl, nitro, (2–5C)alkoxycarbonyl, cyano or sulpho, or —R2 is of the formula —(CH2)n—CO—R8 in which n is 1 to 4 and R8 is (1–4C)alkyl, phenyl or benzyl, or —R2 is of the formula —COR9 or —(CH2)n—OCO—R9 in which n is 1-4 and R9 is hydrogen, (1–4C)alkyl, (1–4C)haloalkyl, phenyl or benzyl, or —R2 is of the formula —G—CH2-R10 in which G is carbonyl or a direct bond and R10 is phthalimido, or —R2 is of the formula —NR11R12R13 in which R11, R12 and R13 are (1–4C)alkyl, or R11 is (1–4C)alkyl and R12 and R13 are joined to form a (3–6C-)carbocyclic ring, or R11, R12 and R13 are joined to form a 1-azonia-4-azabicyclo[2,2,2]octane or 1-azonia-3,5,7-triazatricyclo[3,3,1,13,7]decane, or —R2 is of the formula II

[Formula II]

in which p is 1 or 2 and R14 and R15 are hydrogen or (1–4C)alkyl, or —R2 is of the formula —P(0)R16R17 in which R16 is hydroxy, (1–4C)alkoxy, (2–8C)dialkylamino, phenoxy, phenylamino or one of the values given above for R6, and R17 is (1–4C)alkyl, (1–4C)alkoxy (2–8C-)dialkylamino, phenoxy, phenylamino, piperidino, pyrrolidino, morpholino, piperazino or N-methylpiperazino, or —R2 is of the formula —CH2P(0)R18R19 in which R18 and R19 are hydroxy or (1–4C)alkoxy, or —R2 is of the formula —CH(SR20)COOR21 in which R20 is (1–4C)alkyl and R21 is hydrogen or (1–6C)alkyl, or —R2 is of the formula III:

[Formula III]

in which m is 0–3, R22 is hydrogen, (1–3C)alkyl or methylthio, R23 is hydrogen, (1–3C)-alkyl, (C3–C7)-cycloalkyl, cyano, carboxy, (2–5C)carboxyalkyl or methanesulphonylamino, or phenyl optionally substituted by amino or hydroxy, or R22 and R23 are joined to form, together with the carbon to which they are attached, a (3–7C) carbocyclic ring, and R24 is hydroxy, amino, (1–4C-alkoxy, (1–4C)alkylamino, phenylamino or of the formula R6 given above or of the formula NHOR25 in which R26 is hydrogen, (1–4C-alkyl, phenyl or benzyl, provided that when R2 contains phenyl, and unless otherwise stated, the phenyl is optionally substituted by 1 or 2 groups selected from halogen, hydroxy, amino, carboxy, nitro, carbamoyl, cyano and aminomethyl;

R3 is hydrogen or methoxy;

R4 is hydrogen, (1–4C)alkyl, halo(1–4C)alkyl, hydroxy(1–4C)alkyl, (1–4C)alkoxy(1–4C)alkyl, carboxy (1–4)alkyl, amino (1–4C)alkyl, cyano(1–4C)alkyl, (1–4C)alkanoylamino(1–4C)alkyl, allyl, furfuryl, benzyl or pyridyl(1–4C)alkyl;

R5 is an aromatic heterocyclic ring system which is linked via carbon and is one of the formula IV to LI inclusive each of these ring systems being optionally substituted where possible, on a carbon atom or atoms, by one, two or three substituents selected from halogen, (1–6C)alkyl, carboxy, (2–6C-)alkoxycarbonyl, (2–6C)- alkoxycarbonyl(1–4C)alkyl, (1–6C)alkoxy, (1–6C)alkylthio, cyano, (2–4C)cyanoalkyl, amino, (1–6C)alkylam , benzylamino (optionally substituted in the benzene ring thereof by nitro), thenylamino, allylamino, (1–6C)aminoalkylamino, (1–6C)alkoxy(1–6C)alkylamino, (1–6C)hydroxyalkylamino, hydroxy, mercapto, carbamoyl, (2–6C)alkylcarbamoyl, (3–10C)dialkylcarbamoyl, phenylthio and heteroarylthio wherein heteroaryl is a 5- or 6-membered ring containing 1, 2 or 3 hetero atoms selected from oxygen, nitrogen and sulphur;

and in which Y is oxygen, sulphur or NR27;

Z is nitrogen or CH;

one of A, B, D and E is +NR27 and the remainder are nitrogen;

and ring systems of Formula IV, XVI or XVII, which are optionally fused, on a carbon-carbon bond, with a 5- to 7-membered saturated carbocyclic ring;

R27 is nitrogen-linked and is (1–6C)alkyl, (1–6C)alkyl(-2–6C)alkenyl, (2–6C)alkenyl, (2–8C)alkoxyalkyl, carboxy(1–6C)alkyl, [(1–6C)alkoxy]carbonyl(1–6C)alkyl, carbamoyl(1–6C)alkyl, carboxyamino-carbonyl(-1–6C)alkyl, (1–6C)alkoxy]carbonylamino-carbonyl(1–6C)alkyl, (2–8C)alkanoyl]methyl, benzoylmethyl, (1-6C)hydroxyalkyl, (1-6C)alkylamino, or phenyl(1-6C)alkyl or phenyl, each optionally substituted by 1 or 2 groups selected from halogen, hydroxy, amino, carboxy, nitro, carbamoyl, cyano, trifluoromethyl, and aminomethyl;

R26 is hydrogen, (1-6C)alkyl, phenyl or benzyl;

R28 is cyano(3-6C)cycloalkenyl, or phenyl optionally substituted by 1 or 2 groups selected from halogen, nitro, amino, (1-4C-)alkanoyl, (1-4C-)alkanoylamino, halo(1-4C)alkyl, hydroxy, carboxy, (2-6C)alkoxycarbonyl, carbamoyl, mono- or di(1-4C)alkylcarbamoyl, cyano, mesyl, vinyl, and sulpho; or R28 is (2-6C)alkenyl, optionally substituted by halogen, cyano, carbamoyl, mono- or di(1-4C- alkyl)carbamoyl, piperidinocarbonyl or morpholinocarbonyl, cyano(1-4C)alkyl, 2-ureidoethyl, 2-thioureidoethyl, 2-(thioacetyl-amino)ethyl, sulphamoyl, 2-amino-2-carboxyethyl, acetylaminomethyl, phthalimidomethyl, 4,5-dihydroimidazol-2-ylmethyl, 3,4,5,6-tetrahydropyrimidin-2-ylmethyl, 2-(1,2,3,6-tetrahydro-2,6-dioxopurin-7-yl)ethyl, 2-hydroxy-iminopropyl (syn or anti) or 2-[(1-4C)alkoxyimino]-propyl (syn or anti), or —R28 is of the formula —(CH$_2$)$_2$-NR29R30R31 in which R29, R30 and R31 are (1-4C-alkyl, or —R28 is of the formula —(CH$_2$)$_q$—R32 in which q is 0-2 and —R32 is pyridine, pyridazine, pyrimidine, pyrazine, 1,2,5,6-dihydro-5,6-dioxo-1,2,4-triazine, 2-[(1-4C)alkyl]-1,2,5,6-dihydro-5,6-dioxo-1,2,4-triazine, 1-[(1-4C)-alkyl]tetrazole, furan, thiophene, pyrrole, 1-[(1-4C)-alkyl]pyrrole, oxazole, thiazole, imidazole, 1-[(1-4C-)alkyl]imidazole, isoxazole, isothiazole, pyrazole, 1,2,3-thiadiazole, 1-[(1-4C-)alkyl]pyrazole, benzfuran, benzthiophene, indole, oxindole, 1-[(1-4C)-alkyl]indole, benzoxazole, benzthiazole, benzimidazole, 1-[(1-4C)alkyl]-benzimidazole, 3,4-dihydro-4-oxo-2H-benzo[e]oxazine each of these ring systems being linked to (CH$_2$)$_q$ through carbon and each ring system being optionally substituted by halogen, amino, (1-6C)alkyl, (1-4C)-haloalkyl, (3-6C)cycloalkyl, (2-6C)alkenyl, carboxy, (2-6C)alkoxycarbonyl, (1-6C)alkoxy, cyano, (2-6C)cyanoalkenyl, carbamoyl, mono- or di (1-4C)alkylcarbamoyl, (1-4C)alkanoylamino, guanidino, hydroxy, nitro, amino; and for those ring systems which contain nitrogen, the N-oxides thereof where chemically possible;

or, when R4 is hydrogen then R5 is also a radical of the formula LI:

[Formula LI]

in which R28 is 2-guanidino-thiazol-4-ylmethyl, hydroxybenzoyl-methyl, 2-thenyl, 2-imidazolylmethyl or cinnamyl, optionally substituted by halogen, (1-6C)alkyl, hydroxy, (1-4C)alkoxy, carboxy, (2-6C)alkoxycarbonyl, nitro or carbamoyl, and when R4 is other than hydrogen then R5 is also a radical of the formula LII in which ring J is pyridine, pyrimidine, oxazole, thiazole, isoxazole, isothiazole or imidazole to each of which is optionally fused, when possible, a benzene, cyclopentane or cyclohexane ring; R33 is hydrogen, amino, (1-6C)alkyl, (3-6C)cycloalkyl, (3-6C)alkenyl, (2-8C)alkoxyalkyl, —(CH$_2$)$_t$—COOR35, —(CH$_2$)$_t$'CONH$_2$, —(CH$_2$)$_t$—NHCO—R36 or —(CH$_2$)$_t$S(O)$_s$—R36 in which t is 1-6, R35 is hydrogen or (1-6C)alkyl, s is 0, 1 or 2, and R36 is (1-6C)alkyl or (1-6C)alkoxy, or R33 is (3-8C)al-kanoylmethyl, benzoylmethyl, (1-6C)primaryhydroxyalkyl, (1-6C)primaryaminoalkyl, (1-4C)-alkylamino(1-6C-)alkyl, di(1-4C)alkylamino(1-6C)alkyl, carbamoyl(1-4C-)alkyl, mono- or di(1-4C)alkylcarbamoyl(1-4C-)alkyl, (1-4C-)alkoxy(1-4C)alkyl, (1-6C)alkoxy, (1-4C)alkoxy(2-4C-)alkoxy(1-4C)alkyl, (1-6C)alkylamino, phenyl(-1-6C)-alkyl or phenyl(1-6C)alkoxy or of the formula (CH$_2$)$_2$N=CR37NR38R39 or (CH$_2$)$_n$C(NR37)NR38R39 or a tautomer thereof in which R37, R38 and R39 are hydrogen or (1-4C)alkyl;

R34 is hydrogen or one or two substituents selected from halogen, amino, nitro, (1-6C)alkyl, carboxy, (2-6C)alkoxycarbonyl, (1-6C)alkoxy, cyano, carbamoyl, (1-6C)haloalkyl, (1-6C)azidoalkyl, (1-6C)aminoalkyl, (2-4C)aminoalkylthio(1-4C)alkyl, (2-6C)alkanoylamino, (2-4C)alkanoylamino(1-4-C)alkyl, (2-6C) alkanoyloxy(1-4C)alkyl, benzyl, benzyloxy and heteroarylthio, wherein, when R33 contains phenyl, the phenyl is optionally substituted by halogen, nitro, (1-6C)alkyl, hydroxy, (1-4C)alkoxy, carboxy, (2-6C)alkoxycarbonyl, carbamoyl, sulphamoyl, sulpho, mono- or di(1-4C)alkylcarbamoyl, or mono- or di-(1-4C)alkylsulphamoyl, and wherein when R34 is heteroarylthio, the heteroaryl ring is a 5- or 6-membered ring containing 1,2 or 3 hetero atoms selected from oxygen, nitrogen and sulphur;

and the salts formed with acids and bases which afford pharmaceutically acceptable anions and cations respectively.

It is to be understood that in the above formula I and throughout this specification, the illustrated stereochemistry of the ceph-3-em nucleus, and its optional modifications at the 1-position, is the absolute configuration. It is also to be understood that, since R5 contains a quaternary nitrogen, the compounds of the formula I will normally exist in zwitter-ionic form, involving the quaternary nitrogen and the carboxy group. When the compound of the formula I contains further acidic or basic substituents, it is to be understood that the possibility of a double zwitter-ionic form of the compound will arise. Alternatively, exogenous anions or cations may be included, to form pharmaceutically-acceptable base-addition or acid-addition salts, as defined above.

A particular value for R2 is hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, triphenylmethyl, 2-chloroethyl, 2-fluoroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)ethyl, tetrahydropyran-2-yl, thietan-3-yl or 2-oxo-tetrahydrofuran-3-yl, or, when R2 is of the formula —(CH$_2$)$_n$—R6 in which n is 1 to 4 and R6 is piperidino, pyrrolidino, morpholino, piperazino or N-methylpiperazino, a particular value of R2 is when each value of R6 is optionally substituted by methyl, phenyl or benzyl, or, when R2 is of the formula —(CH$_2$)$_m$—W—R7 in which m is 0 to 3, W is sulphur or a direct bond, particular values for R2 are when R7 is phenyl, pyridiniomethylene, 2-pyridinioethylene or R7 is pyridyl, imidazolyl, 1,3,4-thiadiazolyl, tetrazolyl, 1-methyltetrazolyl, thiazolyl, isothiazolyl or isoxazolyl in which the link with W is via a carbon or uncharged nitrogen, each value of R7 being optionally substituted, where possible, by one or two groups selected from methyl, amino, hydroxy, carboxy, carbamoyl, nitro, methoxycarbonyl, ethoxycarbonyl, cyano or sulpho, or, when R2 is of the formula —(CH$_2$)$_n$—CO—R8 in which n is 1 to 4, a particular value for R2 is when R8 is methyl, ethyl, phenyl or benzyl, or, when R2 is of the formula —COR9 or —(CH—2)—$_n$—OCO-R9 in which n is 1-4, a particular value for R2 is when R9 is hydrogen, methyl, chloromethyl, bromomethyl, 2-chloroethyl, 2-bromoethyl, phenyl or benzyl, or, when R2 is of the formula —G—CH$_2$—R10, a particular value for R2 is when G is carbonyl or a direct bond and R10 is phthalimido, or, when R2 is of the formula —NR11R12R13, a particular value for R2 is when R11, R12 and R13 are methyl or ethyl, or R11 is methyl or ethyl and R12 and R13 are joined to form a cyclopropyl, cyclobutyl, cyclopentyl or cyclohexyl ring, or R11, R12 and R13 are joined to form a 1-azonia-4-azabicyclo-[2,2,2]octane or 1-azonia-3,5,7-triazatricyclo-[3,3,1,1$^{3,7}$]decane, or, when R2 is of the formula II:
[Formula II ]
in which p is 1 or 2, a particular value for R2 is when and R14 and R15 are hydrogen or methyl, or when R2 is of the formula—P(O)R16R17, a particular value for R2 is when R16 is hydroxy, methoxy, ethoxy, dimethylamino, diethylamino, phenoxy, phenylamino, or one of the particular values given above for R6, and R17 is methyl, ethyl, methoxy, ethoxy, dimethylamino, diethylamino, phenoxy, phenylamino, piperidino, pyrrolidino, morpholino, piperazino or N-methylpiperazino, or, when R2 is of the formula —CH$_2$P(O)R18R19, a particular value for R2 is when R18 and R19 are hydroxy, methoxy or ethoxy, or, when R2 is of the formula —CH(SR20)COOR21, a particular value for R2 is when R20 is methyl or ethyl and R21 is hydrogen, methyl, ethyl or isopropyl, or, when R2 is of the formula III:
[Formula III]
in which m is 0-3, a particular value for R2, when m=0, is when R22 is hydrogen, methyl or methylthio, R23 is hydrogen, methyl, cyclopropyl, cyclobutyl, cyclopentyl, cyclohexyl, cyano, carboxy, carboxymethyl, 2-carboxyethyl or methanesulphonylamino, or phenyl optionally substituted by amino or hydroxy, or R23 and R24 are joined to form, together with the carbon to which they are attached, a cyclopropane, cyclobutane, cyclopentane, cyclohexane or cycloheptane ring and R25 is hydroxy, amino, methoxy, ethoxy, methylamino, ethylamino, phenylamino or one of the particular values for R6 given above or of the formula NHOR25 in which R25 is hydrogen, methyl, ethyl, phenyl or benzyl, provided that when R2 contains phenyl, and unless otherwise stated above, the phenyl is optionally substituted by 1 or 2 groups selected from fluorine, chlorine, bromine, hydroxy, amino, carboxy, nitro, carbamoyl, cyano and aminomethyl.

A particular value for R3 is hydrogen or methoxy.

A particular value for R4 is hydrogen, methyl, ethyl, n-propyl, isopropyl, 2-fluoroethyl, 2-chloroethyl, 2-hydroxymethyl, 2-methoxyethyl, carboxymethyl, (R) and (S)-1-carboxyethyl, 2-aminoethyl, 2-cyanoethyl, 2-formamidoethyl, allyl, furfuryl, benzyl or 4-pyridylmethyl.

A particular value for an optional substituent on one of the ring systems of the formula IV to LI inclusive is one, two or three substituents selected from fluorine, chlorine, bromine, methyl, ethyl, n-propyl, isopropyl, carboxy, methoxycarbonyl, ethoxycarbonyl, methoxycarbonylmethyl, ethoxycarbonylmethyl, methoxy, ethoxy, methylthio, ethylthio, cyano, cyanomethyl, 2-cyanoethyl, amino, methylamino, ethylamino, isopropylamino, dimethylamino, benzylamino, (optionally substituted in the benzene ring by nitro), allylamino, 2-aminoethyl-amino, 2-methoxyethylamino, 2-hydroxyethylamino, hydroxy, mercapto, carbamoyl, methylcarbamoyl, ethylcarbamoyl, dimethylcarbamoyl, phenylthio and heteroarylthio in which the heteroaryl ring is a furan, thiophene, imidazole, thiazole, pyrazole, thiadiazole, pyridine, pyrimidine, pyrazine or pyridazine.

A particular value for R27 is methyl, ethyl, n-propyl, isopropyl, allyl, methoxymethyl, 2-methoxyethyl, carboxymethyl, 2-carboxyethyl, methoxycarbonylmethyl, 2-methoxycarbonylethyl, carbamoylmethyl, 2-carbamoylethyl, carboxyaminocarbonylmethyl, 2-(carboxyaminocarbonyl)ethyl, methoxycarbonylaminocarbonylmethyl, 2-(methoxycarbonylaminocarbonyl)ethyl, acetylmethyl, propionylmethyl, benzoylmethyl, hydroxymethyl, 2-hydroxyethyl, methylamino, ethylamino, benzyl or 2-phenethyl, or phenyl optionally substituted by 1 or 2 groups selected from fluorine, chlorine, bromine, hydroxy, amino, carboxy, nitro, carbamoyl, cyano, trifluoromethyl and aminomethyl.

A particular value for R26 is hydrogen, methyl, ethyl, n-propyl, isopropyl, phenyl or benzyl.

A particular value for R28 is 3-cyano-cyclopent-2-enyl or phenyl optionally substituted by 1 or 2 groups selected from fluorine, chlorine, bromine, nitro, amino, acetyl, acetamido, trifluoromethyl, hydroxy, carboxy, methoxycarbonyl, ethoxycarbonyl, carbamoyl, methylcarbamoyl, dimethylcarbamoyl, diethyl-carbamoyl, cyano, mesyl and sulpho, or vinyl, 2,4-pentadienyl, 3-chloroallyl (cis and trans), 3-cyanoallyl, cyanomethyl, 3-cyanopropyl, 2-ureidoethyl, 2-thioureidoethyl, 2-(thioacetylamino)ethyl, sulphamoyl, 2-amino-2-carboxyethyl, acetylaminomethyl, phthalimidomethyl, 4,5-dihydroimidazol-2-ylmethyl, 3,4,5,6-tetrahydropyrimidin-2-ylmethyl, 2-(1,2,3,6-tetrahydro-2,6-dioxopurin-7-yl)ethyl, 2-hydroxyiminopropyl (syn or anti), 2-(methoxyimino)propyl (syn or anti) or 2-(ethoxyimino)propyl or anti), or of the formula —(CH$_2$)$_2$—NR29R30R31 in which R29, R30 and R31 are methyl or ethyl, or of the formula —(CH$_2$)$_q$—R32 in which q is 0–2 and R32 is pyridine, pyridazine, pyrimidine, pyrazine, 1,2,5,6-dihydro-5,6-dioxo-1,2,4-triazine, 2-(methyl or ethyl)-1,2,5,6-dihydro-5,6-dioxo-1,2,4-triazine, 1-(methyl or ethyl)tetrazole, furan, thiophene, pyrrole, 1-(methyl or ethyl)pyrrole, oxazole, thiazole, imidazole, 1-(methyl or ethyl)imidazole, isoxazole, isothiazole, pyrazole, 1-(methyl or ethyl) pyrazole, 1,2,3-thiadiazole, benzfuran, benzthiophene, indole, 1-(methyl or ethyl)indole, benzoxazole, benzthiazole, benzimidazole, 3,4-dihydro-4-oxo-2H-benzo[e]oxazine, 1-(methyl or ethyl)benzimidazole, each of these ring systems being linked to $(CH_2)_q$ through carbon and each ring system being optionally substituted by fluorine, chlorine, bromine, methyl, ethyl, n-propyl, isopropyl, trifluoromethyl, cyclopropylmethyl, formamido, carboxy, methoxycarbonyl, ethoxycarbonyl, methoxy, ethoxy, cyano, 3-cyanoallyl, carbamoyl, methylcarbamoyl, dimethylcarbamoyl, hydroxy, guanidino, nitro, amino and for those ring systems which contain nitrogen, the N-oxides thereof where chemically possible;

or, when R4 is hydrogen -R28 is 2-guanidino-thiazol-4-ylmethyl, 3-hydroxybenzoylmethyl, 2-thenyl, 2-imidazolylmethyl or cinnamyl, optionally substituted by fluorine, chlorine, bromine, methyl, ethyl, n-propyl, isopropyl, hydroxy, methoxy, ethoxy, carboxy, methoxycarbonyl, ethoxycarbonyl or carbamoyl;

and when R4 is other than hydrogen, a further particular value for R5 is of the formula LI:

8 Formula LII]

in which ring J is pyridine, pyrimidine, oxazole, thiazole, isoxazole, isothiazole or imidazole to each of which is optionally fused, when possible, a benzene, cyclopentane or cyclohexane ring.

A particular value for R33 is hydrogen, amino, methyl, ethyl, n-propyl, isopropyl, t-butyl, cyclopropyl, cyclobutyl, allyl, 3-chloroallyl (cis or trans) methoxymethyl, $-(CH_2)_t-COOR35$, $(CH_2)_t-CONH_2$, $(CH_2)_t-NH-CO-R36$ or $-(CH_2)_tS(O)_s-R36$ in which t is 1-6, R35 is hydrogen, methyl or ethyl, s is 0, 1 or 2 and R36 is methyl, ethyl, methoxy or ethoxy, or acetylmethyl, propionylmethyl, benzoylmethyl, hydroxymethyl, 2-hydroxyethyl, aminomethyl, 2-aminoethyl, 2-methylaminoethyl, 2-dimethylaminoethyl, carbamoylmethyl, methylcarbamoylmethyl, dimethylcarbamoylmethyl, 2-methoxymethyl, methoxy, ethoxy, 2-methoxyethoxymethyl, methylamino, ethylamino, benzyl, 2-phenethyl, 2-(3,4-dihydroxy-4-oxo-H-benzo[e]-oxazin-2-yl)ethyl, benzyloxy or 2-phenyloxy or of the formula $(CH_2)_2-N=CR37NR38R39$ or $(CH_2)_2C(N37)NR38R39$ in which R37, R33 and R39 are hydrogen or methyl, wherein when R33 contains phenyl the phenyl is optionally subtituted by fluorine, chlorine, bromine, methyl, ethyl, hydroxy, methoxy, ethoxy, carboxy, methoxycarbonyl, ethoxycarbonyl, sulpho, carbamoyl, methylcarbamoyl or dimethylcarbamoyl.

A particular value for R34 is hydrogen or one or two substituents selected from fluorine, chlorine, bromine, amino, nitro, methyl, ethyl, carboxy, methoxycarbonyl, ethoxycarbonyl, methoxy, ethoxy, cyano, carbamoyl, 2-chloromethyl, 2-chloroethyl, azidomethyl, aminomethyl, 2-aminoethyl, 2-aminoethylthiomethyl, acetylamino, propionylamino, acetylaminomethyl, acetoxymethyl, benzyl, benzyloxy, 2-thenylamino or heteroarylthio and in which when R34 is heteroarylthio the heteroaryl ring is furan, thiophene, pyrrole, imidazole, thiazole, isothiazole, oxazole, isoxazole, pyrazole, thiadiazole, pyridine, A particular acid which affords a pharmaceutically-acceptable anion is, for example, hydrochloric, hydrobromic, phosphoric, sulphuric, citric or maleic acid.

A particular base which affords a pharmaceutically acceptable cation is, for example, a base containing an alkali metal, (e.g. sodium or potassium) or an alkaline earth metal (e.g. calcium or magnesium), or a primary, secondary or tertiary organic amine (e.g. triethylamine, morpholine, N-methylpiperidine, N-ethylpiperidine, procaine, dibenzylamine or N,N'-dibenzylethylenediamine), or other amine which has been used to form salts with cephalosporins.

The following are preferred features of the cephalosporin derivative of the invention. When any one of these features is taken, either singly or in combination, with the other general or particular features of the cephalosporin derivative of the invention listed above, there are obtained preferred sub-groups of compounds.

1. X is sulphur.
2. R1 is 2-aminothiazol-4-yl or 5-amino-1,2,4-thiadiazol-3-yl.
3. R50 is chloromethylene.
4. R50 is =N.OR2 in which R2 is (1-6C)alkyl, (3-6C)alkenyl optionally substituted by carboxy, (3-6C)alkynyl, (3-8C)cycloalkyl, (3-6C)cycloalkyl(1-3C)alkyl, (1-4C)haloalkyl, (1-5C)cyanoalkyl, (2-6C)hydroxyalkyl, (1-4C)alkoxy((2-4C)alkyl, (2-6C)aminoalkyl or benzyl.
5. R2 is methyl, ethyl, i-propyl, allyl, propargyl, cyclopentyl, cyclopropylmethyl, 2-chloroethyl, 2-fluoroethyl, 2-bromoethyl, cyanomethyl, 2-cyanoethyl, 2-hydroxyethyl, 2-ethoxyethyl or benzyl.
6. R2 is of the formula III.
7. In formula III, m is 0.
8. In formula III, R24 is hydroxy or (1-4C)alkoxy.
9. In formula III, R22 and R23 are both hydrogen or (1-3C)alkyl, or R22 and R23 are joined to form, together with the carbon to which they are attached, a (3-7C) carbocyclic ring.
10. In formula III, R22 and R23 are both hydrogen or methyl, or R22 and R23 are joined to form, together with the carbon to which they are attached, a cyclobutane or cyclopentane ring.
11. R5 is of the formula XVI, XXVIII, XLII, XLIII, XLVI, XLVII or LI, each of these ring systems being optionally substituted, where possible, on a carbon atom or atoms, by one or two substituents selected from halogen, (1-6C)alkyl, carboxy, (2-6C-)alkoxycarbonyl(1-4C)alkyl, (1-6C)alkoxy, (1-6C)alkylthio, amino, (1-6C)alkylamino, (2-8C)dialkylamino, benzylamino, optionally substituted in the benzene ring thereof by nitro, allylamino, (1-6C)amino-alkylamino, (1-6C)-alkoxy(-1-6C)alkylamino, (1-6C)hydroxyalkylamino and hydroxy.
12. In formulae XVI, XXVIII, XLII, XLIII, XLVI and XLVII, the ring substituents are selected from chlorine, fluorine, methyl, ethyl, n-propyl, isopropyl, carboxy, methoxycarbonylmethyl, ethoxycarbonylmethyl, methoxy, ethoxy, methylthio, amino, isopropylamino, dimethylamino, p-nitrobenzylamino, allyamino, 2-aminoethylamino, 2-methoxyethylamino, 2-hydroxyethylamino and hydroxy.
13. In formulae XVI, XXVIII and XLVII, R27 is (1-6C)alkyl, allyl or phenyl optionally substituted by nitro or trifluoromethyl.
14. In formulae XLII and LI, R28 is phenyl optionally substituted by 1 or 2 groups selected from halogen, nitro, amino, (1-4C)alkanoyl, (1-4C)alkanoylamino, (1-4C)haloalkyl, hydroxy, (2-6C)alkoxycarbonyl, carbamoyl, mono- or di(1-4C-)alkylcarbamoyl, cyano, mesyl and vinyl.
15. In formulae XLII and LI, the substituents in R28, when R28 is phenyl, are selected from chlorine, fluorine, nitro, amino, acetyl, acetamido, trifloromethyl, hydroxy, methoxycarbonyl, ethoxycarbonyl, carbamoyl, methylcarbamoyl, dimethylcarbamoyl, cyano, mesyl and vinyl.

16. In formulae XLII and LI, R28 is (2–6C)alkenyl, optionally substituted by halogen or cyano, cyano(1–4C)alkyl, phthalimidomethyl or 2-(1,2,3,6-tetrahydro-2,6-dioxopurin-7-yl)ethyl.

17. In formulae XLII and LI, R28 is vinyl, 2,4-pentadienyl, 3-cyanopropyl, 3-chloroallyl, 3-cyanoallyl, phthalimidomethyl or 2-(1,2,3,6-tetra-hydro-2,6-dioxopurin-7-yl)ethyl.

18. In formulae XLII and LI, R28 is of the formula $(CH_2)_q$—R32, wherein q is 0 or 1 and R32 is pyridine, pyridine-N-oxide, pyridazine, pyrazine, pyrazine-N-oxide, pyrimidine, furan, thiophene, thiazole, imidazole, 1,2,3-thiadiazole, oxazole, oxindole, benzimidazole or 3,4-dihydro-4-oxo-2Hbenzo[-oxazine, optionally substituted by halogen, amino, (1–6C)alkyl, (1–4C)haloalkyl, (3–6C)cycloalkyl, (2–6C)alkoxycarbonyl, cyano, (2–6C)cyanoalkenyl, carbamoyl, mono- or di(1–4C)alkylcarbamoyl, (1–4C)alkanoylamino, guanidino, hydroxy, nitro or amino.

19. The substituent in R32 is chlorine, fluorine, amino, methyl, ethyl, n-propyl, isopropyl, trifluoromethyl, cyclopropyl, methoxycarbonyl, ethoxycarbonyl, cyano, 3-cyanoallyl, carbamoyl, methylcarbamoyl, dimethylcarbamoyl, formamido, guanidino, hydroxy, nitro or amino.

20. In formula LII, R33 is (1–6C)alkyl and R34 is hydrogen.

21. R33 is methyl or ethyl.

22. R4 is hydrogen, (1–4C)alkyl, halo(1–4C)alkyl, hydroxy(1–4C)alkyl, (1–4C)alkoxy(1–4C)alkyl, carboxy(1–4C)alkyl, amino(1–4C)alkyl, cyano(1–4C)alkyl, (1–4C)alkanoylamino(1–4C)alkyl, allyl, furfuryl, benzyl or pyridyl (1–4C)alkyl.

23. R4 is hydrogen, methyl, ethyl, 2-fluoroethyl, 2-chloroethyl, 2-hydroxyethyl, 2-methoxyethyl, carboxymethyl, 2-aminoethyl, 2-methoxyethyl, 2-formamidoethyl, allyl, furfuryl, benzyl or 4-pyridylmethyl.

24. R5 is of the formula XVI, XXVIII, XLII, XLIII, XLVI, LI or LII.

25. R5 is of the formula XVI wherein the ring is substituted by (1–6C)alkyl and/or amino.

26. R5 is of the formula XXVIII wherein Y is sulphur, Z is CH and R27 is (1–6C)alkyl, particularly methyl.

27. R5 is of the formula XLII wherein R28 is (2–6C)alkenyl, optionally substituted by cyano or halogen, particularly chlorine, or R28 is $(CH_2)_q$R32 in which q is 1 and R32 is 1,2,3-thiadiazole, thiophen or thiazole optionally substituted by guanidino or cyano.

28. R5 is of the formula XLIII wherein Y is sulphur.

29. R5 is of the formula XLVI wherein the optional bond is a double bond.

30. R5 of the formula LI wherein R28 is $(CH_2)_q$R32 in which q is 1 and R32 is thiophen.

31. R5 is of the formula LII wherein ring J is pyridine, R33 is amino, (1–6C)alkyl, (1–6C)primary-aminoalkyl, or benzyl optionally substituted by nitro, and R34 is hydrogen or (1–6c)alkyl.

Particular compounds of the invention are described in the Examples, and of these, the group consisting compounds of Examples 37, 55, 60, 64, 66, 71, 81, 87, 88, 95, 96, 104, 110, 111, 149, 150, 151, 153, 177, 178, 184, 185, 188, 195, 202, 209, 213, 215, 218, 219, 225, 226, 232, 244, 249, 251, 255, and 261 is preferred. A more preferred group consists of the compounds of Examples 37, 55, 60, 64, 66, 71, 88, 96, 104, 110, 149, 150, 153, 178, 184, 213, 219, 225, 244, 249, 255, and 261. Within this group, the compounds of Examples 60, 66, 104, 110, 184, 188, 219, 225, 255 and 261 are particularly preferred, and of these the compounds of Examples 110, 184, 219 and 225 are especially preferred.

The cephalosporin derivatives of the formula I may be manufactured by methods known in themselves for the manufacture of chemically analogous compounds. The for following processes, R1, R2, R3, R4, R5, R50 and X having the meanings stated above, unless indicated otherwise, and therefore provided as further features of the invention.

The process of the invention is characterised by (a) reaction of a compound of the formula LIII
[Formula LIII]
with a compound of the formula R5–R40 in which R40 is a displaceable radical [e.g. fluorine, chlorine, bromine, (1–6C)alkoxy, (1–6C)alkylthio, (1–6C)alkanesulphinyl or (1–6C)alkanesulphonyl].

(b) reaction of a compound of the formula LIV:
[Formula LIV]
with an acid of the formula LV:
[Formula LV]
or an activated derivative thereof.

(c) deprotection, to form carboxy, of the corresponding compound which carries a protecting group in place of the acidic hydrogen atom of the carboxy (d) deprotection, to form a primary or secondary amino, of the corresponding compound which carries a protecting group in place of the amino hydrogen.

(e) for those compounds in which X is sulphinyl, oxidation of the corresponding compound in which X is sulphur.

(f) reaction of a compound of the formula LVI
[Formula LVI]
with a compound of the formula R2—O—NH2.

(g) for those compounds in which R2 is other than hydrogen, reaction of a compound of the formula I in which R2 is hydrogen with a compound of the formula R41—R40 in which R40 is a displaceable radical and R41 is one of the values given above for R2, other than hydrogen.

(h) for those compounds which contain an aminophenyl group, the reduction of the corresponding nitrophenyl compound.

(i) the reaction of a compound of the formula LVIII, wherein R40 is a displaceable radical, with a compound of the formula R4R5NH.

When the process of the invention manufacture the compound of the formula I in the form of the zwitterion, and a salt is required, the compound of the formula I in the zwitterionic form is reacted with an acid which affords a -pharmaceutically-acceptable anion, or with a base which affords a pharmaceutically-acceptable cation.

The starting material of the formula LIII may be prepared by acylation of the appropriate 7-amino-3-azidomethylcephalosporin derivative with an acid of the formula LV, or an activated derivative thereof, followed by reduction of the 3-azidomethyl group to the 3-aminomethyl group. During this process it may be necessary to protect amino and carboxy groups. There is thus obtained the compound of the formula LIII in which R4 is hydrogen. This procedure is illustrated in Examples 1–4, 5–6, 7–14 and 15–16.

When R4 is other than hydrogen, the compound in which R4 is hydrogen is then alkylated or benzylated.

The starting material of the formula LIV may be prepared by reaction of the compound of the formula LVIII:

[Formula LVIII]

with a compound of the formula R5—R40 in which R40 is a displaceable radical. During this reaction it may be necessary to protect the 7-amino and/or 3-carboxy group.

The starting material of the formula LIV in particularly valuable and is regarded as a further feature of the invention.

The starting materials of the formulae LV, LVI, LVII and LVIII are prepared by conventional methods known in the chemical literature for analogous compounds.

As noted above the cephalosporin derivatives of the invention have antibacterial properties. Thus they are useful antibacterial agents, many of them having a broad spectrum of activity in vitro against standard laboratory microorganisms, both Gram-negative and Gram- positive, which are used to screen for activity against pathogenic bacteria. The antibacterial spectrum and potency of a particular compound may be determined in a standard test system.

The antibacterial properties of the compounds of the invention may also be demonstrated in conventional mouse protection tests, and the preferred compounds of this invention have $MIC_{50}$ values of less than $2/\mu g./ml.$ against both *Pseudomonas aeruginosa* and *Staphyllococcus aureus.*

Cephalosporin derivatives have generally been found to be relatively non-toxic to warm-blooded animals, and this generalisation holds true for the compounds of the present invention. A number of compounds were administered to mice at doses in excess of those required to afford protection against bacterial infections, and no overt toxic symptoms or side effects attributable to the administered compounds were noted.

According to a further feature of the invention there is provided a pharmaceutical composition which comprises a cephalosporin derivative of the invention in association with a pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other betalactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated, but not limited, by the following Examples. The n.m.r. spectra are quoted in delta relative to tetramethylsilane (delta=0) as internal standard, (s=singlet, d=doublet, t=triplet, q=quartet, m=multiplet, br=broad). The n.m.r. are measured at a field strength of 90 or 400 MHz. The n.m.r. solvents are as follows:

Solvent A: $d_6DMSO+CD_3COOD$
Solvent B: $d_6DMSO+CD_3COOD+TFA$
Solvent C: $CDCl_3+CD_3COOD$ The temperatures are in degrees Centigrade. The following contractions are used:

| | |
|---|---|
| TFA = | trifluoroacetic acid |
| THF = | tetrahydrofuran |
| HOAc = | acetic acid |
| EtOAc = | ethyl acetate |
| MeOH = | methanol |
| DMF = | dimethylformamide |
| DMSO = | dimethylsulphoxide |
| ether = | diethyl ether |
| HPLC = | high pressure liquid chromatography |
| Et$_3$N = | triethylamine |
| Lawesson's reagent = | 2,4-dithioxo-P$^5$,P$^5$-1,3,2,4-dithiaphosphatane. |
| MCBPA = | m-chloroperbenzoic acid. |
| DCCI = | N,N'dicyclohexylcarbodi-imide. |
| CAZAMCA = | 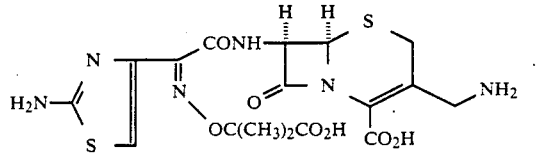 |
| BOC = | tert-butoxycarbonyl. |

EXAMPLES 1-4

To a solution of 3-aminomethyl-7-[2-(2-aminothiazol-4-yl)-2-[(Z-1-carboxy-1-methylethoxyimino)acetamido]ceph-3-em-4-carboxylic acid (0.4 mmole) in DMF (11 ml.) and water (3 ml.) at 0° was added sodium bicarbonate (4.8 mmole) dissolved in the minimum volume of water followed by the appropriate 4-chloroheterocycle (0.4 mmole). After 1 hour the mixture was treated with HOAC (4.8 mmole) and evaporated to dryness under reduced pressure. The residue was dissolved in water and purified by HPLC on an octadecylsilane column using MeOH/water/HOAC 40:60:1 v/v/v eluant. Using this general method the following compounds were thus obtained.

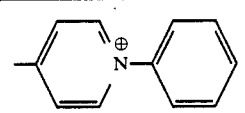

| Example | —R | Yield % | Footnotes |
|---|---|---|---|
| 1 | 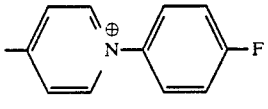 | 39 | 1, 2 |
| 2 | 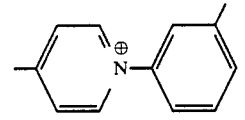 | 31 | 3, 4 |
| 3 | 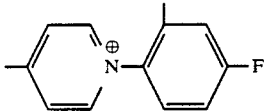 | 33 | 5, 6 |
| 4 | | 31 | 5, 7 |

Footnotes 1. The starting material was prepared by reaction of 1-phenyl-4-pyridone with toluene-p-sulphonylchloride in refluxing toluene to give 4-chloro-1-phenyl toluene-p-sulphonate. 2. n.m.r. in solvent A: 1.5 (s,6H); 3.35 (d,1H); 3.68 (d,1H); 4.3 (d,1H); 4.6 (d,1H); 5.12 (d,1H); 5.75 (d, 1H); 6.68 (s,1H); 7.1 (d,1H); 7.6 (m, 6H); 8.4 (d,1H); 8.5 (d,1H). 3. The starting material was prepared as follows. A mixture of 2,6-dicarboxy-4-pyrone (1.84 g.) and 4-fluoroaniline (1.9 ml.) was heated at 180° under argon until evolution of gas ceased. The cooled mixture was purified by chromatography on silica gel, eluting with $CH_2Cl_2$/MeOH 100-90:0-10 v/v to give, after sublimation (150°/0.01 mmHg 1-(4-fluorophenyl)-4-pyridone(1.24 g.). n.m.r. in $CDCl_3$:- 6.45 (d, 2H); 7.3 (m, 4H); 7.54 (d, 2H). Reaction of this compound with toluene-p-sulphonylchloride in refluxing toluene gave 4-chloro-1-(4-fluorophenyl)pyridinium toluene-p-sulphonate. 4. n.m.r. in solvent A: 1.4 (s, 6H); 3.35 (d,1H); 3.65 (d,1H); 4.25 (d,1H); 4.46 (d, 1H); 5.1 (d,1H); 5.8 (d,1H); 6.7 (s,1H); 6.9–7.8 (complex, 6H); 8.3 (d,1H); 8.5 (d,1H). 5. The starting material was prepared by the method described in Footnote 3, using the appropriate substituted aniline. 6. n.m.r. in solvent A: 1.4 (s,6H); 3.36 (d,1H); 3.64 (d,1H); 4.27 (d,1H); 4.48 (d,1H); 5.1 (d,1H); 5.8 (d,1H); 6.7 (s,1H); 6.9–7.7 (m,6H); 8.35 (d,1H); 8.5 (d,1H). 7. n.m.r. in solvent A: - 1.45 (s,6H); 3.4 (d,1H), 3.68 (d,1H); 4.3 (d,1H); 4.5 (d,1H); 5.12 (d,1H); 5.85 (d,1H); 6.75 (s,1H), 6.9–7.9 (m,5H); 8.2 (d,1H); 8.4 (d, 1H).

The cephalosporin starting material may be obtained as follows:

To a stirred mixture of DMF (5.80 ml.) in anhydrous methylene chloride (415 ml.) at −10° was added dropwise oxalyl chloride (6.15 ml.). Stirring was continued at −10° for 30 minutes to give a gelatinous white precipitate of (chloromethylene)-dimethylammonium chloride. To this stirred suspension was added powdered 2-((Z)-1-t-butoxycarbonyl-1-methyl-ethoxyimino)-2-(2-tritylaminothiazol-4-yl)acetic acid (40.0 g.) followed by N-methylmorpholine (8.8 ml.). Stirring was continued for 30 minutes between −5° and −15°.

In another flask a suspension of 7-amino-3-azidomethylceph-3-em-4-carboxylic acid (17.85 g.) in anhydrous methylene chloride (150 ml.) was stirred for 1 hour with N,O-bis(trimethylsilyl)acetamide (34.5 ml.) to give a clear orange solution. This was transferred by syringe to the above acid chloride solution which was stirred at −10° during the addition. The reaction mixture was then allowed to warm to room temperature and stirred for a further 90 minutes. The mixture was then poured into water (500 ml.) and extracted with EtOAc (3×500 ml.). The combined EtOAc extracts were washed with water, dried ($Na_2SO_4$) and the solvent was evaporated under reduced pressure to yield a buff foam. The crude product was dissolved in methylene chloride and applied to a column of Kieselgel 60 (125 g.). Elution with methylene chloride/MeOH/HOAc 96:2:2 v/v/v gave 3-azidomethyl-7-[2-(2-tritylaminothiazol-4-yl)-2-((Z)-1-t-butoxycarbonyl1-methylethoxyimino)-acetamido]-ceph-3-em-4-carboxylic acid (46.4 g.) as a white foam n.m.r. in solvent A: 1.30 (s, 9H); 1.35 (s,6H); 3.37 (d, 1H); 3.65 (d, 1H); 3.90 (d,1H); 4.35 (d,1H); 5.1 (d,1H); 5.7 (d,1H); 6.66 (s,1H); 7.25 (s,15H).

An aqueous slurry of Raney nickel (10.2 g.) was added in one portion to a stirred solution of the azide (20.0 g.) in a mixture of MeOH (60 ml.) and TFA (60 ml.) at room temperature. A vigorous effervescence was observed. Stirring was continued for 1 hour and the Raney nickel was removed by filtration through diatomaceous earth. The filter pad was washed well with MeOH and the washings were combined with the filtrate. The solvents were evaporated under reduced pressure to give a pale green solid residue which was then stirred for 2 hours with a mixture of TFA (60 ml.) and water (15ml.). This mixture was evaporated to dryness and the residue was stirred vigorously with water (400 ml.) for 30 minutes. The resulting solution was filtered through diatomaceous earth to remove the undissolved triphenylmethanol and the filtrate was applied to a column of Diaion HP 20 resin (1 l.). The column was eluted with water (500 ml.) to remove inorganic material and then with aqueous MeOH 1:1 v/v. The fractions which were shown by HPLC to contain the product were evaporated under reduced pressure to yield 3-aminomethyl-7-[2-(2-aminothiazol-4-yl)-2-((Z)-1-carboxy-1-methylethoxyimino)acetamido]ceph-3-em-4-carboxylic acid (4.2 g.) as a pale yellow foam having the following n.m.r. in solvent A: 1.4 (s,6H); 3.1–3.8 (complex, 4H); 4.95 (d,1H); 5.7(d,1H); 6.72 (s,1H).

EXAMPLES 5–6

The general process described in Examples 1–4 was repeated, and the following compounds were obtained.

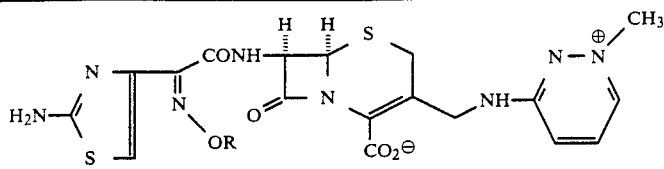

| Example No. | —R | Yield % | Footnotes |
|---|---|---|---|
| 5 | —C$_2$H$_5$ | 64 | 1, 2, 3 |
| 6 | ⟨cyclobutyl⟩—COOH | 55 | 4, 5 |

Footnotes 1. The starting material may be prepared as follows. Reaction of (Z)-2-ethoxyimino-2-(2-tritylaminotriazol-4-yl)acetic acid and 7-amino-3-azidomethyl-ceph-3-em-4-carboxylic acid (previously treated with N,O-bistrimethylsilylacetamide in the presence of chloromethyleneammonium chloride and N-methylmorpholine) in CH$_2$Cl$_2$/DMF gave after purification by chromatography on silica gel 3-azidomethyl-7-[(Z)-2-ethoxyimino-2-(2-tritylaminothiazol-4-yl)acetamido]ceph-3-em-4-carboxylic acid; n.m.r. in CDCl$_3$: 1.29 (t,3H); 3.3 (d,1H); 3.54 (d,1H); 3.87 (d,1H), 4.3 (q,2H); 4.38 (d,1H); 4.97 (d,1H); 5.73 (q,1H); 6.72 (s,1H); 7.26 (m,15H).

This 3-azidomethyl compound in TFA acid was reduced with Raney nickel to give, after purification by chromatography on a Diaion CHP20P column, 3-aminomethyl-7-[2-(2-aminothiazol-4-yl)-(Z)-2-ethoxyimino)acetamido]ceph-3-em-4-carboxylic acid; n.m.r. in solvent A: 1.2 (t,3H); 3.26 (d,1H); 3.48 (br s,2H); 3.68 (d,1H); 4.08 (q,2H); 4.97 (d,1H), 5.66 (d,1H); 6.69 (s,1H). 2. The quaternised starting material was 3-chloro-1-methylpyridazinium iodide. 3. n.m.r. in solvent A: 1.2 (t, 3H); 3.31 (d,1H); 3.61 (d,1H); 4.12 (q,2H); 4.23 (s,3H); 4.48 (d,1H); 4.99 (d,1H); 5.65 (d,1H); 6.69 (d,1H); 7.6 (m,1H); 7.9 (dd, 1H); 8.88 (d,1H). 4. n.m.r. in solvent A: 1.9 (m,2H); 2.45 (m,4H); 3.44 (d,1H); 3.66 (d,1H); 4.1 (d,1H); 4.28 (s,3H); 4.57 (d,1H); 5.1 (d,1H); 5.82 (d,1H); 6.83 (s,1H); 7.63 (br, 1H); 7.92 (br,1H); 8.9 (d,1H). 5.

The starting material was prepared from 2-[(Z)-1-(t-butoxycarbonyl)cyclobut-1-yloxyimino]-2-(2-tritylaminothiazol-4-yl)acetic acid by the general method described in Footnote 1. to give 3-azidomethyl-7-((Z)-2-[1-t-butoxycarbonyl)cyclobut-1-yloxyimino]-2-(2-tritylaminothiazol-4-yl)acetamido)ceph-3-em-4-carboxylic acid, having the following n.m.r. in solvent A: 1.38 (s,9H); 1.78 (m,1H); 1.89 (m,1H); 2.35 (m,4H); 3.45 (d,1H); 3.63 (d, 1H); 3.9 (d,1H); 4.38 (d,1H); 5.13 (d,1H); 5.76 (d,1H); 6.68 (s,1H); 7.18–7.37 (m,15H).

The above 3-azidomethylcephalosporin derivative was reduced by the general method described in Footnote 1 to give 3-aminomethyl-7-[2-(2-amino-thiazol-4-yl)-(Z)-2-(1-carboxycyclobut-1-yloxyimino)-acetamido]ceph-3-em-4-carboxylic acid, which was partially purified by chromatography on Diaion CHP20 resin before use without further characterisation.

EXAMPLES 7–14

The general process described in Examples 1–4 was repeated using the appropriate heterocyclic starting material. The reactions were carried out in DMF in the presence of triethylamine or DMF/water mixtures in the presence of NaHCO$_3$ at a temperature in the range ambient to 90° for 1–20 hours. The product was purified on an octadecylsilane column and the following compounds were thus prepared.

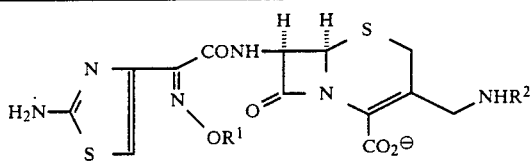

| Example | —R$^1$ | —R$^2$ | Yield % | Footnotes |
|---|---|---|---|---|
| 7. | —C(CH$_3$)$_2$COOH | 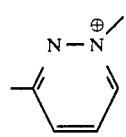 | 17 | 1, 2, 3 |
| 8. | —C(CH$_3$)$_2$COOH | 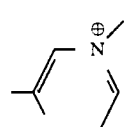 | 7 | 4, 2, 5 |

| | | -continued | | |
|---|---|---|---|---|

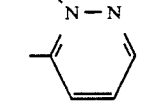

| | | | | |
|---|---|---|---|---|
| 9. | —C(CH₃)₂COOH | 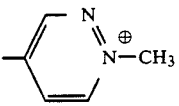 | 16 | 6, 7, 8 |
| 10. | C(CH₃)₂COOH | 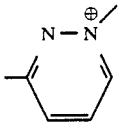 | 26 | 9, 2, 10 |

| Example | R¹ | —R | Yield % | Footnotes |
|---|---|---|---|---|
| 11 | —CH₃ | 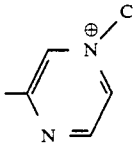 | 33 | 11, 12, 13 |
| 12 | —CH₃ | 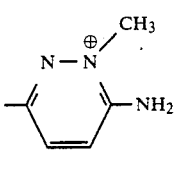 | 36 | 14, 15 |
| 13 | —C(CH₃)₂COOH | 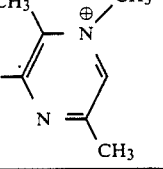 | 22 | 16, 17, 18 |
| 14 | —C(CH₃)₂COOH |  | 20 | 19, 17, 20 |

Footnotes 1. The starting material was prepared by reaction of 3-chloropyridazine with trimethyloxonium tetrafluoroborate in CH₂Cl₂ for 18 hours to give 3-chloro-1-methylpyridazinium tetrafluoroborate. 2. HPLC eluant MeOH/water/HOAc 20:79:1 v/v/v. 3. n.m.r. in solvent B: 1.53 (s,3H); 1.52 (s,3H); 3.56 (m,2H); 4.26 (s,3H); 4.1 (d,1H); 4.6 (d,1H); 5.17 (d,1H); 5.88 (d,1H); 6.94 (s,1H); 7.7 (d,1H); 7.98 (dd,1H); 8.95 (d,1H). 4. The starting material was prepared by reaction of 3-fluoropyrazine with trimethyloxonium tetrafluoroborate in CH₂Cl₂ for 4 hours under reflux to give 1-methyl-3-fluoropyrazinium tetrafluoroborate. 5. n.m.r. in solvent B: 1 53 (s,3H); 1.54 (s,3H); 3.55 (m,2H); 4.21 (s,3H); 4.2 (d,1H); 4.7 (d,1H); 5.15 (d,1H); 5.85 (d,1H); 7.0 (s,1H); 8.0 (d,1H); 8.19 (s,1H); 8.6 (d,1H). 6. The starting material was obtained as follows. Reaction of 3,6-dichloropyridazine with trimethyloxonium tetrafluoroborate gave 3,6-dichloro-1-methylpyridazinium tetrafluoroborate. To this compound (2.0 mmole) in acetonitrile was added NaHCO₃ (2.0 mmole), a few drops of triethylamine and 2-acetamido-1-mercaptoethane (2.4 mmole). After 1 hour at ambient temperature the mixture was filtered, the filtrate evaporated and ether and CH₂Cl₂ added. The product crystallized to give 3-chloro-1-methyl-6-(2-acetamidoethylthio)-pyridazinium tetrafluoroborate. 7. HPLC eluant MeOH/water/HOAc 23:76:1 v/v/v. 8. n.m.r. in solvent B: 1.53 (s,1H); 1.54 (s,1H); 3.6 (br s,2H); 3.99 (s,3H); 4.6 (d,1H); 4.8 (d,1H); 5.17 (d,1H); 5.9 (d,1H); 6.95 (s,1H); 8.16 (dd,2H). 9. The starting material was obtained by reaction of 4-methoxypyridazine with trimethyloxonium tetrafluoroborate in CH₂Cl₂ for 8 hours at ambient temperature to give 4-methoxy-1-methylpyridazinium tetrafluoroborate. 20. n.m.r. in solvent B: 1.53 (br s,6H); 4.1 (s,3H); 4.39 (m,2H); 5.19 (d,1H); 5.85 (d,1H); 7.0 (s,1H); 7.37 (dd,1H); 8.55 (d,1H); 8.9 (d,1H). 11. The 3-aminomethyl-7-[2-(2-aminothiazol-4-yl)-2-((Z)-methoxyimino)acetamido]-ceph3-em-4-carboxylic acid trifluoroacetate used as starting material may be prepared as follows:

To a solution of cefotaxime (5.24 g.) in phosphate buffer (pH 6.4, 440 ml.) was added sodium azide (2.86 g.) and sodium iodide (1.65 g.) and the mixture was immersed in a 70° bath with stirring for 4.5 hours. The solvent was evaporated to the point of precipitation and then the pH adjusted to 2.5 with 2N aqueous HCl. The resulting precipitate was collected, washed with water, acetone and ether and dried over $P_2O_5$ to give 3-azidomethyl-7-[2-(2-aminothiazol-4-yl)-2-((Z)-methoxyimino)acetamido]ceph-3-em-4-carboxylic acid in quantative yield, having the following n.m.r. in solvent A: 3.4 (d, 1H); 3.7 (d, 1H); 3.86 (s, 3H); 3.95 (d, 1H); 4.4 (d, 1H); 5.15 (d, 1H); 5.78 (d, 1H); 6.75 (s, 1H).

To a stirred suspension of Raney nickel (16 g.) in MeOH (13 ml.) at 0° was added a solution of 3-azidomethyl-7-[2-(2-aminothiazol-4-yl)-2-((Z)-methoxy-imino)acetamido]ceph-3-em-4-carboxylic acid (2.96 g.) in MeOH/TFA (14 ml., 1.13 ml.). After effervescence ceased the mixture was diluted with MeOH and filtered through paper. The filtrate was evaporated, the residue purified by HPLC using water/HOAc/-MeOH 79:1:20 v/v/v as eluant and the product dried over $P_2O_5$ to give 3-aminomethyl-7-[2-(2-aminothiazol-4-yl)-2-(Z)-methoxy-imino)acetamido]ceph-3-em-4-carboxylic acid trifluoroacetate (yield 45%) having the following n.m.r. in solvent A:- 3.5-4.2 (m, 4H); 3.9 (s, 3H); 5.15 (d, 1H); 5.85 (d, 1H); 6.75 (s, 1H). 12. HPLC eluant MeOH/water/HOAc 10:89:1 v/v/v. 13. n.m.r. in solvent B: 3.46 (d,1H), 3.72 (d,1H); 3.97 (s,3H); 4.25 (s,3H); 4.11 (d,1H); 4.63 (d,1H); 5.13 (d,1H); 5.73 (d,1H); 6.97 (s,1H); 7.57 (d,1H); 7.98 (dd,1H); 8.93 (d,1H). 14. HPLC eluant MeOH/water/HOAc 15:84:1 v/v/v. 15. n.m.r. in solvent B: 3.43 (d,1H); 3.69 (d,1H); 3.97 (s,3H); 4.19 (s,3H); 4.23 (d,1H); 4.66 (d,1H); 5.12 (d,1H); 5.69 (d,1H); 7.0 (s,1H); 7.98 (d,1H); 8.2 (s,1H); 8.6 (d,1H). 16. The starting material was prepared by reaction of 3,6-difluoropyridazine and trimethyloxonium tetrafluoroborate in $CH_2Cl_2$ for 15 hours at ambient temperature to give 3,6-difluoro-1-methyl-pyridazinium tetrafluoroborate. This compound in acetonitrile was treated with a solution of ammonia in chloroform in the presence of 1 equivalent of $NaHCO_3$ for 0.5 hours at ambient temperature to give 3-amino-6-fluoro-2-methyl pyridazinium tetrafluoroborate. 17. HPLC eluant MeOH/water/HOAc 25:74:1 v/v/v. 18. n.m.r. in solvent B: 1.53 (s,6H); 3.5 (m,2H); 3.7 (s,3H); 3.95 (d,1H); 4.5 (d,1H); 5.15 (d,1H); 5.8 (d,1H); 7.0 (s,1H); 7.3 (s,2H). 19. The starting material was prepared by reaction of 2,5-dimethyl-3-fluoropyrazine and trimethyloxonium tetrafluoroborate in $CH_2Cl_2$ at ambient temperature for 5 hours to give 3-fluoro-1,2,5-trimethylpyrazinium tetrafluoroborate. 20. n.m.r. in solvent B: 1.53 (s,6H); 2.38 (s,3H); 2.53 (s,3H); 3.5 (m,2H); 4.1 (s,3H); 4.2 (d,1H); 4.85 (d,1H); 5.1 (d,1H); 5.85 (d,1H); 7.05 (s,1H); 7.9 (s,1H).

EXAMPLES 15–16

The general process described in Examples 7–14 was repeated using the appropriate 3-aminomethyl-cephalosporin derivative and the appropriate chloroheterocycle and the following compounds were obtained.

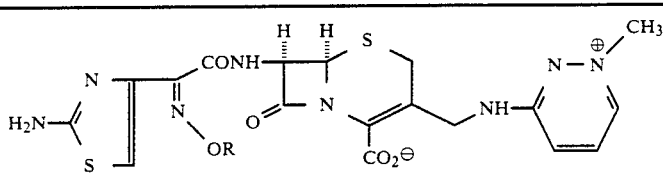

| Example | —R | Yield % | Footnotes |
|---|---|---|---|
| 15 | —CH₂CH₂S—(5-methyl-1,3,4-thiadiazol-2-yl) | 35 | 1 |
| 16 | —CH₂CH₂Br | 11 | 2 |

Footnotes 1. n.m.r. in solvent A: 2.68 (s,3H); 3.6 (m,4H); 4.0-4.8 (m,4H); 4.25 (s,3H); 5.15 (d,1H); 5.81 (d,1H); 7.0 (s,1H); 7.61 (d,1H); 7.99 (dd,1H); 8.97 (d,1H). 2. n.m.r. in solvent A: 3.6-3.9 (m,4H); 4.0-4.6 (m,4H); 4.26 (s,3H); 5.14 (d,1H); 5.82 (d,1H); 6.97 (s,1H); 7.65 (d,1H); 8.02 (dd,1H); 9.0 (d,1H).

The starting materials for use in the above process may be obtained as follows:

Reaction of ethyl 2-(2-tritylaminothiazol-4-yl)-2-((Z)-2-bromoethoxyimino)acetate (UK patent application 2017702A) with 2-mercapto-5-methyl-1,3,4-thiadiazole and hydrolysis of the ester gave 2-(2-tritylaminothiazol-4-yl)-2-[(Z)-2-(5-methyl-1,3,4-thiadiazol-2-ylthio)ethoxyimino]acetic acid; n.m.r. in solvent C: 2.7 (s,3H); 3.65 (t,2H); 4.51 (t,2H); 6.65 (s,1H); 7.34 (s,15H).

Triethylamine (1.0 mmole.) and phosphorus pentachloride (1.0 mmole) were added to a solution of 2-(2-tritylaminothiazol-4-yl)-2-[(Z)-2-(5-methyl-1,3,4-thiadiazol-2-ylthio)ethoxyimino]acetic acid (1.0 mmole) in $CH_2Cl_2$ (2.5 ml.) under argon at 0° and the mixture stirred for 1.5 hours. The solvent was evaporated and the residue dissolved in $CH_2Cl_2$. To this solution was added a solution of 7-amino-3-azidomethylceph-3-em-4-carboxylic acid (1.0 mmole.) in $CH_2Cl_2$ (2.5 ml.) under argon [this solution having been previously treated at 0° with N,O-bistrimethylsilylacetamide (2.0 mmole.) and allowed to warm to ambient temperature over 2 hours]. After 1.5 hours the mixture was diluted with $CH_2Cl_2$ and the organic layer washed with water, brine and dried ($MgSO_4$) Evaportion of the solvent and purification of the residue by chromatography on silica gel gave the product. Using this general process the following compounds were prepared.

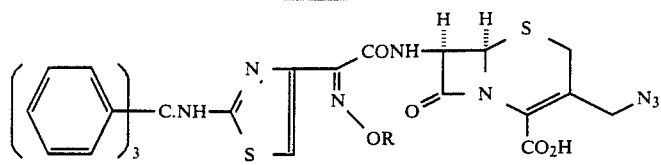

| —R | Footnotes |
|---|---|
| —CH₂CH₂S—[N=N/S thiadiazole]—CH₃ | 1 |
| —CH₂CH₂Br | 2, 3 |

Footnotes 1. n.m.r. in solvent A: 2.68 (s,3H); 3.64 (m,4H); 3.92 (d,1H); 4.46 (d,1H); 4.48 (m,2H); 5.2 (d,1H); 5.8 (d,1H); 6.92 (s,1H); 7.37 (s,15H). 2. The starting material was 2-(2-tritylamino-thiazol-4-yl)-2-((Z)-2-bromoethoxyimino)acetic acid (UK patent application 2017702A). 3. n.m.r. in solvent A: 3.5–3.9 (m,4H); 4.2–4.5 (m,4H); 5.16 (d,1H); 5.76 (d,1H); 6.8 (s,1H); 7.34 (s,15H).

The 3-azidomethylcephalosporin derivative was dissolved in formic acid and treated with an excess of wet Raney nickel for 50 minutes. The mixture was filtered through diatomaceous earth and the pad rinsed with MeOH/water 1:1 v/v. The filtrate was evaporated and the residue dissolved in TFA/water 9:1 v/v (5 ml.) at ambient temperature. After 1.5 hours the solvent was evaporated and the residue purified by chromatography on Diaion HP 20 resin, eluting with increasing proportions of MeOH in water. There were thus obtained the following compounds.

| —R | Footnotes |
|---|---|
| —CH₂CH₂S—[N—N/S thiadiazole]—CH₃ | 1 |
| —CH₂CH₂Br | 2 |

Footnotes 1. n.m.r. in solvent A: 2.67 (s,3H); 3.62 (m,6H); 4.47 (t,2H); 5.15 (d,1H); 5.86 (d,1H); 7.0 (s,1H); 2. n.m.r. in solvent A: 3.65–3.9 (m,6H); 4.42 (t,2H); 5.17 (d,1H); 5.88 (d,1H); 6.97 (s,1H).

EXAMPLE 17

To a solution of 3-aminomethyl-7-[2-(2-aminothiazol-4-yl)-2-((Z)-1-carboxy-1-methoxyethoxyimino)-acetamido]ceph-3-em-4-carboxylic acid (400 mg.) and 4-chloro-1,7-dimethyl-1,8-naphthyridinium tetrafluoroborate (190 mg.) in DMF (2 ml.) was added triethylamine (285 ul.) at ambient temperature. After 1 hour the solvent was evaporated and the residue purified by HPLC on an octadecylsilane column using MeOH/aqueous ammonium carbonate (2 g./l) 30:70 v/v as eluant to give the following compound

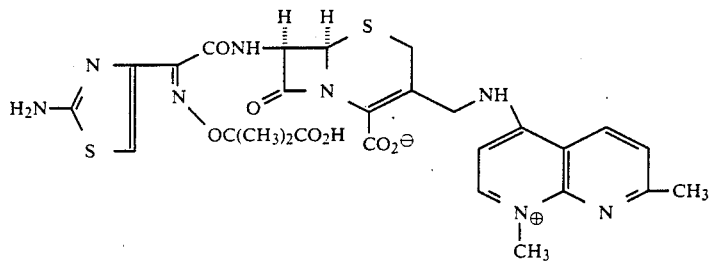

in 10% yield, n.m.r. in solvent B: 1.5 (s, 6H); 2.73 (s,3H); 3.6 (s,2H); 4.1 (s,3H); 4.65 (s,2H); 5.2 (d,1H); 6.9 (d,1H); 7.0 (s,1H); 7.0 (d,1H); 7.7 (d,1H); 8.8 (dd,1H).

The starting material may be obtained as follows. 3-Carboxty-4-hydroxy-7-methyl-1,8-naphthyridine was heated at 300° in a tube equipped with a cold finger to give 4-hydroxy-7-methyl-1,8-naphthyridine. Reaction of this compound with phosphorous oxychloride at 100° for 30 minutes gave 4-chloro-7-methyl-1,8-naphthyridine. Reaction of this compound with trimethyloxonium tetrafluoroborate in CH₂Cl₂ at ambient temperature for 3 hours gave, after evaporation of solvent and washing of the residue with ether, 4-chloro-1,7-dimethyl-1,8-naphthyridinium tetrafluoroborate which was used without further purification.

EXAMPLES 18–24

The following compounds were prepared by reaction of 3-aminomethyl-7-[2-(2-aminothiazol-4-yl)-2-((Z)-1-carboxy-1-methylethoxyimino)acetamido]ceph-3-em-4-carboxylic acid with the appropriate quaternary heterocycle in the manner described in Example 1.

[Structure: H₂N-C(=N)-S-thiazole-CONH-β-lactam-cephem with -CH₂-NHR substituent, OC(CH₃)₂CO₂H oxime, CO₂⁻]

| Example | R | Yield (%) | Footnotes |
|---|---|---|---|
| 18. | [pyridazinium with two CH₃ groups] | 22 | 1 |
| 19. | [thiazolo-pyridinium, vinyl] | 27 | 2,3 |
| 20. | [thiazolo-pyridinium, ethyl] | 40 | 4,5 |
| 21. | [thiazolo-pyridinium with CO₂H] | 14 | 6,7 |
| 22. | [thiazolo-pyridinium with CH₂CO₂C₂H₅] | 13 | 8,9 |
| 23. | [benzothiazolo-pyridinium] | 14 | 10,11 |
| 24. | [thiadiazolo-pyridinium with CH₃] | 16 | 12,13 |

Footnotes 1. N.m.r. in solvent A: 1.42 (s, 6H), 2.52 (s, 3H), 2.7 (s, 3H), 3.68 (dd, 2H), 4.42 (d, 1H), 4.8 (d, 1H) 5.12 (d, 1H), 5.9 (d, 1H), 7.0 (s, 1H) 7.82 (m, 1H), 8.1 (d, 1H). 2. N.m.r. in solvent A: 1.42 (s, 6H), 3.32 (d, 1H), 3.61 (d, 1H), 4.22 (d, 1H), 4.61 (d, 1H), 5.05 (d, 1H), 5.76 (d, 1H), 6.72 (s, 1H) 7.02 (d, 1H), 7.78 (d, 1H), 8.1 (d, 1H), 8.7 (d, 1H). 3. The starting material may be prepared as follows:

Lawesson's reagent (5.26 g.) was added to a boiling solution of 8H-thiazolo[3,2-a]pyrimidin-7-one (4.0 g.) in CH₃CN(200 ml.) and the mixture was heated under reflux with stirring for 1.5 h. On cooling silica gel (70-230 mesh, 15 g.) was added and the mixture was evaporated to dryness. The residue was applied to a column of silica gel (300 g.) and eluted with MeOH/CH₂Cl₂ (5-10% to give 8H-thiazolo[3,2-a]-pyrimidin-7-thione (2.7 g.). Trimethyloxonium tetrafluoroborate (2.0 g.) was added to a stirred suspension of 8H-thiazolo[3,2-a]pyrimidin-7-thione (1.5 g.) in dry CH₃CN (50 ml.). After stirring for 2 h, the solution was concentrated to about 20 ml., and with vigorous stirring anhydrous ether (100 ml.) was added to precipitate 7-methylthiothiazolo[3,2-a]-pyrimidinium tetrafluoroborate (1.3 g.), having nmr in d₆ DMSO:

2.78 (s, 3H), 8.04 (d, 1H), 8.22 (d, 1H), 8.55 (d, 1H), 9.24 (d, 1H). 4. N.m.r. in solvent A: 1.42 (s, 6H), 3.5 (d, 2H) 3.68 (m, 2H), 4.18 (d, 1H), 4.6 (m, 3H), 5.1 (d, 1), 5.82 (d, 1H), 6.62 (d, 1H), 6.72 (s, 1H), 8.12 (d, 1H). 5. Starting from 2,3-dihydro-8H-thiazolo[3,2-a]-pyrimidin-7-one, 2,3-dihydro-7-methylthiothiazolo-[3,2-a]pyrimidinium tetrafluoroborate was prepared in the same way as described in footnote 3. 6. N.m.r. in solvent A: 1.42 (s, 6H), 3.58 (dd, 2H), 4.25 (d, 1H), 4.75 (d, 1H), 5.1 (d, 1H), 5.82 (d, 1H), 6.75 (s, 1H), 7.39 (s, 1H), 7.6 (d, 1H), 9.21 (s, 1H). 7. Starting from 5-methoxycarbonyl-8H-thiazolo[3,2-a]pyrimidin-7-one, 5-methoxycarbonyl-7-methylthiothiazolo[3,2-a]pyrimidinium tetraborate was prepared in the same way as described in footnote 3. Upon reaction with the aminomethylcephalosporin, as described in Example 1, this material underwent hydrolysis of the methyl ester in addition to displacement of the methylthio group. 8. N.m.r. in solvent A: 1.12 (t, 3H), 1.42 (s, 6H), 2.7 (s, 2H), 3.3 (d, 1H), 3.58 (d, 1H), 4.2 (d, 1H), 4.6 (d, 1H), 5.09 (d, 1H), 5.68 (d, 1H), 6,66 (s, 1H), 8.0 (d, 1H), 8.1 (s, 1H), 9.18 (d, 1H). 9. The starting material may be prepared as follows:

2-Amino-5-ethoxycarbonylmethylthiazole (3.72 g.), ethyl propiolate (1.96 g.) and 25% aqueous tetramethyammonium hydroxide (0.15 ml.) in absolute etOH (50 ml.) were treated under reflux for 16 h. The solution was concentrated and the residue purified by column chromatography (silica gel; 10% MeOH/CH₂Cl₂) to give 3-ethoxycarbonylmethyl-8H-thiazolo[3,2-a]pyrimidin-7-one (1.6 g.), as a solid having nmr in d₆ DMSO:

1.2 (t, 3H), 4.1 (m, 4H), 6.15 (d, 1H), 7.15 (s, 1H), 8.18 (d, 1H). This material was converted to 3-ethoxycarbonylmethyl-7-methylthiothiazolo[3,2-a]-pyrimidinium tetrafluoroborate in the same way as described in footnote 3. 10. N.m.r. in solvent A: 1.4 (s, 6H), 3.35 (d, 1H), 3.65 (d, 1H), 4.32 (d, 1H), 4.65 (d, 1H), 5.05 (d, 1H), 5.78 (d, 1H), 6.75 (s, 1H), 7.12 (d, 1H), 7.7 (m, 2H), 8.25 (m 1H), 9.23 (d, 1H). 11. 1H-Benzo[4,5]thiazolo[3,2-a]pyrimidin-2-one was converted to 2-methylthiobenzo[4,5]thiazolo[3,2-a]pyrimidinium tetrafluoroborate in the same way as described in footnote 3. 12. N.m.r. in solvent A: 1.4 (s, 6H), 2.75 (s, 3H) 3.35 (d, 1H), 3.61 (d, 1H), 4.28 (d, 1H) 4.68 (d, 1H), 5.04 (d, 1H). 5.78 (d, 1H), 6.72 (s, 1H), 7.03 (d, 1H), 8.98 (d, 1H). 13. 8H-2-Methyl-1,3,4-thiadiazolo[3,2-a]pyrimidin-7-one was converted to 2-methyl-7-methylthio-1,3,4-thiadiazolo[3,2-a]pyrimidinium tetrafluoroborate in the same way as described in footnote 3.

EXAMPLES 25-28

To a stirred suspension of 3-aminomethyl-7-[2-(2 aminothiazol-4-yl)-2-((Z)-1-carboxy-1-methylethoxyimino)acetamido]ceph-3-em-4 carboxylic acid (200 mg.-0.4 mmole) and triethylamine (120 μl.-0.8 mmole) in DMF(2 ml.) at 25° C. was added to the appropriate N-alkylated-4-methylthio pyrimidinium salt (0.6 mmole).

After 30 minutes, the solution was evaporated to dryness under reduced pressure and the residue purified by preparative HPLC (octadecyl silane column).

Using this general process and the appropriate quaternised heterocycle the following compounds were obtained.

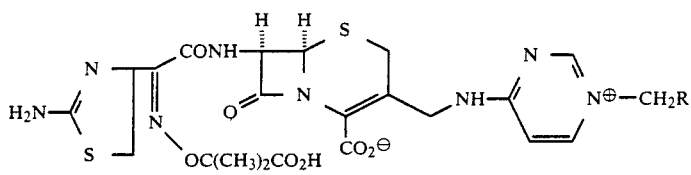

| Examples | R | Yield (%) | Footnotes |
|---|---|---|---|
| 25. | ![structure with NH2 groups and S] | 67 | 1 2 |
| 26. | -CH=CH-C6H5 | 25 | 3 4 |
| 27. | ![thiophene] | 24 | 5 6 |
| 28. | ![imidazole NH] | 25 | 7 8 |

Footnotes 1. N.m.r. in solvent B: 1.54 (s, 6H), 3.60 (m, 2H), 4.3 (d, 1H), 4.8 (d, 1H), 5.2 (br, 1H), 5.3 (s, 2H), 5.9 (br, 1H), 7.0 (d, 1H), 7.1 (s, 1H), 7.5 (s, 1H), 8.3 (s, 1H), 9.0 (s, 1H). 2. The pyrimidinium salt may be prepared as follows:

A suspension of 4-methylthiopyrimidine (350 mg. 2.8 mmole) and alkyl halide (2.8 mmole) was heated at 80° C. for 1 hour The residue was triturated with EtOAc and the resulting solid filtered off.

N.m.r. in solvent B: 2 52 (s, 3H), 5.6 (s, 2H), 7.5 (s, 1H), 8.1 (d, 1H), 9.0 (d, 1H), 9.62 (s, 1H). 3. N.m.r in solvent B: 1.54 (s, 6H), 3.6 (m, 2H), 4.3 (d, 1H), 4.8 (d, 1H), 5.0 (d, 2H); 5.2 (d, 1H), 5.9 (d, 1H), 6.8 (s, 1H), 7.05 (m, 3H), 7.45 (m, 5H), 8.3 (d, 1H), 8.95 (s, 1H). 4. The starting material may be prepared in the same way as described in footnote 2 N.m.r. in solvent B: 2.74 (s, 3H), 5.36 (d, 2H), 6.8 (m, 2H), 7.4 (m, 5H), 8.12 (d, 1H), 8.93 (d, 1H), 9.6 (s, 1H). 5. N.m.r. in solvent B: 1.54 (s, 6H), 3.56 (m, 2H), 4.3 (d, 1H) 4.8 (d, 1H), 5.2 (d, 1H), 5.6 (s, 2H), 5.9 (d, 1H) 7.0 (m, 2H), 7.05 (s, 1H), 7.24 (s, 1H), 7.46 (d, 1H), 8.2 (d, 1H), 9.0 (s, 1H). 6. The starting material may be prepared in the same way as described in footnote 2.

N.m.r. in solvent B: 2 74 (s, 3H), 5.87 (s, 2H), 6.9–7.8 (m, 3H), 8.06 (d, 1H), 8.95 (d, 1H), 9.6 (s, 1H). 7. N.m.r. in solvent B: 1.54 (s, 6H), 3.6 (m, 2H), 4.4 (d, 1H), 4.8 (d, 1H), 5.2 (d, 1H), 5.8 (s, 2H), 5.95 (d, 1H), 7.04 (d, 1H), 7.15 (s, 1H), 7.7 (s, 2H), 8.3 (d, 1H), 9.0 (s, 1H). 8. The starting material may be prepared in the same way as described in footnote 2.

N.m.r. in solvent B: 2.74 (s, 3H), 6.12 (s, 2H), 7.7 (s, 2H), 8.3 (d, 1H), 9.1 (d, 1H), 9.7 (s, 1H).

EXAMPLE 29

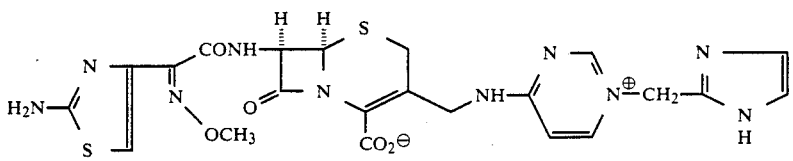

To a stirred suspension of 3-aminomethyl-7-[2-(2-aminothiazol-4-yl)-2-((Z)-1-methoxyimino)acetamino]-ceph-3-em.-4-carboxylic acid (205 mg. - 0.5 mmole) and triethylamine (70μl 0.5 mmole) in DMF (2.ml.) at 25° C. was added the quaternised pyrimidine described in Example 28, footnote 8 (185 mg. 0.5 mmole). After 30 min the solution was evaporated to dryness and the residue was purified by preparative HPLC (octecycl silane column). Yield 33%. N.m.r. in solvent B: 3.6 (m, 2H), 4.0 (s, 3H), 4.3 (d, 1H), 4.8 (d, 1H), 5.15 (m, 1H), 5.85 (br, 3H), 7.05 (m, 2H), 7.7 (s, 2H), 8.3 (d, 2H), 9.0 (s, 1H).

EXAMPLE 30

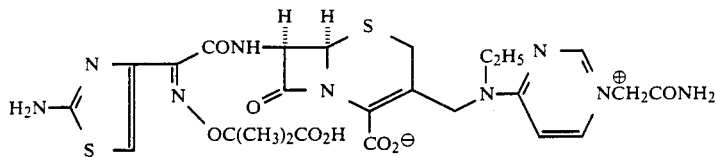

To a stirred suspension of 3-ethylamino-methyl-7-[2-(2-aminothiazol-4-yl)-2-((Z)-1-carboxy-1-methylethoxyimino)acetamido]ceph-3-em-4-carboxylic acid (160 mg. 0.31 mmole) and triethylamine (85μl - 0.62 mmole) in DMF (2 ml.) at 25° C. was added the N-alkylated-4-methylthiopyrimidine (140 mg. 0.62 mmole).

To a stirred suspension of 3-ethylamino-methyl-7-[2-(2-aminothiazol-4-yl)-2-((Z)-1-carboxy-1-methylethoxyimino)acetamido]ceph-3-em-4-carboxylic acid (160 mg. 0.31 mmole) and triethylamine (85,μl - 0.62 mmole) in DMF (2 ml.) at 25° C. was added the N-alkylated-4-methylthiopyrimidine (140 mg. 0.62 mmole). After 2 hr. at 45° C., the solution was evaporated to dryness and the residue was purified by preparative HPLC.

N.m.r. in solvent B: 1.16 (m, 3H), 1.54 (s, 6H), 3.6 (m, 4H), 4,6-5.3 (m, 5H), 5.9 (d, 1H), 7.05 (s, 1H), 7.2 (m, 1H), 8.3 (d, 1H), 8,8 (s, 1H).

The starting material may be prepared as follows:

A suspension of 4-methylthiopyrimidine (504 mg. 4 mmoles) and 2-chloroacetamide (375 mg. 4 mmoles) was heated at 90° C. for 3 hr. The reaction mixture was triturated with EtOAc, and the resulting solid was filtered off.

N.m.r. in solvent B: 2.52 (s, 3H), 5.2 (s, 2H), 8.1 (d, 1H), 8.8 (d, 1H), 9.3 (s, 1H).

EXAMPLES 31-32

The process described in Example 29 was repeated, using 3-ethylaminomethyl-7-[2-(2-aminothiazol-4-yl)-2-((Z)-2-chloroethoxyimino)acetamido]ceph-3-em-4-carboxylic acid as starting material, to give the following compounds:

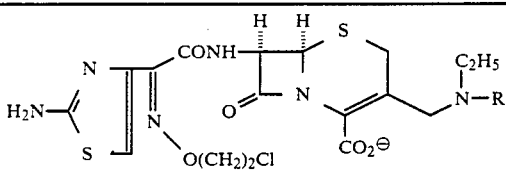

| Example | R | Yield (%) | Footnotes |
|---|---|---|---|
| 31. | ![N-N(CH3)-pyridine-NH2] | 12 | 1,2,3 |
| 32. | ![N-pyridinium-CH2CONH2] | 31 | 1,2,4 |

Footnotes 1. To a solution of 3-aminomethyl-7-[2-(2-aminothiazol-4-yl)-2-((Z)-2-chloroethoxyimino)-acetamido]ceph-3-em-4-carboxylic acid. (2 g. 4.3 mmoles) in MeOH (120 ml.) was added triethylamine (0.6 ml.-4.3 mmoles) and sodium cyanoborohydride (0.14 g.-2.2 mmoles). After addition of acetaldehyde (0.15 ml.-2.2 mmoles) the mixture was stirred at room temperature for 1 hour. After evaporation the residue was purified on HP20 resin.

N.m.r. in solvent B: 1.21 (s, 3H), 2.8-3.1 (m, 2H), 3.2-4.2 (m, 6H), 4.2-4.6 (m, 2H), 5.4 (d, 1H), 5.8 (d, 1H) 7.1 (s, 1H). 2. The above 3-ethylaminomethyl cephalosporin was reacted with the appropriate quaternised heterocycle in the same way as described in Example 30. 3. N.m.r. in solvent B: 1.2 (br, 3H), 3.5 (br, 4H), 3.85 (s, 3H), 4.0 (br, 2H), 4.5 (m, 4H), 5.3 (d, 1H), 5.9 (d, 1H), 7.05 (s, 1H), 7.4 (d, 1H), 7.8 (d, 1H). 4. N.m.r. in solvent B: 1.2 (br, 3H), 3.0-4.0 (m, 6H), 4.2-5.3, (m, 7H), 5.85 (d, 1H), 7.04 (s, 1H), 7.2 (d, 1H), 8.3 (d, 1H) 8.7 (s, 1H).

EXAMPLES 33-34

The process described in Example 25 was repeated, using the appropriate methylthio heterocycle, to give the following compounds.

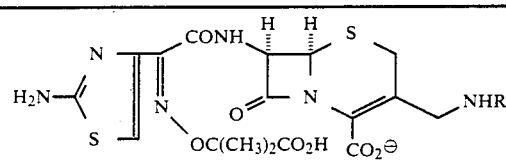

| Example | R | Yield (%) | Footnotes |
|---|---|---|---|
| 33. | ![pyrido-pyrimidinium-CH3] | 42% | 1,2 |
| 34. | ![pyrido-pyrimidinium-N-CH3] | 14% | 3,4 |

1. N.m.r. in solvent B: 1.55 (s, 6H), (s, 6H), 3.6 (m, 2H), 4.02 (s, 3H), 4.7 (d, 1H), 5.1 (d, 1H), 5.2 (d, 1H), 5.9 (d, 1H), 7.05 (s, 1H), 7.9 (m, 1H), 9.1 (m, 3H). 2. The starting material may be obtained as follows:

4-Methylthiopyrido[2,3-d]pyrimidine (700 mg. -4 mmoles) was reacted with trimethyloxonium tetrafluoroborate (582 mg. 4 mmoles) in CH2Cl2 (20 ml.) at ambient temperature for 1 hr. After filtration the solvent was evaporated to give a solid which was used without further purification. 3. N.m.r. in solvent B: 1.55 (s, 6H), 3.65 (br, 2H), 4.37 (s, 3H), 4.6 (d, 1H), 5.0 (d, 1H), 5.2 (d, 1H), 5.9 (d, 1H), 7.0 (s, 1H), 8.0 (m, 1H), 8.8 (s, 1H), 9.45 (m, 2H). 4. The solid obtained in footnote 2 was used after trituration in MeOH.

EXAMPLE 35

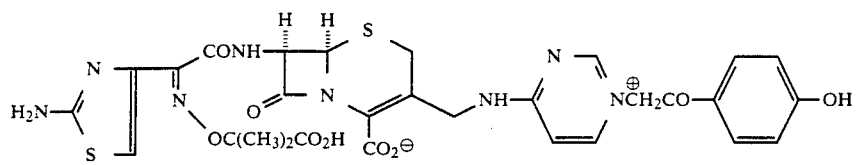

To a stirred suspension of 3-aminomethyl-7-[2-(2 aminothiazol-4-yl)-2-((Z)-1-carboxy-1-methylethoxyimino)acetamido]ceph-3-em-4-carboxylic acid (200 mg. -0.4 mmole) and triethylamine (120 μl. - 0.8 mmole) in DMF (2 ml.) at 25° C. was added the N-alkylated-4-methylthio heterocycle (0.6 mmole). After 30 min., the solution was evaporated to dryness under reduced pressure and the residue purified by preparative HPLC (octadecyl silane column).

N.m.r. in solvent B: 1.54 (s, 6H), 3.6 (m, 2H), 4.35 (d, 1H), 4.8 (d, 1H), 5.2 (d, 1H), 5.8 (s, 2H), 5.9 (d, 1H), 7.0 (m, 4H), 7.9 (d, 2H), 8.1 (d, 1H), 8.7 (s, 1H).

The methylthio heterocycle used as starting material may be prepared in the same way as described in Example 25, footnote 2.

N.m.r. in solvent B: 2.75 (s, 3H), 6.14 (s, 2H), 7.0 (d, 2H), 8.0 (d, 2H), 8.2 (d, 1H), 8.8 (d, 1H), 9.4 (s, 1H).

EXAMPLES 36–37

The process described in Example 30 was repeated, using the appropriate methylthio heterocycle as starting material, to give the following compounds:

| Example | R | Yield (%) | Footnotes |
|---|---|---|---|
| 36. | (4-methyl-1-methylpyrido-pyridinium) | 46% | 1,2 |
| 37. | (N-methylene-thiophene pyridinium) | 46% | 3,4 |

Footnotes:
N.m.r. solvent B: 1.52 (s, 9H), 3.51 (s, 2H), 4.0 (s, 5H), 4.95 (d, 1H), 5.2 (m, 2H), 5.9 (d, 1H), 7.0 (s, 1H), 7.9 (m, 1H), 8.7 (d, 1H), 9.1 (m, 2H). 2. The starting material was described in example 33, footnote 2. 3. N.m.r. in solvent B: 1.13 (m, 3H), 1.53 (s, 6H), 3.2–3.9 (m, 4H), 4.6 (d, 1H), 4.8–5.3 (m, 2H), 5.6 (s, 2H), 5.85 (d, 1H), 6.9–7.6 (m, 5H), 8.4 (d, 1H), 9.0 (s, 1H). 4. Starting material described in Example 27, Footnote 6.

EXAMPLE 38

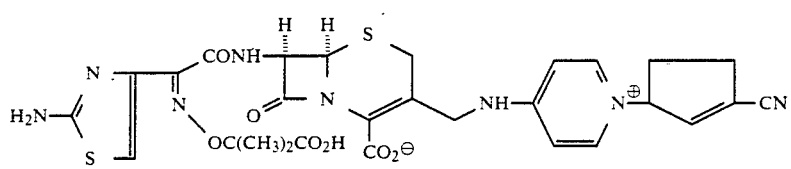

The general process described in Example 27 was repeated, using the appropriate 4-methylsulphinyl pyridinium salt.

N.m.r. in solvent B: 1.54 (s, 6H), 2.5 (br, 2H), 2.8 (br, 2H), 3.55 (m, 2H), 4.35 (br, 2H), 5.2 (d, 1H), 5.7 (m, 1H), 5.9 (d, 1H), 7.0 (m, 4H), 8.2 (m, 2H).

The pyridinium salt used as starting material may be obtained by condensation of the known 4-methylthiopyridine and 3-bromo-1-cyanocyclopentene in MeOH at 20° C. for 12 hr.

N.m.r. in solvent B: 2.3–3.0 (m, 7H), 5.8 (br, 1H), 6.7 (s, 1H), 7.6 (d, 2H), 8.5 (d, 2H).

This product, as its tetrafluoroborate salt, was oxidised with MCPBA in CH$_2$Cl$_2$/TFA at 20° C. for 3 hr. After evaporation of the solvents the solid was triturated with ether and used without further purification.

EXAMPLES 39–53

A solution of NaHCO$_3$ (0.6 mM) in water (750 ml.) was added to a solution of 7-acyl-3-aminomethyl-cephalosporin derivative (0.2 mM) in DMF (2 ml.), followed after a few minutes by the appropriate quaternised heterocyclic starting material (0.22 mM). The mixture was stirred at room temperature during 3 hrs. The mixture was evaporated to dryness and the residue purified by HPLC on an octadecylsilane column.

Using this general process the following compounds were prepared.

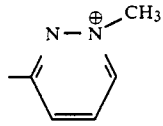
| Example | $R_1$ | $R_2$ | Yield (%) | Footnotes |
|---|---|---|---|---|
| 39. | —CH$_2$CH=CHCO$_2$H | 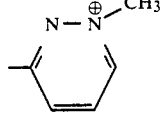 | 36 | 1,2 |
| 40. | —CH$_2$CH$_2$SOCH$_3$ | 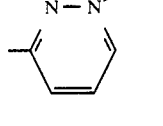 | 32 | 3,4 |
| 41. | —CH$_2$CH$_2$SO$_2$CH$_3$ | 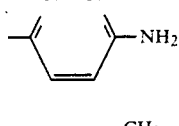 | 59 | 5,6 |
| 42. | —CH$_2$CH$_2$SOCH$_3$ | 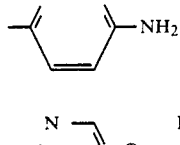 | 32 | 7,8 |
| 43. | —CH$_2$CN | 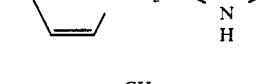 | 37 | 9,10 |
| 44. | —CH$_2$CN | 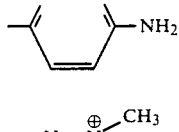 | 49 | 11,12 |
| 45. | —CH$_2$CH$_2$F | 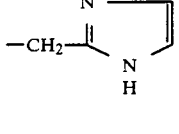 | 40 | 13,14 |
| 46. | 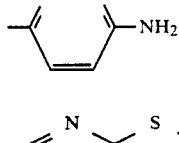 | 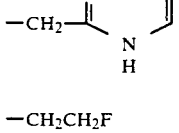 | 37 | 15,16 |
| 47. | 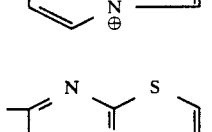 | 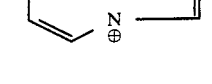 | 55 | 17,18 |
| 48. | —CH$_2$CH$_2$F | 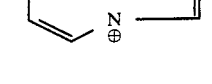 | 21 | 19,20 |

-continued

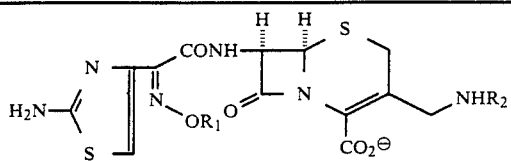

| Example | R₁ | R₂ | Yield (%) | Footnotes |
|---|---|---|---|---|
| 49. | —CH$_2$CF$_3$ | (4-methyl-thieno[2,3-d]pyrimidinium, N-methyl) | 45 | 21,22 |
| 50. | —CH$_2$CF$_3$ | (dihydrothiazolopyridinium) | 48 | 23,24 |
| 51. | —CH$_2$CF$_3$ | (1-methyl-6-amino-pyridazinium) | 31 | 25,26 |
| 52. | —CH$_2$—(1-methylimidazol-2-yl) | (thiazolopyridazinium) | 30 | 27,28 |
| 53. | —CH$_2$CH$_2$F | (1-(4-sulfobenzyl)pyridinium) | 52 | 29,30 |

1. Reaction time: 1 Hour 40 minutes. 2. N.m.r. in solvent B: 3.35-3.85 (m, 2H), 4.3 (s, 3H), 4.1-4.5 (m, 2H), 4.8 (d, 2H), 5.2 (d, 1H), 5.9 (d, 1H), 6.1 (d, 1H), 7.05 (s, 1H), 6.8-7.2 (m, 1H), 7.8-9.1 (m, 4H). 3. The process was carried out using 3-aminomethyl-7-[2-(2-aminothiazol-4-yl)-2-(Z-methylthioethoxyimino)acetamido]-ceph-3-em-4-carboxylic acid and 3-chloro-1-methyl-pyridinium iodide, during 2 hours. The crude product was not purified after evaporation but was oxidised directly as follows:

A solution of crude 7-[2-(2-aminothiazol-4-yl)-2-(Z-methylthioethoxyimino)acetamido]-3-(1-methyl-3-pyridazinio)aminomethylceph-3-em-4-carboxylic acid (0.5 mM) in TFA (4.0 ml.) and CH$_2$Cl$_2$ (6.0 ml.) was cooled to −25° C. with vigorous stirring m-chloroperbenzoic acid (0.5 mM) was added portionwise during 1 hr. The temperature was allowed to rise to ambient, the mixture was evaporated to dryness and the residue was purified by HPLC on an octadecylsilane column. 4. N.m.r. in solvent B: 2.6 (s, 3H), 3.2 (d, 2H), 3.6 (dd, 2H), 4.3 (s, 3H), 4.6 (m, 4H), 5.2 (d, 1H), 5.8 (d, 1H), 7.1 (s, 1H), 7.65 (d, 1H), 8.0 (dd, 1H) 8.9 (d, 1H). 5. Reaction time 1 Hour 45 minutes. 6. N.m.r. in solvent B: 2 9 (s, 3H), 3.5-3.7 (m, 4H), 4.2 (s, 3H), 4.5-4.7 (m, 4H), 5.1 (d, 1H), 5.75, (d, 1H), 7.05 (s, 1H), 7.55 (d, 1H), 8.0 (dd, 1H), 9.0 (d, 1H). 7. Prepared in two stages, condensation and oxidation as in footnote 3. Reaction time for the condensation: 4 hours 30 minutes at 50° C. 8. N.m.r in solvent B: 2 61 (s, 3H), 3.2 (d,2H), 3.9 (s, 5H), 4.7 (m, 4H), 5.2 (d, 1H), 5.9 (d, 1H), 7.05 (s, 1H), 7.65 (d, 1H), 7.75 (d, 1H). 9. Reaction time 2 hours 30 minutes at 50° C. 10. N.m.r. in solvent B: 3.53 (m, 2H), 3.7 (s, 3H), 4.23 (m, 2H), 5.08 (s, 2H) 5.2 (d, 1H), 5.77 (d, 1H) 7.08 (s, 1H), 7.34 (s, 2H). 11. Reaction time: 2 hours. 12. N.m.r. in solvent B: 3.51 (m, 2H), 4.52 (m, 2H), 5.05 (s, 2H), 5.11 (d, 1H), 5.75 (s, 2H), 5.8 (d, 1H) 7.0 (d, 1H), 7.17 (s, 1H), 7.78 (s, 2H), 8.24 (d, 1H), 8.96 (s, 1H). 13. Reaction temperature: 50° C. 14. N.m.r. in solvent B: 3.5 (m, 2H), 3.7 (s, 3H), 3.8-4.6 (m, 5H), 4.9 (m, 1H), 5.15 (d, 1H), 5.78 (d, 1H), 6.99 (s, 1H), 7.3 (s, 2H). 15. Reaction temperature: 50° C. 16. N.m.r. in solvent B: 3.6 (m, 2H), 3.72 (s, 3H), 4.3 (dd, 2H), 5.15 (d, 1H), 5.43 (s, 2H), 5.8 (d, 1H), 7.06 (s, 1H), 7.33 (s, 2H), 7,73 (s, 2H). 17. Reaction time: 45 minutes at 50° C. 18. N.m.r. in solvent B: 3.55 (m, 2H), 4.5 (dd, 2H), 5.05 (d, 1H), 5.45 (s, 2H), 5.8 (d, 1H), 7.0 (d, 1H), 7.05 (s, 1H), 7.65 (d, 2H), 7.7 (d, 1H), 8.05 (d, 1H), 8.80 (d, 1H). 19. Reaction time: 20 hours. 20. N.m.r. in solvent B: 3.5 (m, 2H), 4.1-4.8 (m, 5H), 4.9 (m, 2H), 5.13 (d, 1H), 5.81 (d, 1H), 7.01 (d, 1H), 7.02 (s, 1H), 7.65 (d, 1H), 8.11 (d, 1H), 8.74 (d, 1H). 21. Reaction time: 1 hour. 22. N.m.r. in solvent B: 3.42 (d, 1H), 3.68 (d, 1H), 4.07 (s, 3H), 4.57 (d, 1H), 4.95 (d,1H), 4.64 (d, 1H), 4.82 (d, 1H), 5.12 (d, 1H), 5.77 (d, 1H), 7.07 (s, 1H), 7.91 (s, 2H), 8.85 (s, 1H). 23. Reaction time: 1 hour. 24. N.m.r. in solvent B: 3 57 (d, 1H), 3.65 (d, 1H), 3.67 (t, 2H), 4.18 (d, 1H), 4.4-4.9 (m, 5H), 5.11 (d, 1H), 5.78 (d, 1H), 6.61 (d, 1H), 7.0 (s, 1H), 8.15 (d, 1H). 25. Reaction time: 2 hours 30 minutes at 50° C. 26. N.m.r. in solvent B: 3.4 (d, 1H) 3.62 (d, 1H), 3.68 (s, 3H), 3.95 (d, 1H), 4.42 (d, 1H), 4.63 (d, 1H), 4.82 (d, 1H), 5.11 (d, 1H), 5.74 (d, 1H), 7.0 (s, 1H), 7.3 (s, 2H). 27. Reaction time: 2 hours at 50° C. 28. N.m.r. in solvent B: 3.25 (m, 2H), 3.6 (s, 3H), 4.0 (dd, 2H), 4.8 (d, 1H), 5.15 (s, 2H), 5.5 (d, 1H), 6.65 (s, 1H), 7.15 (d, 1H), 7.4 (d, 2H), 8.25 (m, 3H). 29. Reaction time: 20 hours. 30. N.m.r. in solvent B: 3.55 (m, 2H), 4.2-4.9 (m, 5H), 4.98 (t, 1H), 5.19 (d, 1H), 5.39 (s, 2H), 5.81 (d, 1H), 7.02 (s, 1H), 7.0-7.3 (m, 2H), 7.38 (d, 2H), 7.68 (d, 2H), 8.3-8.7 (m, 2H).

The cephalosporin starting materials for use in the above process are obtained by the method described on page 33 above.

Using this general process the following compounds were prepared.

solvent A: 3.4 (s, 2H), 3.9 (d, 1H), 4.4 (d, 1H), 4.8 (s, 2H), 4.9 (d, 1H), 5.7 (d, 1H), 6.8 (s, 1H), 7.2 (s, 15H). 8. The starting material may be prepared as follows. Reaction of ethyl 2-(2-tritylaminothiazol-4-yl)-2-[(Z)-2-hydroxyethoxyimino]acetate with diethylamino sulphur trifluoride and hydrolysis of the resulting ester gave 2-(2-tritylaminothiazol-4-yl)-2[(Z)-2-fluoroethoxyimino]acetic acid.

N.m.r. in solvent A: 4.15 (m, 1H), 4.38 (m, 1H), 4.48 (m, 1H, 4.92 (m, 1H, 6.94 (s, 1H), 7.4 (s, 15H). 9. N.m.r. in solvent C: 3.4 (m, 2H), 4.2 - 4.6 (m, 4H), 4.7 (m, 1H), 5.0 (m, 1H), 5.1 (d, 1H), 5.9 (d, 1H), 6.9 (s, 1H), 7.4 (s, 15H). 10. The starting material was prepared by reaction of 2-bromomethylimidazole with N-hydroxy-

| —R | Footnotes |
|---|---|
| —CH$_2$CH=CH—CO$_2$t-Bu | 1,2 |
| —CH$_2$CH$_2$SCH$_3$ | 3,4 |
| —CH$_2$CH$_2$SO$_2$CH$_3$ | 5,6 |
| —CH$_2$CN | 7 |
| —CH$_2$CH$_2$F | 8,9 |
| —CH$_2$-(imidazol-2-yl, NH) | 10,11,12,13 |
| —CH$_2$CF$_3$ | 14,15,16,13 |
| —CH$_2$-(imidazol-2-yl, N-CH$_3$) | 17,18,15,13 |

Footnotes 1. The starting material was prepared by reaction of 4-nitrobenzyl 2-(2-tritylaminothiazol-4-yl)-2-(Z)-hydroxyiminoacetate with t-butyl 4-bromobut-2-enoate and hydrogenolysis of the resulting ester to give 2-(2-tritylaminothiazol-4-yl)-2-[(Z)-3-t-butoxycarbonylprop-2-enyloxyimino]acetic acid.

N.m.r. in solvent C: 1.44 (s, 9H), 4.75 (d, 2H), 5.92 (m, 1H), 6.56 (s, 1H), 6.7-6.9 (m, 2H), 7.29 (s, 15H). 2. N.m.r. in solvent C: 3.4 (m, 2H), 3.9 (d, 1H), 4.45 (d, 1H), 4.9 (m, 2H), 5.02 (d, 1H), 5.7 (m, 1H), 5.95 (d, 1H), 6.83 (s, 1H), 6.9 (d, 1H), 7.32 (s, 15H). 3. The starting material was prepared by reaction of ethyl 2-(2-tritylaminothiazol-4-yl)-2-((Z)-2-bromoethoxyimino)acetate (UK Patent Application 2017702A) with the sodium salt of methyl mercaptan and hydrolysis of the resulting ester to give 2-(2-tritylaminothiazol-4-yl)-2-((Z)-2-methylthioethoxyimino)acetic acid.

N.m.r. in solvent C: 2.1 (s, 8H) 2.8 (t, 2H) 4.3 (t, 2H), 6.6 (s, 1H), 7.3 (s, 15H). 4. N.m.r. in solvent C: 2.1 (s, 3H), 2.9 (m, 2H), 3.5 (s, 2H), 3.95-4.6 (m, 4H), 5.1 (d, 1H), 5.95 (d, 1H), 6.8 (s, 1H), 7.35 (s, 15H). 5. The starting material was prepared by oxidation of the product in Footnote 3 to give 2-(2-tritylaminothiazol-4-yl)-2-((Z)-2-methanesulphonylethoxyimino)acetic acid.

N.m.r. in solvent C: 2.9 (s, 3H), 3.5 (t, 2H), 4.5 t, 2H, 6.65 s, 1H, 7.3 (s, 15H). 6. N.m.r. in solvent C: 3 0 (s, 3H), 3.5-3.7 (m, 4H), 4.3 (m, 2H), 4.7 (m, 2H), 5.1 (d, 1H), 5.9 (d, 1H) 6.8 (s, 1H), 7.4 (s, 15H). 7. N.m.r. in phthalimide, deprotection to give O-(imidazol-2-yl)methylhydroxylamine and condensation with 2-(2-aminothiazol-4-yl)glyoxylic acid to give 2-(2-aminothiazol-4-yl)-2-[(Z)-(imidazol-2-yl)-methoxyimino]acetic acid.

N.m.r. in solvent B: 5.42 (s, 2H), 7.17 (s, 1H), 7.67 (s, 2H). 11. A suspension of the product from Footnote 10 (4.4 mM) in DMF (40 µl. at 0° C. was dissolved by the addition of 3M HCl in ether (8.8 mM). N-hydroxybenzotriazole (4.4 mM) and t-butyl 7-amino-3-azidomethylceph-3-em-4-carboxylate (4.0 mM) were added to the solution, followed by dropwise addition of a solution of DCCI (4.4 mM) in CH$_3$CN (15 ml.) during 20 minutes. The mixture was left t stir for 23 hours at 0° C. and 1 hour at room temperature. The precipitate was filtered, washed with DMF (3 ml.) and the residue evaporated to dryness. Trituration at 0° C. with aqueous NaHCO$_3$ (5%) yielded a yellow solid which was treated at room temperature with TFA/H$_2$O (15:1) during 2 hours. Evaporation to dryness and purification of the residue by chromatography on Dianion HP 20 resin gave the required product. 12. N.m.r. in solvent B: 3.6 (m, 2H), 4.2 (dd, 2H), 5.25 (d, 1H), 5.5 (s, 2H), 5.9 (d, 1H), 7.25 (s, 1H) 7.7 (s, 2H). 13. This molecule is not tritylated on the 14. The starting material was prepared by condensation of O-(2,2,2-trifluoroethyl)hydroxylamine with 2-(2-aminothiazol-4-yl)glyoxylic acid to give 2-(2-aminothiazol-4-yl)-2-[(Z)-2,2,2-trifluoroethoxyimino]acetic acid.

N.m.r. in solvent B: 4.73 (q, 2H), 6.93 (s, 1H). 15. The method of condensation was that described in Footnote 11. 16. N.m.r. in solvent B: 3.5 (d, 1H), 3.75 (d, 1H), 3.95 (d, 1H), 4.5 (d, 1H), 4.75 (d, 1H), 4.95 (d, 1H), 5.3 (d, 1H), 5.9 (d, 1H), 7.2 (s, 1H). 17. The starting material was prepared by reaction of O-(1-methylimidazol-2-yl)methylhydroxylamine with 2-(2-aminothiazol-4-yl)glyoxylic acid to give 2-(2-aminothiazol-4-yl)-2-[(Z)-(1-methylimidazol-2-yl)-methoxy-imino]acetic acid.

N.m.r. in solvent B: 3.90 (s, 3H), 5.51 (s, 2H), 7.17 (s, 1H), 7.57 (s, 1H), 7.62 (s, 1H). 18. N.m.r. in solvent B: 3.6 (m, 2H), 3.9 (s, 3H), 4.2 (dd, 2H), 5.2 (d, 1H), 5.5 (s, 2H), 5.85 (d, 1H), 7.05 (s, 1H), 7.7 (dd, 2H).

Using the general process of reduction described in Footnote 3 of the description of starting materials for Example 16, the following compounds were prepared:

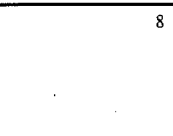

| —R | Footnotes |
|---|---|
| —CH$_2$CH=CH—CO$_2$H | 1 |
| —CH$_2$CH$_2$SCH$_3$ | 2 |
| —CH$_2$CH$_2$SO$_2$CH$_3$ | 3 |
| —CH$_2$CN | 4 |
| —CH$_2$CH$_2$F | 5 |
| —CH$_2$-[imidazol-2-yl, NH] | 6 |
| —CH$_2$CF$_3$ | 7 |

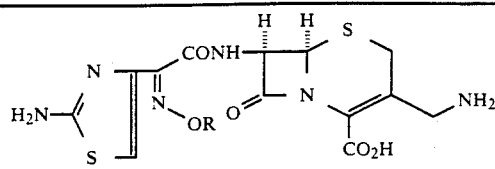

| —R | Footnotes |
|---|---|
| —CH$_2$-[1-methylimidazol-2-yl] | 8 |

1. N.m.r. in solvent B: 3.66 (s, 2H), 3.78 (m, 2H), 4.88 (m, 2H), 5.18 (d, 1H), 5.88 (d, 1H), 6.05 (d, 1H), 6.92 (d, 1H), 6.94 (s, 1H). 2. N.m.r. in solvent B: 2.1 (s, 3H), 2.85 (t, 2H), 3.6-3.9 (m, 4H), 4.4 (t, 2H), 5.2 (d, 1H), 5.9 (d, 1H), 7.1 (s, 1H). 3. N.m.r. in solvent B: 2.95 (s, 3H), 3.65 (m, 6H), 4.6 (t, 2H), 5.15 (d, 1H), 5.85 (d, 1H), 7.05 (s, 1H). 4. N.m.r. in solvent A: 3.66 (s, 2H), 3.78 (q, 2H), 5.02 (s, 2H), 5.15 (d, 1H), 5.84 (d, 1H), 6.98 (s, 1H). 5. N.m.r. in solvent B: 3.6-4.0 (m, 4H), 4.32 (m, 1H), 4.4-4.7 (m, 2H), 5.08 (m, 1H), 5.24 (d, 1H) 5.88 (d, 1H), 6.98 (s, 1H). 6. N.m.r. in solvent B: 3.8 (m, 4H), 5.15 (d, 1H), 5.43 (s, 2H), 5.86 (d, 1H), 7.12, (s, 1H), 7.66 (s, 2H). 7. N.m.r. in solvent B: 3.4-4.0 (m, 4H), 4.65 (d, 1H), 4.85 (d, 1H), 5.17 (d, 1H), 5.85 (d, 1H), 7.05 (s, 1H). 8. N.m.r. in solvent B: 3.6-3.9 (m, 4H), 3.9 (s, 3H); 5.15 (d, 1H), 5.5 (s, 2H), 5.85 (d, 1H), 7.05 (s, 1H), 7.65 (dd, 2H).

EXAMPLES 54–75

The appropriate C3$^1$-N-substituted CAZAMCA (1 eq.) and an excess (1.5 eq.) of an appropriate quaternary heterocyclic salt were reacted in a mixture of DMF/H$_2$O (2:1) in the presence of NaHCO$_3$ (4 eq.) at 40° C. for 2.5 hr., and the product was purified by HPLC, using MeOH/H$_2$O/HOAc as eluant, to give the following compounds:

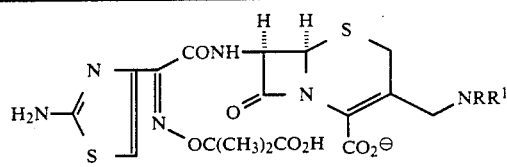

| Example | R | R$^1$ | Yield (%) | Footnotes |
|---|---|---|---|---|
| 54 | PhCH$_2$ | —[4-pyridyl]N$^\oplus$—CH$_3$ | 30 | 1,2 |
| 55 | Et | —[4-pyridyl]N$^\oplus$—CH$_3$ | 58 | 3,4 |
| 56. | furfuryl | —[4-pyridyl]N$^\oplus$—CH$_3$ | 40 | 5,6 |

-continued
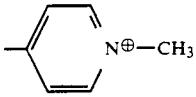
| Example | R | R¹ | Yield (%) | Footnotes |
|---|---|---|---|---|
| 57. | —CH₂.CO₂H | 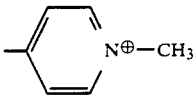 | 31 | 7,8 |
| 58. | —(CH₂)₂OH | 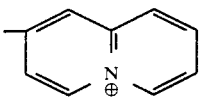 | 14 | 9,10 |
| 59. | Et | 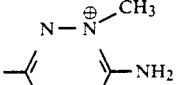 | 33 | 11 |
| 60. | Et | 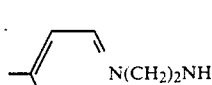 | 11 | 12 |
| 61. | Et | 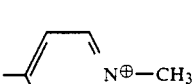 | 47 | 13 |
| 62. | 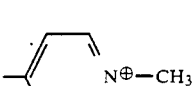 |  | 10 | 14,15 |
| 63. | —(CH₂)₂OCH₃ | 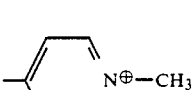 | 36 | 16,17 |
| 64. | Et | 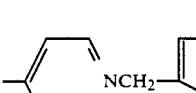 | 10 | 18 |
| 65. | i-Pr | 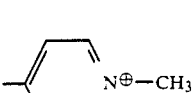 | 5 | 19,20 |
| 66. | Et | 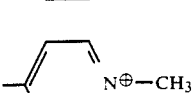 | 23 | 21 |
| 67. | —(CH₂)₂NH₂ |  | 30 | 22,23 |
| 68. | —(CH₂)₂F |  | 23 | 24,25 |

-continued

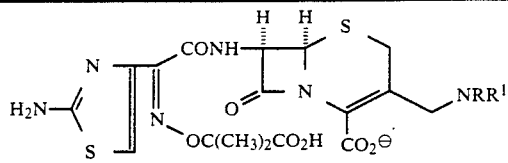

| Example | R | R¹ | Yield (%) | Footnotes |
|---|---|---|---|---|
| 69. | Et | 3-fluoro-N-methylpyridine | 15 | 26 |
| 70. | Me | N-methylpyridinium | 22 | 27,28 |
| 71. | Et | 2-methyl-N-methylpyridinium | 14 | 29 |
| 72. | allyl | N-methylpyridinium | 13 | 30,31 |
| 73. | Pr | N-methylpyridinium | 18 | 32 |
| 74. | —(CH₂)₂CN | N-methylpyridinium | 33 | 33,34 |
| 75. | —(CH₂)₂NH.CHO | N-methylpyridinium | 37 | 35 |

Footnotes 1. Eluant proportion 35:65:1. N.m.r. in solvent B: 1.55 (m, 6H), 3.4–3.6 (m, 2H), 4.0 (s, 3H), 4.7–5.0 (m, 4H), 5.2 (d, 1H), 5.9 (d, 1H), 7.1 (s, 1H), 7.2–7.5 (m, 7H), 8.4 (d, 2H). 2. The precursor C3¹ N-benzyl CAZAMCA was obtained by reductive amination of benzaldehyde with CAZAMCA. Thus, CAZAMCA (1 eq.) was treated with benzaldehyde (1.4 eq) and Et₃N (1.4 eq.) in anhydrous MeOH in the presence of 3A molecular seives with NaBH₃CN (1.4 eq.) for ½ hr. at room temperature. The product was purified by HPLC, eluant proportion 30:70:1. N.m.r. in solvent B: 1.5 (s, 6H), 3.5–3.7 (m, 2H), 3.8–4.0 (m, 2H), 4.0–4.3 (m, 2H), 5.2 (d, 1H), 5.9 (d, 1H), 7.0 (s, 1H), 7.4–7.6 (m, 5H). 3. Used 2 eq. pyridinium salt. Reaction time 1.5 hr. Eluent proportion 25:75:1. N.m.r. in solvent B: 1.6 (s, 6H), 3.2–3.8 (m, 4H), 4.0 (s, 3H), 4.6–4.8 (m, 2H), 5.3 (d, 1H), 6.0 (d, 1H), 7.15 (s, 1H), 7.2–7.4 (m, 2H), 8.2–8.4 (m, 2H).
4. The precursor C3′ N-ethyl CAZAMCA was obtained by reductive amination of acetaldehyde (1.1 eq.) with CAZAMCA (1.0 eq.) in presence of NaBH₃CN (1.0 eq.) and Et₃N (1.0 eq.). The acetaldehyde was added dropwise at room temperature in MeOH, and the mixture stirred for ½ hr. The product was purified by preparative HPLC using MeOH/H₂O/HOAc 10:90:1 v/v/v, followed by 15:85:1. N.m.r in solvent B: 1.3 (t, 3H : 1.6 (s, 6H , 2.8–3.2 (m, 2H), (m, 2H) 3.7–4.1 (m, 4H), 5.3 (d, 1H), 6.0 (d, 1H), 7.2 (s, 1H). 5. N.m.r. in solvent B: 1.55 (m, 6H), 3.3–3.6 (m, 2H), 4.0 (s, 3H) 4.8-5.0 (m, 4H), 5.2 (d, 1H), 5.95 (d, 1H), 6.4–6.6 (m, 2H) 7.1 (s, 1H) 7.3–7.6 (d, 2H), 7.6–7.7 (m, 1H) 8.3–8.6 (d, 2H). 6. The precursor was obtained by reductive amination of 2-furaldehyde with CAZAMCA, as in Footnote 2. Reaction time 1.5 hr. Eluant proportion 20:80:1. N.m.r. in solvent B: 1.6 (s, 6H), 3.6–3.8 (m, 2H), 3.9–4.1 (m, 2H), 4.2–4.4 (m, 2H), 5.25 (d, 1H), 5.95 (d, 1H), 6.5–6.8 (m, 2H), 7.1 (s, 1H), 7.8 (d, 1H). 7. Eluant proportion 30:70:1. N.m.r. in solvent B: 1.5–1.6 (m, 6h), 3.3–3.6 (m,2H), 4.0 (s, 3H), 4.4–4.6 (m, 2H), 4.6–4.8 (m, 2H), 5.3 (d, 1H), 6.0 (d, 1H), 7.1 (s, 1H), 7.0–7.5 (m, 2H), 8.3–8.5 (m, 2H). 8. Precursor obtained as in Footnote 4, starting from glyoxylic acid. Eluant proportion 15:85:1. Yield 40% N.m.r. in solvent B; 1.6 (m, 6H), 3.6–4.2 (m, 6H), 5.3 (d, 1H), 6.0 (d, 1H), 7.1 (s, 1H). 9. Eluant proportion 20:80:1. N.m.r. in solvent B: 1.55 (s, 6H), 3.2–3.6 (m, 2H), 3.5–3.8 (m, 4H), 3.35 (s, 3H), 4.6–4.8 (m, 2H), 5.2 (d, 1H), 5.9 (d, 1H), 7.1 (s, 1H), 7.3 (d, 2H), 8.3 (d, 2H). 10. Precursor obtained by reductive amination of glycolaldehyde as in Footnote 4. Eluant proportion 15:85:1. Yield 43%. N.m.r. in solvent B; 1.6 (s, 6H), 3.0–3.4 (m,2H), 3.6–4.0 (m,4H), 4.2–4.6 (m, 2H), 5.2 (d, 1H), 5.9 (d, 1H), 7.0 (s, 1H). 11. Reacted at 50° C. for 2 hrs. Eluant proportion 30:70:1. N.m.r. in solvent B: 1.2 (m, 3H), 1.5 (s, 6H), 3.2–3.8 (m, 4H), 4.6–4.8 (m, 2H), 5.2 (s, 1H), 5.9 (s, 1H), 7.1 (s, 1H), 7.2–8.0 (m, 7H). 12. Reacted at 45° C. for 20 hrs. Eluant proportion 25:75:1. N.m.r. in solvent B: 1.0–1.3 (m, 3H), 1.55 (s, 6H), 3.5–3.8 (m, 4H), 3.8 (s, 3H), 4.3 (d, 1H), 4.7 (d, 1H), 5.2 (d, 1H), 5.8 (d, 1H), 7.05 (s, 1H), 7.35 (d, 1H), 7.7 (d, 1H). 13. Reacted at room temperature for 3.5 hrs, using N-(Boc-aminoethyl)-4-chloropyridinium chloride as the quaternary heterocyclic salt. The product was deprotected by treating with TFA at room temperature for 1 hr. Eluant proportion 35:65:1. N.m.r. in solvent B: 1.0–1.3 (m, 3H), 1.6 (s, 6H), 3.2–3.8 (m, 4H), 4.3–4.8 (m, 4H), 5.2 (d, 1H) 5.9 (d, 1H), 7.1 (s, 1H), 7.2–7.4 (d, 2H), 8.3–8.5 (d, 2H). 14. Reacted at room temperature for 5 hrs. Eluant proportion 15:85:1. N.m.r. in solvent B: 1.6 (s, 6H), 3.2–3.7 (m, 2H) 4.0 (s, 3H), 4.5–4.9 (m, 2H), 5.0–5.4 (m, 2H), 5.2 (d, 1H), 5.9 (d, 1H), 7.1 (s, 1H), 7.2–7.4 (m, 2H), 7.9–8.0 (m,2H), 8.2–8.5 (m, 2H). 15. The precursor obtained as in Footnote 4 by reductive amination of pyridine-4-carboxaldehyde. Eluant proportion 20:80:1. Yield 37%. N.m.r. spectrum in solvent B: 1.6 (s, 6H), 3.6–3.8 (m, 2H), 3.9–4.3 (m, 2H), 4.4–5.0 (m, 2H), 5.2 (d, 1H), 6.0 (d, 1H), 7.1 (s, 1H), 8.0–8.3 (m, 2H), 8.8–9.2 (m, 2H). 16. Reacted at room temperature for 1.5 hrs. Eluant proportion 25:75:1. N.m.r. in solvent B: 1.55 (s, 6H), 3.2 (s, 3H), 3.2–4.0 (m, 6H), 3.9 (s, 3H), 4.6–4.9 (m, 2H), 5.2 (d, 1H), 5.9 (d, 1H), 7.1 (s, 1H), 7.2 (d, 2H), 8.2 (d, 2H). 17. The precursor was obtained as in Footnote 4 by reductive amination of 2-methoxyacetaldehyde, 2 hrs at room temperature. Eluant proportion 20:80:1. Yield 24%. N.m.r. in solvent B: 1.6 (s, 6H , 3.3 s, 3H) 3.2–4.0 (m, 8H), 5.2 (d, 1H), 5.9 (d, 1H), 7.05 (s, 1H). 18. Reacted for 2 hrs. Eluant proportion 25:75:1. N.m.r. in solvent B: 1.2 (t, 3H), 1.55 (s, 6H), 2.3 (s, 3H), 3.2–3.9 (m 4H), 4.7 (s, 2H), 4.9 (m, 2H), 5.2–5.5 (m, 3H), 5.9–6.5 (m, 2H), 7.0–7.5 (m, 5H), 7.55 (d, 2H), 8.4 (d, 2H). 19. Reaction time 8 hrs at 45° C. Eluant proportion 20:80:1. N.m.r. in solvent B: 1.1–1.4 (m, 6H), 1.6 (s, 6H), 2.2–2.4 (m, 1H), 3.2–3.6 (m, 2H), 4.0 (s, 3H), 4.2–4.8 (m, 2H), 5.2 (d, 1H), 5.9 (d, 1H), 7.1 (s, 1H), 7.3 (d, 2H), 8.3 (d, 2H). 20. The precursor was obtained as in Footnote 4, by reductive amination of acetone (4 eq.). Eluant proportion 20:80:1. Yield 50%. N.m.r in solvent B: 1.2 (d, 6H), 1.6 (s, 6H), 3.2–4.0 (m, 5H), 5.2 (d, 1H), 5.9 (d, 1H), 7.05 (d, 1H). 21. Reacted at 40°–45° C. for 4 hrs. Eluant proportion 25:75:1. N.m.r. in solvent B: 1.2 (t, 3H), 1.55 (s, 6H), 3.5 (m, 2H), 3.4–3.8 (m, 2H), 3.6 (m, 2H), 5.2 (d, 1H), 5.9 (d, 1H), 5.9 (s, 2H), 7.05 (s, 1H), 7.1–7.3 (m, 1H), 8.5 (d, 1H), 9.3 (s, 1H). 22. Reacted at room temperature for 1.5 hrs, using Boc-aminoethyl CAZAMCA as starting material. Eluant proportion 35:65:1. The product was deprotected by solution in TFA at room temperature for ½ hr. N.m.r. in solvent B: 1.55 (s, 6H), 2.6–4.0 (m, 6H), 4.0 (s, 3H, 4.6–4.9 (m, 2H), 5.3 (d, 1H), 6.0 (d, 1H), 7.0 (s, 1H), 7.2 (d, 1H), 8.2 (d, 1H). 23. The precursor was obtained by reductive amination of 2-(Boc-amino)acetaldehyde at room temperature for 2 hrs. Eluant proportion 35:65:1. Yield 20%. N.m.r. in solvent B: 1.4 (s, 9H), 1.55 (s, 6H), 2.7–3.4 (m, 4H), 3.6–4.2 (m,4H), 5.2 (d, 1H), 5.9 (d, 1H), 7.05 (s, 1H). The 2-(Boc-amino)propionaldehyde was obtained by oxidation of 2-(Boc-amino)ethanol with pyridinium chlorochromate in $CH_2Cl_2$ containing sodium acetate, at 0° C. for 2 hrs, and purification by chromatography on silica. Yield 68%. 24. Reaction time 2 hrs. at room temperature. Eluant proportion 25:75:1. N.m.r. in solvent B:1.55 (s, 6H), 3.2-3.6 (m, 2H), 3.8-4.0 (m, 2H), 4.0 (s, 3H), 4.2-4.5 (m, 1H), 4.8-5.1 (m, 1H), 4.6-4.8 (m, 2H), 5.2 (d, 1H), 5.9 (d, 1H), 7.05 (s, 1H), 7.3 (d, 1H), 8.3 (d, 1H). 25. The precursor was obtained by reductive alkylation of an excess of 2-fluoroacetaldehyde in $CH_2Cl_2$ solution, for 2.5 hrs. at room temperature. Eluant proportion 25:75:1. Yield 23%. N.m.r. in solvent B: 1.55 (s, 6H), 3.4–3.6 (m, 2H), 3.6–4.1 (m, 2H), 4.4–4.6 (m, 1H), 5.0–5.2 (m, 1H), 5.2 (d, 1H), 5.9 (d, 1H) 7.1 (s, 1H). 26. Reaction carried out for 3 hrs. at room temperature and 1 hr. at 40° C. Eluant proportion 25:75:1. N.m.r. in solvent B: 1.2 (m, 3H), 1.55 (s, 6H), 3.5–3.9 (m, 4H), 3.95 (s, 3H), 4.7 (s, 2H), 5.25 (d, 1H), 5.9 (d, 1H), 7.0 (s, 1H), 7.3–7.7 (m, 1H), 8.2 (d, 1H), 8.65 (d, 1H). 27. Reaction carried out at 40° C. for 1 hr. Eluant proportion 20:80:1. N.m.r. in solvent B: 1.5 (s, 6H), 3.1 (s, 3H), 3.2 (d, 1H), 3.5 (d, 1H), 3.9 (s, 3H), 4.5 (d, 1H), 4.65 (d, 1H), 5.2 (d, 1H), 5.85 (d, 1H), 7.05 (s, 1H), 7.0–7.2 (m, 2H), 8.2–8.4 (m, 2H). 28. The CAZAMCA starting material was obtained as follows:

A solution of 4-chloro-N-methylbutyramide in $CH_2Cl_2$ was treated dropwise with silver fluoroborate in a mixture of $CH_2Cl_2$ and benzene at -20° C., and the reaction was allowed to warm to room temperature. The silver chloride precipitate was filtered off, and the product was purified by silica chromatography, eluting with $CH_2Cl_2$/MeOH, 4:1, to yield N-methyliminobutyrolactone lactone fluoroborate, 71%, which was converted to free base by reaction with 1 eq. of 1,8-diazabicyclo[5,4,0]undec-7-ene (DBU) in $CH_2Cl_2$ (yield 62% of free base). This product was reacted with 7-[2-(2-aminothiazol-4-yl)-2-[(Z)-1-carboxy-1-methylethoxyimino]acetamido]-3-iodomethylceph-3-em-4-carboxylic acid in acetonitrile at room temperature for ½ hr. to give the corresponding 3-[N-(1,2,3,4-tetrahydo-2-furylidene)-N-methylaminomethyl]cephem, which was hydrolysed with 4 eq. of sodium bicarbonate in water at room temperature for ½ hr., and the product purified by preparative HPLC eluting with MeOH/$H_2O$/HOAc, 20:80:1 to yield the required starting material, yield 45%. 29. Reaction carried out in DMF/$H_2O$, 1:1, at 40° C. for 4 hours. Eluant proportion 25:75:1. N.m.r. in solvent B: 1.1 (m, 3H), 1.55 (s, 6H), 2.5 (s, 3H), 3.0–3.7 (m, 4H), 3.8 (s, 3H), 4.6 (s, 2H), 5.2 (d, 1H), 5.9 (d, 1H , 7.0–7.05 (m, 3H), 8.2 (d, 1H). 30. Reaction at room temperature for 1.5 hrs. Eluant proportion 25:75:1. N.m.r in solvent B: 1.6 (s, 6H), 3.2–3.6 (m, 4H), 4.0 (s, 3H), 4.0–4.3 (m, 1H), 4.5–4.8 (m, 2H), 5.0–5.2 (m, 1H), 5.2 (d, 1H), 5.5–6.0 (m, 1H), 5.9 (d, 1H), 7.1 (s, 2H), 7.2 (d, 2H), 8.3 (d, 1H). 31. The precursor CAZAMCA derivative was a mixture of N-allyl and N-propyl, obtained by reductive alkylation of acrylaldehyde, as in Footnote 4, using 1.2 eq. of the aldehyde, and reacting at room temperature for 1 hr. Eluant proportion 20:80:1. This mixture was used to prepare the final product, purification of which separated the N-allyl and N-propyl analogues. 32. Eluant proportion 25:75:1. N.m.r. in solvent B: 0.9 (t, 3H), 1.6 (s, 6H), 3.1–3.8 (m, 4H), 3.9 (s, 3H), 4.5–4.8 (m, 2H), 5.2 (d, 1H), 5.9 (d, 1H), 7.0 (s, 1H), 7.2 (d, 2H), 8.2 (d, 2H). 33. Reacted overnight at room temperature. Eluant proportion 20:80:1. N.m.r. in solvent B: 1.5 (s, 6H), 2.6-3.0 (m, 2H), 3.95 (d, 1H), 3.25 (d, 1H), 3.95 (s, 3H), 4.5-4.8 (m, 2H), 5.2 (d, 1H), 5.9 (d, 1H), 7.0 (s, 1H), 7.4 (d, 2H), 8.4 (d, 2H). 34. The precursor was obtained as in Footnote 4 by Michael addition of acrylonitrile to CAZAMCA The product was purified by HPLC, eluant proportion 15:85:1. Yield 31%. N.m.r. in solvent B: 1.55 (s, 6H), 2.8-3.1 (m, 2H), 3.2-3.4 (m, 2H) 3.5-3.8 (m, 2H), 3.8-4.2 (m, 2H), 5.2 (d, 1H), 5.9 (d, 1H), 7.0 (s, 1H). 35. This compound obtained by reacting the product of Example 67 with formic acetic anhydride in MeOH at room temperature for ½ hr. Eluant proportion 20:80:1. N.m.r in solvent B: 1.55 (s, 6H), 3.2-3.8 (m, 6H), 3.9 (s, 3H), 3.5-3.8 (m, 2H), 5.2 (d, 1H), 5.9 (d, 1H), 7.0 (s, 1H), 7.2 (d, 2H), 8.0 (s,1H), 8.2 (d, 2H).

EXAMPLES 76-87

The appropriate 3-acetoxymethyl-7-[2-(2-aminothiazol-4-yl)-2-(substituted oximino) acetamido]ceph-3-em-4-carboxylic acid and the appropriate amino-substituted quaternary heterocycle were reacted together at 85° C. at pH 7.0-7.5. The pH was maintained with this range by the addition of dilute HOAc or $NaHCO_3$ solution as necessary. The product was purified by preparative HPLC, using a mixture of $MeOH/H_2O$/HOAc as eluant.

The following compounds were prepared:

| Example | $R^{11}$ | R | $R^1$ | Yield | Footnotes |
|---|---|---|---|---|---|
| 76. | Me | H | isoquinolinium-$NCH_3$ | 11 | 1 |
| 77. | Me | H | quinolinium-$CH_3$ | 6 | 2 |
| 78 | —$C(CH_3)_2COOH$ | H | isoquinolinium-$NCH_3$ | 8 | 3 |
| 79 | Me | H | isoquinolinium-$NCH_2CONH_2$ | 7 | 4,5 |
| 80. | Me | Me | isoquinolinium-$NCH_3$ | 31 | 6,7 |
| 81. | —$C(CH_3)_2COOH$ | H | isoquinolinium-$NCH_2CONH_2$ | 6 | 8 |
| 82. | —$C(CH_3)_2COOH$ | H | quinolinium-$CH_3$ | 9 | 9 |

-continued

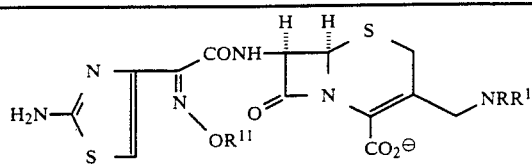

| Example | R[11] | R | R[1] | Yield | Footnotes |
|---|---|---|---|---|---|
| 83. | —C(CH₃)₂COOH | Me | 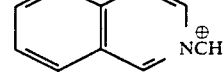 methylisoquinolinium (N⁺CH₃) | 13 | 10 |
| 84. | —C(CH₃)₂COOH | Et | 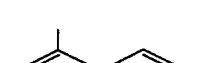 methylisoquinolinium (N⁺CH₃) | 13 | 11,12 |
| 85. | —C(CH₃)₂COOH | —(CH₂)₂NH₂ | 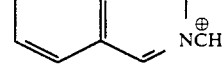 methylisoquinolinium (N⁺CH₃) | 7 | 13,14,15 |
| 86. | —C(CH₃)₂COOH | Et | 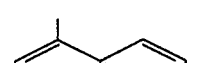 methylquinolinium (N⁺CH₃) | 4 | 16,17 |
| 87. | —C(CH₃)₂COOH | H | 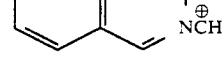 methylquinolinium (N⁺CH₃) | 12 | 18 |

Footnotes 1. Reaction time 3 hrs. Eluant proportion 15-20: 85-80:1. N.m.r. in solvent B: 3.55 (s, 2H), 3.95 (s, 3H), 4.4 (s, 3H), 4.4 (s, 2H), 5.2 (d, 1H), 5.8 (d, 1H), 7.05 (s, 1H), 7.25 (d, 1H), 7.6 (d, 1H), 7.85 (t, 1H), 8.6 (d, 1H), 8.8 (d, 1H), 9.8 (s, 1H). 2. Reaction time 2 hrs. Eluant proportions as in Footnote 1. N.m.r. in solvent B; 3.55 (s, 2H), 4.0 (s, 3H), 4.46 (s, 3H), 4.46 (s, 2H), 5.15 (d, 1H), 5.75 (d, 1H), 7.0 (s, 1H), 7.0 (d, 1H), 7.45 (d, 1H), 7.8-8.05 (m, 2H), 9.3 (d, 1H), 9.5 (d, 1H). 3. Reaction time 2 hrs. Eluant proportion 30-35: 70-65:1. N.m.r. in solvent B: 1.55 (s, 6H), 3.55 (s, 2H), 4.4 (s, 3H), 4.4 (s, 2H), 5.15 (d, 1H), 5.8 (d, 1H), 7.05 (s, 1H), 7.15 (d, 1H), 7.55 (d, 1H), 7.75 (t, 1H), 8.5 (d, 1H), 8.7 (d, 1H), 9.7 (s, 1H). 4. Eluant proportion 20-25: 80-75:1. N.m.r. in solvent B: 3.55 (s, 2H), 3.95 (s, 3H), 4.4 (s, 2H), 5.2 (d, 1H), 5.5 (s, 2H), 5.8 (d, 1H), 7.05 (s, 1H), 7.3 (d, 1H), 7.65 (d, 1H), 7.85 (t, 1H), 8.6 (d, 1H), 8.8 (d, 1H), 9.8 (s, 1H). 5. The 5-amino-2-carbamoylmethylisoquinolinium chloride used as starting material was obtained by alkylation of 5-aminoisoquinoline (1 eq.) with 2-chloroacetamide (1 eq.) in DMF overnight at 45° C. The precipitate was washed with DMF, then CH₂Cl₂, and dried. Yield 76%. N.m.r. in solvent B: 5.45 (s, 2H), 7.4 (dd, 1H), 7.6 (d, 1H), 7.75 (t, 1H), 8.45 (d, 1H), 8.6 (d, 1H), 9.8 (s, 1H). 6. Eluant proportion as in Footnote 4. N.m.r. in solvent B: 2.8 (s, 3H), 3.6 (s, 2H), 4.0 (s, 3H), 4.15 (s, 2H), 4.45 (s, 3H), 5.15 (d, 1H), 5.75 (d, 1H), 7.0 (s, 1H), 7.6-8.1, 8.4-8.6 and 9.6-9.9 (3m, 6H). 7. The 2-methyl-5-methylaminoisoquinolinium iodide used as starting material was obtained by reacting 5-methylaminoisoquinoline with a large excess of methyl iodide at room temperature for 17 hrs. in CH₂Cl₂. The solvents were evaporated to give the required salt. Yield 100%. N.m.r. in solvent B: 4.0 (s, 3H), 4.4 (s, 3H), 7.05 (d, 1H), 7.55 (d, 1H), 7.85 (t, 1H), 8.6 (s, 2H), 9.8 (s, 1H). 8. Reaction time 3 hrs. Eluant proportion 25:75:1. N.m.r. in solvent B: 1.5 (s, 6H), 3.55 (s, 2H), 4.45 (s, 2H), 5.2 (d, 1H), 5.45 (s, 2H), 5.85 (d, 1H), 7.05 (s, 1H), 7.15-7.4 (m, 1H), 7.5-7.9 (m, 2H), 8.3-8.9 (m, 2H), 9.7-9.9 (m, 1H). 9 Eluant proportions 20-25≃30:80-75-70:1. N.m.r. in solvent B; 1.5 (s, 6H), 3.6 (s, 2H), 4.5 (s, 5H), 5.2 (d, 1H), 5.85 (d, 1H), 7.0 (s, 1H), 6.7-7.1 (m, 1H), 7.5 (d, 1H), 7.8-8.1 (m, 2H), 9.3-9.6 (m, 2H). 10. Eluant proportion 20-30:80-70:1. N.m.r. in solvent B: 1.5 (s, 6H), 2.8 (s, 3H), 3.55 (s, 2H), 4.4 (s, 2H), 4.45 (s, 3H), 5.1 (d, 1H), 5.8 (d, 1H), 7.05 (s, 1H), 7.0-7.2, 7.6-8.2, 8.4-8.6, and 9.6-10.0 (4×m, 6H). 11. Eluant proportion 25-30:-75-70:1. N.m.r. in solvent B: 0.9 (t, 3H, 1.55 (s, 6H), 3.2 (q, 2H), 3.55 (s, 2H), 4.4 (s, 2H), 4.45 (s, 3H), 5.05 (d, 1H), 5.75 (d, 1H), 7.0 (s, 1H), 7.0-7.2, 7.6-8.2, 8.4-8.6 and 9.6-10.0 (4×m, 6H). 12. The 5-ethylamino-1-methylisoquinolinium iodide was prepared by the process described in Footnote 7. N.m.r. in solvent B: 1.3 (t, 3H), 3.3 (q, 2H), 4.4 (s, 3H), 7.1 (d, 1H), 7.55 (d, 1H), 7.8

(t, 1H), 8.6 (d, 1H), 8.65 (d, 1H), 9.75 (s, 1H). 13. The quaternary heterocycle used as starting material was 5-(2-Boc-aminoethylamino)-2-methylisoquinolinium methosulphate. Reaction time 2.5 hrs. Eluant proportion 30-40:70-60:1. N.m.r. in solvent B: 1.3 (s, 9H), 1.55 (s, 6H), 3.1-3.5 (m, 4H), 3.55 (s, 2H), 4.4 (s, 2H), 4.45 (s, 3H), 5.05 (d, 1H), 5.75 (d, 1H), 7.0 (s, 1H), 7.0-7.2, 7.6-8.2, 8.4-8.6 and 9.6-10.0 (4×m, 6H). 14. The product was deprotected by dissolving in CH₂Cl₂/TFA (1:2) for 10 minutes at room temperature. N.m.r. in solvent B: 1.55 (s, 6H), 2.9-3.5 (m 4H), 3.55 (s, 2H), 4.4 (s, 2H), 4.45 (s, 3H), 5.05 (d, 1H), 5.75 (d, 1H), 7.0 (s, 1H), 7.0-7.2, 7.6-8.2, 8.4-8.6 and 9.6-10.0 (4×m, 6H). 15. The 5-(2-Boc-aminoethylamino)-2-methylisoquinolinium methosulphate starting material was prepared as follows: 5-Hydroxyisoquinoline (1 eg.) and ethylene diamine (10 eq.), were reacted in a Bucherer reaction, in water with sodium hydrogen sulphite (2 eq.) at 160° C. for 20 hrs. The product was purified by chromatography on silica, eluting with CH₂Cl₂/MeOH, 97-90: 3-10. Yield 26%. N.m.r. in d₆-DMSO: 2.9 (t, 2H), 3.2 (dt, 2H), 6.3 (t, 1H), 6.75 (dd, 1H), 7.25 (d, 1H), 7.45 (t, 1H), 8.05 (d, 1H), 8.4 (d, 1H), 9.15 (s, 1H).

The Boc derivative was formed by reacting the above product with 0,0¹-di-tert-butyl carbonic anhydride (1.5 eq.) in THF for 1 hr. The Boc compound was purified by chromatography on silica, eluting with ether. Yield 66%. N.m.r. in CDCl₃: 1.45 (s, 9H), 3.2-3.7 (m, 4H), 4.8-5.1 (m, 1H), 5.3-5.6 (m, 1H), 6.7 (dd, 1H), 7.3 (d, 1H), 7.45 (t, 1H), 7.65 (d, 1H), 8.45 (d, 1H), 9.15 (s, 1H).

This Boc product was quaternised with dimethyl sulphate, in CH₂Cl₂ at room temperature for 2 hrs. The solvent was evaporated, and the residue was washed with ether. N.m.r in CDCl₃; 1.45 (s, 9H), 3.2 (m, 2H), 3.55 (m, 2H), 3.8 (s, 6H), 4.5 (s, 3H), 6.7 (d, 1H), 7.3 (d, 1H), 7.55 (t, 1H), 8.1 (d, 1H), 8.5 (d, 1H), 9.5 (s, 1H). 16. Eluant proportion as in Footnote 11. N.m.r. in solvent B: 0.95 (t, 3H), 1.55 (s, 6H), 3.25 (q, 2H), 3.6 (s, 2H), 4.4 (s, 2H), 4.6 (s, 3H), 5.05 (d, 1H), 5.8 (d, 1H), 7.0 (s, 1H), 7.2-7.5, 7.8-8.2, 9.2-9.5 (3×m, 6H). 17. The 5-ethylamino-1-methylquinolinium iodide used as starting material obtained by the process described in Footnote 7, starting from 5-ethylaminoquinoline, 72 hrs at room temperature. Yield 100%. N.m.r. in solvent B: 1.3 (t, 3H), 3.35 (q, 2H) 4.5 (s, 3H), 6.85 (d, 1H), 7.35 (d, 1H), 7.7-8.1 (m, 2H), 9.25 (d, 1H), 9.45 (d, 1H). 18. Eluant proportion as in Footnote 10. N.m.r. in solvent B: 1.55 (s, 6H), 3.55 (s, 2H), 4.3 (s, 2H), 4.5 (s, 3H), 5.2 (d, 1H), 5.85 (d, 1H), 7.0 (s, 1H), 7.2 (d, 1H); 7.6 (dd, 1H), 7.8 (dd, 1H), 8.15 (d, 1H), 8.6 (d, 1H), 8.85 (d, 1H).

EXAMPLES 88-106

The appropriate quaternary chloro-heterocycle (1 eq.) was reacted with 3-aminomethyl 7-[2-(2-aminothiazol-4-yl)-2-[(Z)-1-carboxy-1-methylethoxyimino)-acetamido]ceph-3-em-4-carboxylic acid (1 eq.) in DMF/H₂O (2:1). The solvents were evaporated and the residue was purified by HPLC, eluting with a mixture of MeOH/H₂O/HOAc. The following compounds were prepared:

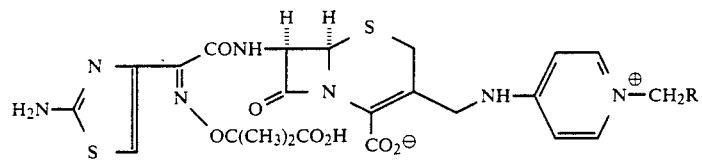

| Example | R | Yield | Footnotes |
|---|---|---|---|
| 88 | ![thiazole-guanidine] | 33 | 1,2,38 |
| 89. | ![dihydropyrimidinedione] | 23 | 3,4,38 |
| 90. | ![phthalimide] | 18 | 5,6,38 |
| 91. | ![aminocyanopyrazine N-oxide] | 26 | 7,8,38 |

-continued
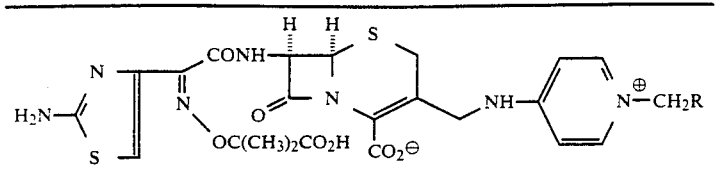
| Example | R | Yield | Footnotes |
|---|---|---|---|
| 92. | -CH₂-N with imidazo-pyrimidinedione (NCH₃, N-CH₃) | 35 | 9,10,38 |
| 93. | thiazole-CH₃ | 40 | 11,12,38 |
| 94. | thiazole-CO₂C₂H₅ | 28 | 13,14,38 |
| 95. | thiazole-CONH₂ | 40 | 15,16,38 |
| 96. | thiazole-CN | 45 | 17,18,38 |
| 97. | thiadiazole | 44 | 19,20,38 |
| 98. | thiazole-NH·CHO | 15 | 21,22,38 |
| 99. | thiazole-NH₂ | 14 | 23,24,38 |
| 100. | benzimidazole (NH) | 21 | 25,26,38 |
| 101. | -CH₂- with HN-C(O)-phenyl-O | 36 | 27,28,38 |
| 102. | imidazole-N-CH₃ | 35 | 29,30,38 |
| 103. | imidazole-NH | 37 | 31,32,38 |

-continued

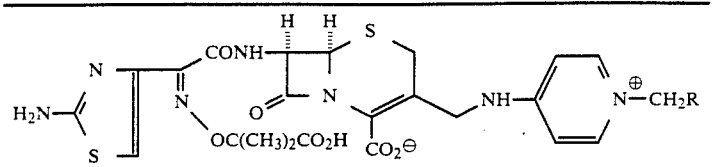

| Example | R | Yield | Footnotes |
|---|---|---|---|
| 104. | (thiophene) | 32 | 33,34,38 |
| 105. | 2-methyl-5-nitrobenzimidazolyl | 17 | 35,36,38 |
| 106. | 2-methyl-5-aminobenzimidazolyl | 21 | 37,38 |

Footnotes 1. Reaction time 3 hrs. at room temperature. Eluant proportion 20:80:1. N.m.r. in solvent B: 1.55 (s, 6H), 3.4 (d, 1H), 3.7 (d, 1H), 4.35 (s, 2H), 5.2 (d, 1H), 5.3 (s, 2H), 5.85 (d, 1H), 7.05 (s, 1H), 6.9-7.2 and 8.2-8.6 (2×m, 4H). 2. The starting pyridinium salt was obtained by condensation of 4-methylthiopyridine and 4-chloromethyl-2-guanidinothiazole hydrochloride in EtOH/DMF (5:1) under reflux overnight. The product was purified by silica chromatography, eluting with $CH_2Cl_2$/MeOH, 100-70:0-30. Yield 20%. N.m.r. in solvent B: 2.65 (s, 3H), 5.65 (s, 2H), 7.55 (s, 1H), 7.85 and 8.9 (2×d, 4H). 3. Reaction time 1 hr. at room temperature. Eluant proportion as in Footnote 1. N.m.r. in solvent B: 1.55 (s, 6H), 3.45 (d, 1H) 3.75 (d, 1H), 4.4 (s, 2H), 5.1 (s, 2H), 5.25 (d, 1H), 5.9 (d, 1H), 5.3 (s, 1H), 7.1 (s, 1H), 7.0-7.3 (m, 2H), 8.1-8.5 (m, 2H). 4. The starting pyridinium salt was obtained by the process in Footnote 2, by alkylating 4-methylsulphonylpyrimidine with 6-chloromethyluracil. Yield 47%. N.m.r. in solvent B: 2.7 (s, 3H), 5.4 (s, 3H), 7.9 (d, 2H), 8.7 (d, 2H). 5. Reaction time 2.5 hrs. at room temperature. Eluant proportion 30:70:1. N.m.r. in solvent B: 1.55 (s, 6H), 3.55 (s, 2H), 4.4 (s, 2H), 5.2 (d, 1H), 5.9 (d, 1H), 6.0 (s, 2H), 6.9-7.2 (m, 2H), 7.1 (s, 1H), 7.95 (s, 4H), 8.1-8.5 (m, 2H). 6. The starting pyridinium salt was obtained by the process of Footnote 2. Yield 30%. N.m.r. in solvent B: 2.65 (s, 3H), 6.25 (s, 2H), 7.9 (s, 4H), 7.9 and 8.7 (2×d, 4H). 7. Reaction as Footnote 3. N.m.r. in solvent B: 1.6 (s, 6H), 3.6 (s, 2H), 4.4 (s, 2H), 5.3 (d, 1H), 5.4 (s, 2H), 5.95 (d, 1H), 7.1 (s, 1H), 7.0-7.3 (m, 2H), 8.2-8.6 (m, 2H), 8.85 (s, 1H). 8. The starting pyridinium salt was obtained by the process of Footnote 2, carried out at room temperature for 40 hrs. Yield 81%. N.m.r. in solvent B: 2.7 (s, 3H), 5.65 (s, 2H), 7.95 (d, 2H), 8.8 (d, 2H), 8.8 (s, 1H). 9. Reaction time 2 hrs. Eluant proportion 25:75:1. N.m.r. in solvent B: 1.55 (s, 6H), 3.25 (s, 3H), 3.45 (s, 3H), 3.55 (s, 2H), 4.35 (s, 2H), 4.7 (s, 4H), 5.25 (d, 1H), 5.9 (d, 1H), 7.0 (s, 1H), 6.8-7.2 (m, 2H), 7.8 (s, 1H), 7.9-8.3 (m, 2H). 10. The starting pyridinium salt was obtained by the process of Footnote 2. Yield 46%. N.m.r. in solvent B: 2.7 (s, 3H), 3.2 (s, 3H), 3.45 (s, 3H), 4.85 (s, 4H), 7.85 (s, 1H), 7.95 (d, 2H), 8.5 (d, 2H). 11. Reaction time 1.5 hrs. at room temperature, using a 50% excess of the pyridinium salt. Eluant proportion 30:70:1. N.m.r. in solvent B: 1.55 (s, 6H), 2.55 (s, 3H), 3.4 (d, 1H), 3.7 (d, 1H), 4.35 (s, 2H), 5.25 (d, 1H), 5.9 (d, 1H), 5.45 (s, 2H), 7.05 (s, 1H), 7.55 (s, 1H), 6.9-7.2 (m, 2H), 8.2-8.6 (m, 2H). 12. The starting pyridinium salt was obtained by the process of Footnote 2, in EtOH as solvent. Yield 19%. Nmr in solvent B: 2.6 (s, 3H), 2.7 (s, 3H), 5.75 (s, 2H), 7.75 (s, 1H), 7.95 (d, 2H), 8.8 (d, 2H). 13. Reaction time 1.5 hrs. at room temperature. Eluant proportion 30:70:1. N.m.r. in solvent B: 1.3 (t, 3H), 1.55 (s, 6H), 3.4 (d, 1H), 3.7 (d, 1H), 4.35 (s, 2H), 4.4 (q, 2H), 5.25 (d, 1H), 5.9 (d, 1H), 5.6 (s, 2H), 7.15 (s, 1H), 6.9-7.2 (m, 2H), 8.25 (s, 1H), 8.2-8.6 (m, 2H). 14. The starting pyridinium salt was obtained by the process of Footnote 2. Yield 70%. N.m.r. in solvent B: 1.3 (t, 3H), 2.65 (s, 3H), 4.35 (q, 2H), 5.86 (s, 2H), 7.9 (d, 2H), 8.25 (s, 1H), 8.8 (d, 2H). 15. Reaction time 2 hrs. at room temperature. Eluant proportion as Footnote 1. N.m.r. in solvent B: 1.55 (s, 6H), 3.4 (d, 1H), 3.7 (d, 1H), 4.35 (s, 2H), 5.2 (d, 1H), 5.5 (s, 2H), 5.85 (d, 1H), 7.1 (s, 1H) 6.9-7.2 (m, 2H), 8.05 (s, 1H), 8.1-8.4 (m, 2H). 16. The starting pyridinium salt was obtained by the process of Footnote 2. Yield 18%. N.m.r. in solvent B: 2.75 (s, 3H), 5.9 (s, 2H), 7.8 (d, 2H), 8.25 (s, 1H), 8.85 (d, 2H). 17. Reaction time ½ hr. at room temperature. Eluant proportion as Footnote 5. N.m.r. in solvent B: 1.55 (s, 6H), 3.4 (d, 1H), 3.7 (d, 1H), 4.25 (d, 1H), 4.5 (d, 1H), 5.2 (d, 1H), 5.6 (s, 2H), 5.9 (d, 1H), 7.05 (s, 1H), 7.0-7.2 (m, 2H), 8.4 (s, 1H), 8.2-8.6 (m. 2H). 18. The starting pyridinium salt is obtained by the process of Footnote 2. Yield 90%. N.m.r. in solvent B: 2.7 (s, 3H), 5.9 (s, 2H), 8.05 (d, 2H), 8.45 (s, 1H), 8.8 (d, 2H). 19. Reaction time 2 hrs. at room temperature. Eluant proportion as Footnote 2. N.m.r. in solvent B; 1.55 (s, 6H), 3.4 (d, 1H), 3.7 (d, 1H), 4.25 (d, 1H), 4.5 (d, 1H), 5.25 (d, 1H), 5.9 (d, 1H), 5.95 (s, 2H), 7.15 (s, 1H), 6.9-7.2 (d, 2H), 8.3-8.7 (d, 2H), 9.4 (s, 1H). 20. The starting pyridinium salt was obtained by the process of Footnote 2, but for 48 hrs. at room temperature. Yield 48%. N.m.r. in solvent B: 2.55 (s, 3H), 2.7 (s, 3H), 6.25 (s, 2H), 7.95 (d, 2H), 8.95 (d, 2H), 9.45 (s, 1H). 21. Reaction time 3.5 hrs. at room temperature. Eluant proportion 20-30:80-70:1. N.m.r. in solvent B: 1.55 (s, 6H), 3.4 (d, 1H), 3.7 (d, 1H), 4.4 (s, 2H), 5.25 (d, 1H), 5.4 (s, 1H), 5.9 (d, 1H), 7.15 (s, 1H), 6.9-7.2 (m, 2H), 7.35 (s, 1H), 8.55 (s, 1H), 8.2-8.6 (m, 2H). 22. The starting pyridinium salt was obtained by the process of Footnote 2. Yield 39%. N.m.r. in solvent B: 2.7 (s, 3H), 5.7 (s, 2H), 7.4 (s, 1H), 7.95 (d, 2H), 8.5 (s, 1H), 8.8 (d, 2H). 23. The 3-aminomethyl cephem was alkylated with the corresponding 2-(Boc-amino)thiazole derivative, at room temperature for 40 minutes. The Boc protecting group was removed by dissolving the product in TFA/CH$_2$Cl$_2$ (4:1) at room temperature for 50 minutes. Eluant proportion 30-35: 70-65:1. N.m.r. in solvent B: 1.55 (s, 6H), 3.4 (d, 1H), 3.7 (d, 1H), 4.4 (s, 2H), 5.2 (s, 2H), 5.25 (d, 1H), 5.9 (d, 1H), 7.05 (s, 1H), 6.9-7.2 (m, 2H), 8.0-8.4 (m, 2H). 24. The starting Boc-aminochloromethylthiazole was obtained by the process of Footnote 2. Yield 65%. N.m.r. in solvent B; 1.45 (s, 9H), 2.7 (s, 3H), 5.7 (s, 2H), 7.35 (s, 1H), 7.9 (d, 2H), 8.75 (d, 2H). 25. Reaction time 1.25 hrs. at room temperature. Eluant proportion 30-40: 70-60:1. N.m.r. in solvent B: 1.5 (s, 6H), 3.4 (d, 1H), 3.7 (d, 1H), 4.25 (d, 1h), 4.5 (d, 1H), 5.15 (d, 1H), 5.85 (d, 1H), 6.0 (s, 2H), 7.1 (s, 1H), 7.0-7.2 (m, 2H), 7.5-7.7 (m, 2H), 7.7-7.9 (m, 2H), 8.2-8.6 (m, 2H). 26. The starting pyridinium salt was obtained by the process of Footnote 2, at room temperature overnight followed by 3 hrs. under reflux in EtOH/DMF (3 2). The solvent was evaporated, and the product was precipitated with ether. Yield 54%. N.m.r. in solvent B: 2.7 (s, 3H), 6.35 (s, 2H), 7.55 (m, 2H), 7.75 (m, 2H), 8.0 (d, 2H), 8.9 (d, 2H). 27. Reaction time 40 minutes at room temperature. Eluant proportion as Footnote 1. N.m.r. in solvent B: 1.55 (s, 6H), 2.4 (dt, 2H), 3.4 (d, 1H), 3.7 (d, 1H), 4.4 (m, 4H), 5.2 (d, 1H), 5.5 (t, 1H),5.9 (d, 1H), 6.9 (d, 1H), 7.1 (s, 1H), 7.0-7.2 (m, 2H), 7.15 (t, 1H), 7.55 (dt, 1H), 7.9 (dd, 1H), 8.2-8.6 (m, 2H). 28. The starting pyridinium salt was obtained by the process of Footnote 2, at room temperature overnight followed by 24 hrs. under reflux. Yield 20%. N.m.r. in solvent B: 2.5 (dt, 2H), 2.7 (s, 3H), 4.7 (t, 2H), 5.5 (t, 1H), 6.9 (d, 1H), 7.15 (t, 1H), 7.55 (dt, 1H), 7.9 (dd, 1H), 8.0 (d, 2H), 8.9 (d, 2H). 29. Reaction time 2 hrs. at room temperature. Eluant proportion 10-25: 90-75:1. N.m.r. in solvent B: 1.55 (s, 6H), 3.4 (d, 1H), 3.7 (d, 1H), 3.9 (s, 3H), 4.4 (s, 2H), 5.2 (d, 1H), 5.85 (d, 1H), 5.85 (s, 2H), 7.0 (s, 1H), 7.7 (d, 1H), 7.75 (d, 1h), 7.0-7.4 (m, 2H), 8.2-8.6 (m, 2H). 30. The starting pyridinium salt was obtained by the process of Footnote 2, at room temperature for 96 hrs. Yield 30%. N.m.r. in solvent B: 2.7 (s, 3H), 3.95 (s, 3H), 6.2 (s, 2H), 7.7 (d, 1H), 7.75 (d, 1H), 7.95 (d, 1H), 8.85 (d, 1H). 31. Reaction time 3 hrs. room temperature. Eluant proportion 10-20:90-80:1. N.m.r. in solvent B: 1.55 (s, 6H), 3.4 (d, 1H), 3.7 (d, 1H), 4.4 (s, 2H), 5.2 (d, 1H), 5.75 (s, 2H), 5.85 (d, 1H), 7.05 (s, 1H), 7.65 (s, 2H), 7.0-7.3 (m, 2H), 8.2-8.4 (m, 2H). 32. The starting pyridinium salt was obtained by the process of Footnote 2. Yield 83%. N.m.r. in solvent B: 2.75 (s, 3H), 6.15 (s, 2H), 7.75 (s, 2H), 8.05 (d, 2H), 8.85 (d, 2H). 33. Reaction time 1.5 hrs. at room temperature. Eluant proportion as Footnote 1. N.m.r. in solvent B: 1.5 (s, 6H), 3.4 (d, 1H), 3.7 (d, 1H), 4.4 (s, 2H), 5.15 (d, 1H), 5.55 (s, 2H), 5.85 (d, 1H), 7.05 (s, 1H), 7.05 (dd, 1H), 7.0-7.2 (m, 2H), 7.4 (d, 1H), 7.55 (d, 1H), 8.2-8.6 (m, 2H). 34. The starting pyridinium salt was obtained by the process of Footnote 2, at room temperature overnight followed by 4 hrs. under reflux. Yield 46%. N.m.r. in solvent B: 2.65 (s, 3H), 5.9 (s, 2H), 7.05 (dd, 1H), 7.4 (d, 1H), 7.55 (d, 1H), 7.85 (d, 2H), 8.8 (d, 2H). 35. Reaction time 3 hrs. at room temperature. Eluant proportion 40-50: 60-50:1. N.m.r. in solvent B: 1.55 (s, 6H), 3.4 (d, 1H), 3.7 (d, 1H), 4.3 (d, 1H), 4.5 (d, 1H), 5.2 (d, 1H), 5.85 (d, 1H), 5.9 (d, 1H), 7.05 (s, 1H), 7.0-7.3 (m, 2H), 7.7 (d, 1H), 8.1 (dd, 1H), 8.5 (d, 1H), 8.2-8.6 (m, 2H). 36. The starting pyridinium salt was obtained by the process of Footnote 2, heating under reflux for 6 hrs., then overnight at room temperature. Yield 77%. N.m.r. in solvent B: 2.7 (s, 3H), 6.1 (s, 2H), 7.7 (d, 1H), 7.95 (d, 2H), 8.1 (dd, 1H), 8.5 (d, 1H), 8.85 (d, 2H). 37. This compound obtained by reduction of the product of Example 105 with titanium trichloride (5 eq.) in MeOH/TFA (99:1) for 1 hr. at room temperature. Eluant proportion as Footnote 1. N.m.r. in solvent B: 1.55 (s, 6H), 3.4 (d, 1H), 3.7 (d, 1H), 4.3 (d, 1H), 4.5 (d, 1H), 5.2 (d, 1H), 5.9 (d, 1H), 5.9 (s, 2H), 7.1 (s, 1H), 7.0-7.3 (m, 2H), 7.44 (d, 1H , 7.85 (dd, 1H), 7.9 (d, 1H) 8.2-8.6 (m, 2H). 38. The quaternised thiomethyl heterocycle salt was oxidised with MCPBA in CH$_2$Cl$_2$ containing a catalytic amount of TFA at 0° C. to room temperature for up to 4 hours, to give the corresponding sulphinyl compound, often also containing sulphone and sulphide, but not further purified.

EXAMPLE 107

An activated ester was prepared from (2-aminothiazol-4-yl)-(2-methoxyimino)acetic acid (1.1 eq.) by reaction with hydroxybenzotriazole (1.1 eq.) and N,N'-dicyclohexylcarbodi-imide (1.1 eq.) in DMF, at room temperature for 2 hrs. To this ester was added a solution of 7-amino-3-[N-ethyl-N-(1-methyl-4-pyridinio)aminomethyl]ceph-3-em-4-carboxylate (1.0 eq.) in DMF and Et$_3$N (2 eq. . The reaction mixture was stirred at room temperature for 2 hrs. and filtered, and the solvents were evaporated. The product, 7-[2-(2-aminothiazol-4-yl)-2-(methoxyimino)acetamido]-3-(N-ethyl)-[N-(1-methylpyridinio)]aminomethylceph-3-em-4-carboxylate, was purified by preparative HPLC eluting with MeOH/H$_2$O/ HOAc, 10:90:1. N.m.r. in solvent B: 1.0-1.3 (m, 3H), 3.0-3.8 (m, 4H), 3.9 (s, 3H), 3.95 (s, 3H), 4.5-4.7 (m, 2H), 5.2 (d, 1H), 5.8 (d, 1H), 7.0 (s, 1H), 7.15 (d, 2H), 8.2 (d, 2H).

The cephem starting material was obtained as follows:

3-Aminomethyl-7-(Boc-amino)ceph-3-em-4-carboxylic acid (1 eq.) was dissolved in MeOH, with Et$_3$N (1 eq.) and NaBH$_3$CN (1 eq.) at room temperature. Acetaldehyde (1 eq.) was added over 15 minutes at room temperature, the solvent was evaporated, and the product, 7-(Boc amino)-3-ethylaminomethylceph-3-em-4-carboxylic acid, was purified by preparative HPLC, eluting with MeOH/H$_2$O/HOAc, 30:70:1. Yield 59%, contaminated with some disubstituted material.

The above product (1 eq.) was treated DMF/H$_2$O (3:2) with 4-chloro-1-methylpyridinium iodide (1 eq.) in presence of NaHCO$_3$ (3 eq.). After 2 hrs. at room temperature, the solvents were evaporated and the product was purified by preparative HPLC, eluting with MeOH/H$_2$O/HOAc, 30:70:1. Yield 20%. N.m.r. in d$_6$-DMSO: 1.0-1.2 (m, 3H , 1.4 (s, 9H), 2.8-3.8 (m, 4H), 3.9 (s, 3H), 4.2-4.8 (m, 2H), 4.9 (d, 1H), 5.2 (dd, 1H), 7.7 (d, 2H), 8.2 (d, 2H).

The above product was deprotected by dissolving in TFA and leaving for ½ hr. at room temperature. The TFA was evaporated, the residue triturated with ether to give,the required starting material. Yield 84%. N.m.r. in solvent B: 0.9-1.3 (m, 3H), 3.2-3.8 (m, 4H), 3.9 (s, 3H), 4.5-4.8 (m, 2H), 5.2 (s, 2H), 7.15 (d, 2H), 8.25 (d, 2H).

EXAMPLES 108-115

Method A

The appropriate quaternised heterocyclic starting material (0.28 mM) dissolved in a mixture of CH$_3$CN/H$_2$O (1:1; 2 ml was added to a stirred solution of 3-ethylaminomethyl-7-[2-(2-aminothiazol-4-yl)-(Z)-2-(1-carboxycyclobut-1-yloxyimino)acetamido]ceph-3-em-4-carboxylic acid (0.28 mM) in CH$_3$CN/H$_2$O (1:1; 3 ml) at room temperature under an atmosphere of argon. Sodium bicarbonate (1.14 mM) was added to the reaction mixture which was stirred for 5 hr. and then poured into water (100 ml). The resulting solution was adjusted to pH 3.5 with acetic acid and then concentrated by rotary evaporation under vacuum at 20° C. The resulting aqueous solution was filtered and then diluted with water (100 ml) before loading on to an HP20SS column (20 mm×350 mm). The product was eluted from the resin by increasing amounts of CH$_3$CN in H$_2$O. Fractions containing the required product were combined and concentrated in vacuo and the aqueous residues freeze dried to give lyophilized solids.

Method B

The appropriate quaternised heterocyclic starting material (0.29 mM) in dimethylformamide (2 ml) was added at room temperature to a stirred solution of the N-ethylaminocephem-carboxylic acid of Method A (0.28 mM) in DMF (3 ml.). Triethylamine (0.56 mM) was then added to the mixture and the reaction was allowed to continue for 16 hr. The mixture was then poured into water (100 ml) and the pH adjusted to 3.5 with acetic acid. After filtering, the solution was applied to an HP20SS column (20 mm×350 mm) and the product was eluted with increasing amounts of CH$_3$CN in H$_2$O. The fractions containing the required product were pooled and concentrated by rotary evaporation at 20° C. to give an aqueous concentrate which was then freeze dried.

Using these general processes the following compounds were prepared:

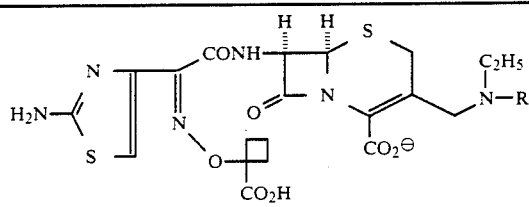

| Example | R | Yield % | Method | Footnotes |
|---------|---|---------|--------|-----------|
| 108 | ![structure with N-N⊕, N-N, CH3] | 14 | A | 1,2 |
| 109 | ![structure with N-N⊕, CH3] | 31 | A | 3,4 |
| 110 | ![structure with N, N, S, ⊕CH3] | 42 | B | 5,6 |
| 111 | ![structure with N, S, N⊕] | 44 | B | 7,8 |
| 112 | ![pyridinium with CH2CH=CHCl] | 37 | A | 9,10 |
| 113 | ![pyridinium-NCH2-C6H4-SO2N(CH3)2] | 16 | B | 11,12 |

The same general processes were also utilized with the corresponding aminomethyl intermediate to synthesize the following unalkylated 3-aminomethyl derivatives:

| Example | R | Yield % | Method | Footnotes |
|---|---|---|---|---|
| 114 | (pyridazine fused with N-methyl imidazolium ring) | 19 | B | 13, 14 |
| 115 | (thieno-pyridinium with N-CH3) | 25 | A | 15, 16 |

Footnotes
1. The starting material was 6-chloro-1-methyl-1,2,4-triazolo[4,3-b]pyridazinium iodide.
2. n.m.r. in solvent A: 9.62 (s, 1H); 8.48 (d, 1H); 8.15 (m, 1H); 6.73 (s, 1H); 5.70 (d, 1H); 5.03 (d, 1H); 4.6 (m, 2H); 4.14 (s, 3H); 3.5–3.8 (m, 2H); 3.15–3.5 (ABq, 2H); 2.15–2.80 (m, 6H); 1.05–1.25 (m, 3H).
3. The starting material was 3-chloro-1-methylpyridazinium iodide.
4. n.m.r. in solvent A: 8.95 (m, 1H); 8.05 (m, 2H); 6.72 (s, 1H); 5.75 (d, 1H); 5.08 (d, 1H); 4.45–4.80 (ABq, 2H); 4.30 (s, 1H); 3.56–3.75 (m, 2H); 3.20–3.55 (ABq, 2H); 2.20–2.60 (m, 6H); 1.05–1.30 (m, 3H).
5. The starting material was 1-methyl-4-methylthiothieno[2,3-d]pyrimidine tetrafluoroborate.
6. n.m.r. in solvent A: 8.86 (s, 1H); 7.93 (d, 1H); 7.80 (d, 1H); 6.74 (s, 1H); 5.79 (d, 1H); 5.11 (d, 1H); 4.74–5.39 (ABq, 2H); 4.02 (m, 5H); 3.15–3.59 (ABq, 2H); 2.20–2.48 (m, 6H); 1.20–1.42 (m, 3H).
7. The starting material was 2,3-dihydro-7-methylthiothiazolo[2,3-a]pyrimidinium tetrafluoroborate.
8. n.m.r. in solvent A: 8.3 (m, 1H); 6.90–7.4 (m, 1H); 6.74 (s, 1H); 5.75 (m, 1H); 5.05 (m, 1H); 4.65–5.0 (ABq, 2H); 4.50–4.65 (m, 2H); 3.75–3.95 (m, 2H); 3.55–3.75 (t, 2H); 3.0–3.55 (ABq, 2H), 2.20–2.5 (m, 6H); 1.1 (t, 3H).
9. Prepared using 4-chloro-1-(trans-3-chloroalkyl)pyridinium tosylate as starting material (see Example 151, Footnote 38) and method A, except that: DMF was used instead of CH$_3$CN and the reaction was worked up by adjusting the pH to 7 with HOAc, concentrating to dryness under vacuum at 20° and redissolving in water prior to HP20SS chromatography.
10. n.m.r. in solvent A: 8.22 (d, 2H); 7.51 (m, 1H); 7.10 (m, 1H); 6.75 (s, 1H); 6.73 (d, 1H); 6.25 (m, 1H); 5.73 (d, 1H); 5.07 (d, 1H); 4.81 (d, 2H); 4.73, 4.49 (ABq, 2H); 3.65 (m, 2H); 3.45, 3.13 (ABq, 2H); 2.36 (m, 4H); 1.86 (m, 2H)); 1.12 (t, 3H).
11. The starting material was 1-(4-dimethylaminosulphonylbenzyl)-4-methanesulphinyl pyridinium tetrafluoroborate, which was obtained as follows:

4-Dimethylsulphamoylbenzyl bromide (0.005M) was mixed with 4-methylthiopyridine (0.005M) and reacted exothermically, and was then left to stand overnight. The product was dissolved in CH$_2$Cl$_2$, and after standing for 3 hrs. was added dropwise to rapidly stirred ether to precipitate 1-(4-dimethylsulphamoylbenzyl)-4-methylthiopyridinium bromide, which was converted to the corresponding tetrafluoroborate salt with silver tetrafluoroborate.

The pyridinium tetrafluoroborate (1.34 mM) was dissolved in CH$_2$Cl$_2$ (15 ml) and treated at 0° with sufficient TFA to obtain a solution, then MCPBA (1.34 mM) was added. The mixture was stirred at 0° for 15 minutes then at room temperature for 4 hrs., and the product was precipitated by the dropwise addition of ether to give 1-(4-dimethylsulphamoyl)benzyl-4-methylsulphinylpyridinium tetrafluoroborate; the required starting material.
12. n.m.r. in solvent A: 8.31 (m, 2H); 7.3–7.90 (m, 6H); 7.08 (m, 1H); 6.73 (s, 1H), 5.76 (d, 1H); 5.48 (s, 2H); 5.06 (d, 1H); 4.35–4.85 (m, 2H), 3.40–3.80 (m, 2H); 3.10–3.44 (ABq, 2H); 2.56 (s, 6H); 2.10–2.50 (m, 6H); 1.0–1.25 (m, 3H).
13. See Footnote 1.
14. n.m.r. in solvent A: 9.65 (s, 1H); 8.35 (d, 1H); 7.51 (d, 1H); 6.76 (s, 1H); 5.80 (d, 1H); 5.08 (d, 1H); 4.05–4.50 (ABq, 2H); 4.17 (s, 3H); 3.36–3.76 (ABq, 2H), 2.20–2.47 (m, 6H)
15. See Footnote 5.
16. n.m.r. in solvent A: 8.85 (s, 1H); 7.90 (m, 1H); 6.75 (s, 1H); 5.81 (d, 1H); 5.08 (d, 1H); 4.46–4.95 (ABq, 2H); 4.04 (s, 3H); 3.30–3.70 (ABq, 2H); 2.17–2.46 (m, 6H).

The 3-ethylaminomethyl-7-[2-(2-aminothiazol-4-yl)-(Z)-2-(1-carboxycyclobut-1-yloxyimino)acetamido]-ceph-3-em-4-carboxylic acid used as starting material was prepared as follows:

3-aminomethyl-7-[2-(2-aminothiazol-4-yl)-(Z)-2-(1-carboxycyclobut-1-yloxyimino)acetamido]ceph-3-em-4-carboxylic acid (10 g; 2.016×10$^{-2}$ mole) was stirred in MeOH (1.0 l.) and to this mixture was added triethylamine (2.8 ml; 2.016×10$^{-2}$ mole) dropwise, which resulted in a clear solution. Sodium cyanoborohydride (1.266 g; 2.016×10$^{-2}$ mole) was added in one portion to the above solution followed by 8 g of activated molecular sieves (4A). A solution of acetaldehyde (1.125 ml in 75 ml methanol) was added to the reaction mixture, under an argon atmosphere, over a period of 40 minutes using an infusion pump and the status of the ensuing reaction was monitored by HPLC (Spherisorb 50DS, 4 mm×30 cm; MeOH/H$_2$O/TFA (40:60:0.2 by volume), 2 ml/min flow rate and monitoring by u.v. at 270 nm). Reaction was continued for 1 hr., the mixture was then filtered, and the filtrate was concentrated to dryness on a rotary evaporator under high vacuum. The residue was dissolved in water (100 ml) and loaded onto an HP20 macroreticular resin (3 l.) previously equilibrated with 0.2% TFA in water. The column was washed with 0.2% TFA in water (2 l.) and then water (5 l.) followed by increasing amounts of CH$_3$CN in water. Fractions (2 l.) were collected and the desired product eluted with 15% CH$_3$CN/H$_2$O. Fractions (21–23) containing the required product were pooled, and concentrated on a rotary evaporator under high vacuum to give a clear solution (100 ml) which was freeze dried to yield 3 g lyophilised solid. Further fractions containing less pure amounts of the required product were also combined and concentrated to give a crude sample (2 g) of the N-ethyl derivative. This crude sample was purified by medium pressure chromatography on HP20SS resin (350 mm×50 mm; flow rate 49 ml/min, 250 ml fractions) to give an additional pure sample (1 g) of the required intermediate.

n.m.r. in solvent A: 6.75 (s, 1H); 5.75 (d, 1H); 5.05 (d, 1H); 3.25–3.85 (m, 4H=two AB quartets); 2.95 (q, 2H); 2.30–2.50 (m, 6H); 1.15 (t, 3H).

EXAMPLES 116–151

To a solution of 3-aminomethyl-7-[2-(2-aminothiazol-4-yl)-2-[(Z)-1-carboxy-1-methylethoxyamino)acetamido]ceph-3-em-4-carboxylic acid (0.4 mmole) in DMF (11 ml) and water (3 ml) at 0° was added sodium bicarbonate (4.8 mmole) dissolved in the minimum volume of water followed by the appropriate 4-chloropyridinium toluene-p-sulphonate salt (0.4 mmole). After 1 hour the mixture was treated with HOAc (4.8 mmole) and evaporated to dryness under reduced pressure. The residue was dissolved in water and purified by one of the following methods:
(a) HPLC on an octadecylsilane column using MeOH/water/HOAc 40:60:1 by volume as eluant.
(b) Medium pressure liquid chromatography on a column of Diaion HP20SS resin (supplied commercially by Mitsubishi Chemical Industries Ltd.) using increasing concentrations of acetonitrile (from 0% to 30% v/v) in water as eluant.

In each case the eluant containing the required product was evaporated on a Buchi Rotavapor to remove the organic solvent and the resulting aqueous soution was dried by lyophilisation. Using this general method the following compounds were obtained:

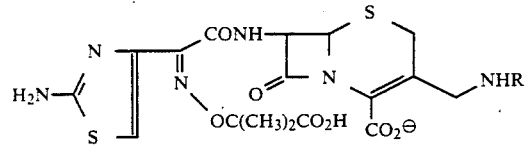

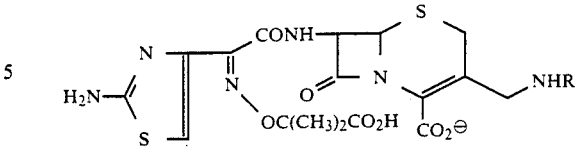

| Example | R | Yield % | Footnotes |
|---|---|---|---|
| 116 | 3,4-difluorophenyl-pyridinium | 70 | 1 |
| 117 | 4-cyanophenyl-pyridinium | 37 | 2 |
| 118 | 2-cyanophenyl-pyridinium | 36 | 3 |
| 119 | 3,4-dicyanophenyl-pyridinium | 18 | 4 |
| 120 | 4-nitrophenyl-pyridinium | 36 | 5 |
| 121 | 4-aminophenyl-pyridinium | 43 | 6 |
| 122 | 3-nitrophenyl-pyridinium | 62 | 7 |
| 123 | 3-aminophenyl-pyridinium | 52 | 8 |
| 124 | 4-carboxyphenyl-pyridinium | 25 | 9 |
| 125 | 4-hydroxyphenyl-pyridinium | 17 | 10 |
| 126 | 2-pyridyl-pyridinium | 20 | 11 |
| 127 | 3-pyridyl-pyridinium | 32 | 12 |
| 128 | 5-cyano-2-pyridyl-pyridinium | 19 | 13 |
| 129 | 2-pyrimidinyl-pyridinium | 13 | 14 |
| 130 | 6-chloro-3-pyridazinyl-pyridinium | 30 | 15 |
| 131 | 3-pyridazinyl-pyridinium | 6 | 16 |
| 132 | 2-furyl-pyridinium | 35 | 17 |
| 133 | 3-furyl-pyridinium | 44 | 18 |
| 134 | 2-thienyl-pyridinium | 6 | 19 |
| 135 | 3-thienyl-pyridinium | 22 | 20 |
| 136 | 2-methyl-5-oxazolyl-pyridinium | 11 | 21 |

-continued

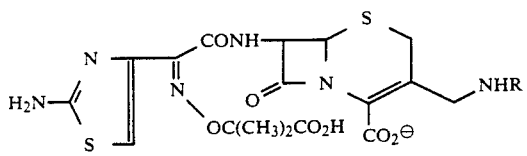

| Example | R | Yield % | Footnotes |
|---|---|---|---|
| 137 | pyridinium-thiazoline | 22 | 22 |
| 138 | pyridinium-benzoxazole | 47 | 23, 24 |
| 139 | pyridinium-benzothiazole | 23 | 25, 26 |
| 140 | N⁺-CH=CH₂ pyridinium | 30 | 27 |
| 141 | pyridinium-C₆H₄-OCH₃ | 25 | 28 |
| 142 | pyridinium-C₆H₄-NHCOCH₃ | 15 | 29 |
| 143 | pyridinium-C₆H₄-CO₂C₂H₅ | 9 | 30 |
| 144 | pyridinium-C₆H₄-CON(CH₃)₂ | 27 | 31 |
| 145 | pyridinium-C₆H₄-SO₂CH₃ | 14 | 32 |
| 146 | pyridinium-C₆H₄-CF₃ | 17 | 33 |
| 147 | pyridinium-C₆H₄-COCH₃ | 20 | 34 |

-continued

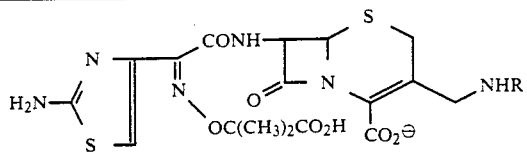

| Example | R | Yield % | Footnotes |
|---|---|---|---|
| 148 | pyridinium-N(CH₂)₃CN | 37 | 35 |
| 149 | pyridinium-CH₂CH=CHCH₂ (pentadienyl) | 18 | 36 |
| 150 | pyridinium-CH₂CH=CHCl | 5 | 37 |
| 151 | pyridinium-CH₂CH=CHCl | 20 | 38 |

Footnotes
1. n.m.r. in solvent A: 1.40 (s, 6H); 3.43 (d, 2H); 3.64 (d, 1H); 4.30 (d, 1H); 4.48 (d, 1H); 5.15 (d, 1H); 5.84 (d, 1H); 6.74 (s, 1H); 7.06 (dd, 1H); 7.26 (dd, 1H); 7.53 (d, 1H); 7.66 (q, 1H); 7.89 (m, 1H); 8.34 (dd, 1H); 8.54 (dd, 1H).
2. n.m.r. in solvent A: 1.46 (s, 6H); 3.45 (d, 1H); 3.66 (d, 1H); 4.35 (d, 1H); 4.51 (d, 1H); 5.17 (d, 1H); 5.86 (d, 1H); 6.74 (s, 1H); 7.10 (d, 1H); 7.28 (d, 1H); 7.86 (d, 2H); 8.12 (d, 2H); 8.46 (d, 1H); 8.64 (d, 1H).
3. n.m.r. in solvent A: 1.44 (s, 6H); 3.45 (d, 1H); 3.65 (d, 1H); 4.31 (d, 1H); 4.52 (d, 1H); 5.15 (d, 1H); 5.85 (d, 1H); 6.75 (s, 1H); 7.13 (dd, 1H); 7.31 (dd, 1H); 7.68–7.84 (m, 2H); 7.90 (dd, 1H); 8.07 (dd, 1H); 8.33 (dd, 1H); 8.54 (dd, 1H).
4. n.m.r. in solvent A: 1.40 (s, 6H); 3.34 (d, 1H); 3.57 (d, 1H); 4.31 (d, 1H); 4.56 (d, 1H); 5.05 (d, 1H); 5.72 (d, 1H); 6.75 (s, 1H); 7.09 (dd, 1H); 7.53 (dd, 1H); 8.20 (dd, 1H); 8.34 (d, 1H); 8.42 (dd, 1H); 8.52 (d, 1H); 8.60 (dd, 1H).
5. n.m.r. in solvent A: 1.35 (s, 6H); 3.30 (d, 1H); 3.57 (d, 1H); 4.24 (d, 1H); 4.44 (d, 1H); 5.05 (d, 1H); 5.70 (d, 1H); 6.65 (s, 1H); 7.00 (d, 1H); 7.15 (d, 1H); 7.80 (d, 2H); 8.30 (d, 2H); 8.30 (d, 1H); 8.48 (d, 1H).
6. A solution of 7-[2-(2-aminothiazol-4-yl)-2-((Z)-1-carboxy-1-methylethoxyimino)acetamido]-3-[1-(4-nitrophenyl)-4-pyridinioaminomethyl]-ceph-3-em-4carboxylate (110 mg) in a mixture of water (12 ml) and DMF (6 ml) was stirred for 1 hr. with 10% palladium on carbon in an atmosphere of hydrogen. The solution was filtered through celite, and the filtrate was evaporated to dryness. The resulting solid was washed with a mixture of water and methanol (3:1 v/v, 3 ml), collected by filtration and dried in vacuo to yield 3-[1-(4-aminophenyl)-4-pyridinio]aminomethyl-7-[2-(2-aminothiazol-4-yl)-2-((Z)-1-carboxy-1-methylethoxyimino)acetamido]ceph-3-em-4-carboxylate (45 mg) having n.m.r. in solvent A: 1.45 (s, 6H); 3.35 (d, 1H); 3.60 (d, 1H); 4.20 (d, 1H); 4.40 (d, 1H); 5.10 (d, 1H); 5.78 (d, 1H); 6.70 (s, 1H); 6.80–8.50 (complex, 8H).
7. n.m.r. in solvent A: 1.40 (s, 6H); 3.35 (d, 1H); 3.65 (d, 1H); 4.27 (d, 1H); 4.50 (d, 1H); 5.10 (d, 1H); 5.78 (d, 1H); 6.70 (s, 1H); 7.00–7.30 (m, 2H); 7.70–8.10 (m, 2H); 8.20–8.60 (m, 4H).
8. The method described in Footnote 6 was repeated using 7-(2-(2-aminothiazol-4-yl)-2-((Z)-1-carboxy-1-methylethoxyimino)acetamido]-3-[1-(3-nitrophenyl)-4-pyridinio]aminomethylceph-3-em-4-carboxylate to yield 3-[1-(3-aminophenyl)-4-pyridinio]aminomethyl-7-[2-(2-aminothiazol-4-yl)-2-((Z)-1-carboxy-1-methylethoxyiminoacetamido]ceph-3-em-4-carboxylate having n.m.r. in solvent A: 1.44 (s, 6H); 3.45 (d, 1H); 3.65 (d, 1H); 4.34 (d, 1H); 4.47 (d, 1H); 5.15 (d, 1H); 5.84 (d, 1H); 6.75 (s, 1H); 6.90–7.45 (m, 6H); 8.35 (d, 1H); 8.54 (d, 1H).
9. The toluene-p-sulphonate salt of 7-[2-(2-aminothiazol-4-yl)-2-((Z)-1-carboxy-1-methylethoxyimino)acetamido]-3-[1-(4-tert-butoxycarbonylphenyl)-4-pyridinio]aminomethylceph-3-em-4-carboxylate (320 mg) was dissolved with stirring in TFA (4 ml). After 15 minutes the solution was evaporated to dryness and the residue was purified by HPLC to yield the toluene-p-sulphonate salt of 7-[2-(2-aminothiazol-4-yl)-2-[(Z)-1-carboxy-1-methylethoxyimino)acetamido]-3-[1-(4-carboxyphenyl)-4-pyridinio]aminomethylceph-3-em-4-carboxylate (73 mg) having n.m.r. in solvent A: 1.43 (s, 6H); 2.27 (s, 3H); 3.43 (d, 1H); 3.64 (d, 1H); 4.34 (d, 1H); 4.53 (d, 1H); 5.15 (d, 1H); 5.82 (d, 1H); 6.75 (s, 1H); 7.12 (d, 3H);

7.35 (d, 1H); 7.50 (d, 2H); 7.77 (d, 2H); 8.16 (d, 2H); 8.47 (d, 1H); 8.65 (d, 1H).

The tert-butyl ester used as starting material in the above process was obtained by the general method using 1-(4-tert-butoxycarbonylphenyl)-4-chloropyridinium toluene-p-sulphonate as starting material.

10. Ice cold TFA (5 ml) was added to a stirred mixture of anisole (1 ml) and 7-[2-(2-aminothiazol-4-yl)-2-((Z)-1-carboxy-1-methylethoxyimino)acetamido]-3-[1-(4-tert-butoxyphenyl)-4-pyridinio]aminomethylceph-3-em-4-carboxylate (200 mg). The reaction mixture was allowed to warm to 10° C. and after 90 mins was evaporated to dryness. Purification of the residue by HPLC yielded 7-[2-(2-aminothiazol-4-yl)-2-((Z)-1-carboxy-1-methylethoxyimino)acetamido]-3-[1-(4-hydroxyphenyl)-4-pyridinio]aminomethylceph-3-em-4-carboxylate having n.m.r. in solvent A: 1.50 (s, 6H); 3.28 (d, 1H); 3.60 (d, 1H); 4.26 (d, 1H); 4.60 (d, 1H); 5.05 (d, 1H); 5.74 (d, 1H); 6.75 (s, 1H); 6.93 (d, 2H); 7.45 (d, 2H); 6.9–7.5 (m, 3H); 8.30 (d, 1H); 8.45 (d, 1H).

The tert-butyl ether used as starting material in the above process was obtained by the general method using 1-(4-tert-butoxyphenyl)-4-chloropyridinium toluene-p-sulphonate as starting material.

11. n.m.r. in solvent A: 1.40 (s, 6H); 3.45 (d, 1H); 3.65 (d, 1H); 4.35 (d, 1H); 4.50 (d, 1H); 5.15 (d, 1H); 5.75 (d, 1H); 6.75 (s, 1H); 7.10 (dd, 1H); 7.30 (m, 1H); 7.90 (d, 1H); 8.15 (m, 1H); 8.60 (d, 1H); 8.80 (dd, 1H); 8.95 (dd, 1H).

12. n.m.r. in solvent A: 1.40 (s, 6H); 3.35 (d, 1H); 3.62 (d, 1H); 4.25 (d, 1H); 4.46 (d, 1H); 5.05 (d, 1H); 5.80 (d, 1H); 6.75 (s, 1H); 7.04 (d, 1H); 7.10 (d, 1H); 7.55 (dd, 1H); 8.05 (d, 1H); 8.35 (d, 1H); 8.52 (d, 1H); 8.65 (d, 1H); 8.80 (d, 1H).

13. n.m.r. in solvent A: 1.40 (s, 6H); 3.34 (d, 1H); 3.67 (d, 1H), 4.36 (d, 1H); 4.57 (d, 1H); 5.07 (d, 1H); 5.75 (d, 1H); 6.74 (s, 1H); 7.12 (d, 1H); 7.55 (d, 1H); 8.15 (d, 1H); 8.60 (dd, 1H); 8.82 (d, 1H); 8.95 (d, 1H); 9.05 (d, 1H).

14. n.m.r. in solvent A: 1.42 (s, 6H); 3.34 (d, 1H); 3.56 (d, 1H); 4.37 (d, 1H); 4.56 (d, 1H); 5.07 (d, 1H); 5.74 (d, 1H); 6.74 (s, 1H); 7.12 (dd, 1H); 7.50 (dd, 1H); 7.60 (t, 1H); 8.98 (d, 2H); 9.14 (dd, 1H); 9.24 (dd, 1H).

15. n.m.r. in solvent A: 1.45 (s, 6H); 3.35 (d, 1H); 3.58 (d, 1H); 4.35 (d, 1H); 4.60 (d, 1H); 5.07 (d, 1H); 5.74 (d, 1H); 6.74 (s, 1H); 7.14 (dd, 1H); 7.58 (dd, 1H); 8.26 (d, 1H); 8.38 (d, 1H); 8.76 (dd, 1H); 8.86 (dd, 1H).

16. n.m.r. in solvent A: 1.44 (s, 6H); 3.30 (d, 1H); 3.56 (d, 1H); 4.30 (d, 1H); 4.60 (d, 1H); 5.07 (d, 1H); 5.72 (d, 1H); 6.72 (s, 1H); 7.19 (d, 1H); 7.60 (d, 1H); 7.9–8.6 (m, 2H); 8.86 (m, 2H); 9.37 (q, 1H).

17. n.m.r. in solvent A: 1.45 (s, 6H); 3.29 (d, 1H); 3.54 (d, 1H); 4.28 (d, 1H); 4.56 (d, 1H); 5.05 (d, 1H); 5.71 (d, 1H); 6.70 (dd, 1H); 6.75 (s, 1H); 6.88 (dd, 1H); 7.06 (dd, 1H); 7.58 (dd, 1H); 7.76 (dd, 1H); 8.44 (dd, 1H); 8.60 (dd, 1H).

18. n.m.r. in solvent A: 1.44 (s, 6H); 3.44 (d, 1H); 3.64 (d, 1H); 4.32 (d, 1H); 4.47 (d, 1H); 5.16 (d, 1H); 5.84 (d, 1H); 6.74 (s, 1H); 7.10 (dd, 1H); 7.05 (dd, 1H); 7.25 (dd, 1H); 7.85 (dd, 1H); 8.36 (dd, 1H); 8.41 (dd, 1H); 8.58 (dd, 1H).

19. n.m.r. in solvent A: 1.43 (s, 6H); 3.40 (d, 1H); 3.60 (d, 1H); 4.30 (d, 1H); 4.58 (d, 1H); 5.13 (d, 1H); 5.81 (d, 1H) (d, 1H); 6.74 (s, 1H); 7.00–7.15 (m, 2H); 7.20 (dd, 1H); 7.46 (dd, 1H); 7.54 (dd, 1H); 8.32 (dd, 1H); 8.50 (dd, 1H).

20. n.m.r. in solvent A: 1.45 (s,6H); 3.46 (d, 1H); 3.67 (d, 1H); 4.34 (d, 1H); 4.52 (d, 1H); 5.17 (d, 1H); 5.85 (d, 1H); 6.75 (s, 1H); 7.08 (dd, 1H); 7.24 (d, 1H); 7.50 (dd, 1H); 7.80 (dd, 1H); 7.98 (dd, 1H); 8.46 (dd, 1H); 8.64 (dd, 1H).

21. n.m.r. in solvent A: 1.45 (s, 6H); 2.10 (s, 3H); 3.30 (d, 1H); 3.55 (d, 1H); 4.35 (d, 1H); 4.55 (d, 1H); 5.05 (d, 1H), 5.70 (d, 1H); 6.75 (s, 1H); 7.05 (d, 2H); 7.15 (d, 2H); 7.95 (s, 1H); 8.60 (dd, 2H); 8.70 (dd, 2H).

22. n.m.r. in solvent A: 1.43 (s, 6H); 3.33 (d, 1H); 3.56 (d, 1H); 4.35 (d, 1H); 4.56 (d, 1H); 5.06 (d, 1H); 5.72 (d, 1H); 6.74 (s, 1H); 7.08 (dd, 1H); 7.51 (dd, 1H); 7.74 (s, 2H); 8.66 (dd, 1H); 8.75 (dd, 1H).

23. Prepared by the general method using 1-(2-benzoxazolyl)-4-methylsulphinylpyridinium chloride in place of the 4-chloropyridinium toluene-p-sulphonate.

The pyridinium salt was prepared as follows. A solution of 2-chlorobenzoxazole (1.38 g) and 4-methylthiopyridine (1.13 g) in anhydrous methylene chloride was kept in the dark overnight. The resulting crystalline precipitate of 1-(2-benzoxazolyl)-4-methylthiopyridinium chloride (1.86 g) was collected by filtration, washed with anhydrous methylene chloride and dried in vacuo.

A solution of 3-chloroperbenzoic acid (127 mg, 85% pure) in methylene chloride (3 ml) was added dropwise to a stirred ice cold solution of 1-(2-benzoxazolyl)-4-methylthiopyridinium chloride (139 mg) in methylene chloride (3 ml) and TFA (0.10 ml). The solution was allowed to warm to. 20° C. After 40 minutes, toluene (2 ml) was added and the mixture was evaporated to dryness to yield a mixture of 1-(2-benzoxazolyl)-4-methylsulphinylpyridinium chloride and 3-chlorobenzoic acid which was used directly in the general method.

24. n.m.r. in solvent A: 1.45 (s, 6H); 3.30 (d, 1H); 3.65 (d, 1H); 4.35 (d, 1H); 4.62 (d, 1H); 5.05 (d, 1H); 5.70 (d, 1H); 6.74 (s, 1H); 7.00–7.90 (m, 6H); 8.75 (dd, 1H); 8.85 (dd, 1H).

25. Prepared by the process described in Footnote 23, using 2-chlorobenzothiazole as starting material in place of 2-chlorobenzoxazole.

26. n.m.r. in solvent A: 1.40 (s, 6H); 3.33 (d, 1H); 3.56 (d, 1H); 4.37 (d, 1H); 4.64 (d, 1H); 5.06 (d, 1H); 5.72 (d, 1H); 6.74 (s, 1H); 7.15 (d, 1H); 7.45–7.70 (m, 3H); 8.00 (d, 1H); 8.18 (d, 1H); 8.80 (d, 1H); 8.86 (d, 1H).

27. n.m.r. in solvent A: 1.45 (s, 6H); 3.30 (d, 1H); 3.55 (d, 1H); 4.20 (d, 1H); 4.45 (d, 1H); 5.05 (d, 1H); 5.15 (d, 1H); 5.25 (d, 1H); 5.70 (d, 1H); 6.75 (s, 1H); 6.80–7.20 (m, 3H); 8.15 (d, 1H); 8.30 (d, 1H).

28. n.m.r. in solvent A: 1.45 (s, 6H), 3.40 (d, 1H); 3.52 (d, 1H); 3.82 (s, 3H); 4.28 (d, 1H); 4.44 (d, 1H); 5.04 (d, 1H); 5.75 (d, 1H); 6.75 (s, 1H); 7.00–7.22 (m, 3H); 7.35–7.62 (m, 3H); 8.30 (d, 1H); 8.45 (d, 1H).

29. n.m.r. in solvent A: 1.45 (s, 6H); 2.10 (s, 3H); 3.30 (d, 1H); 3.65 (d, 1H); 4.29 (d, 1H); 4.59 (d, 1H); 5.07 (d, 1H); 5.71 (d, 1H); 6.75 (s, 1H); 7.07 (d, 1H); 7.57 (d, 2H); 7.57 (d, 1H); 7.80 (d, 2H); 8.35 (d, 1H); 8.50 (d, 1H).

30. n.m.r. in solvent A: 1.35 (s, 6H); 1.45 (t, 3H); 3.48 (d, 1H); 3.66 (d, 1H); 4.30 (m, 3H); 4.50 (d, 1H); 5.17 (d, 1H); 5.85 (d, 1H); 6.75 (s, 1H); 7.11 (d, 1H); 7.36 (d, 1H); 7.82 (d, 2H); 9.15 (d, 2H); 9.50 (d, 1H); 9.70 (d, 1H).

31. n.m.r. in solvent A: 1.40 (s, 6H); 2.80 (s, 6H); 3.30 (d, 1H); 3.58 (d, 1H); 4.25 (d, 1H); 4.50 (d, 1H); 5.05 (d, 1H); 5.70 (d, 1H); 6.72 (s, 1H); 7.00 (d, 1H); 7.30 (d, 1H); 7.60 (m, 4H); 8.30 (d, 1H); 8.45 (d, 1H).

32. n.m.r. in solvent A: 1.45 (s, 6H); 3.30 (s, 3H); 3.45 (d, 1H); 3.65 (d, 1H); 4.35 (d, 1H); 4.50 (d, 1H); 5.15 (d, 1H); 5.85 (d, 1H); 6.75 (s, 1H); 7.14 (d, 1H); 7.33 (d, 1H); 7.94 (d, 2H); 8.16 (d, 2H); 8.46 (d, 1H); 8.66 (d, 1H).

33. n.m.r. spectrum in solvent A: 1.45 (s, 6H); 3.35 (d, 1H); 3.60 (d, 1H); 4.35 (d, 1H); 4.55 (d, 1H); 5.05 (d, 1H); 5.70 (d, 1H); 6.70 (s, 1H); 7.10 (dd, 1H); 7.46 (dd, 1H); 8.12 (d, 1H); 8.50 (d, 1H); 8.80 (d, 1H); 8.94 (d, 1H); 8.97 (broad, 1H).

34. n.m.r. spectrum in solvent A: 1.45 (s, 6H); 2.70 (s, 3H); 3.30 (d, 1H); 3.55 (d, 1H); 4.30 (d, 1H); 4.60 (d, 1H); 5.05 (d, 1H); 5.70 (d, 1H); 6.75 (s, 1H); 7.10 (d, 1H); 7.60 (d, 1H); 7.80 (d, 2H); 8.15 (d, 2H); 8.35 (d, 1H), 8.55 (d, 1H).

35. n.m.r. in solvent A: 1.40 (s, 6H); 2.08 (m, 2H); 2.50 (t, 2H); 3.26 (d, 1H); 3.50 (d, 1H); 4.15 (t, 2H); 4.20 (d, 1H); 4.42 (d, 1H); 5.02 (d, 1H); 5.69 (d, 1H); 6.73 (d, 1H); 6.94 (d, 1H); 7.35 (d, 1H); 9.10 (d, 1H); 8.25 (d, 1H).

36. n.m.r. in solvent A: 1.46 (s, 6H); 3.26 (d, 1H); 3.50 (d, 1H); 4.20 (d, 1H); 4.44 (d, 1H); 4.80 (d, 2H); 5.05 (d, 1H); 5.20 (d, 1H); 5.32 (d, 1H); 5.72 (d, 1H); 5.90 (d t, 1H); 6.3–6.6 (m, 2H); 6.74 (s, 1H); 6.94 (d, 1H); 7.38 (d, 1H); 8.16 (d, 1H); 8.25 (d, 1H).

37. n.m.r. in solvent A: 1.40 (s, 6H); 3.40 (d, 1H); 3.60 (d, 1H); 4.25 (d, 1H); 4.40 (d, 1H); 4.90 (d, 2H); 5.15 (d, 1H); 5.80 (d, 1H); 6.20 (m, 1H); 6.65 (d, 1H); 6.75 (d, 1H); 6.90 (d, 1H); 7.10 (d, 1H); 8.05 (d, 1H); 8.20 (d, 1H).

38. n.m.r. in solvent A: 1.40 (s, 6H); 3.40 (d, 1H); 3.60 (d, 1H); 4.25 (d, 1H); 4.35 (d, 1H); 4.80 (d, 2H); 5.15 (d, 1H); 5.85 (d, 1H); 6.20 (m, 1H); 6.20 (m, 1H); 6.70 (d, 1H); 6.75 (s, 1H); 6.90 (d, 1H); 7.10 (d, 1H); 8.10 (d, 1H); 8.25 (d, 1H).

The 1-substituted-4-chloropyridinium toluene-p-sulphonate salts used as starting materials in the above processes may be prepared as follows:

A solution of the appropriate 1-substituted-4-pyridone (2.5 mole) and toluene-p-sulphonyl chloride (3.8 mmole) in DMF (10 ml) was stirred at 100° C. for 10 mins. The reaction mixture was cooled and evaporated to dryness. Trituration of the residue with ether yielded the required 4-chloropyridinium toluene-p-sulphonate salt as a solid which was used without further purification in the preparation of the final product. Using the general process the following compounds were prepared:

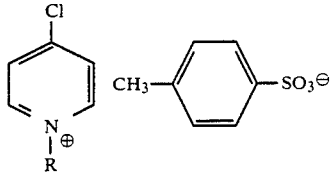

| R | Footnotes | Starting material for Example Number |
|---|---|---|
| 3,4-difluorophenyl | 1 | 116 |
| 4-cyanophenyl | 2 | 117 |
| 2-cyanophenyl | 3 | 118 |
| 3,4-dicyanophenyl | 3 | 119 |
| 4-nitrophenyl | 3 | 120, 121 |
| 3-nitrophenyl | 4 | 122, 123 |
| 4-tert-butoxycarbonylphenyl | 5 | 124 |
| 4-tert-butoxyphenyl | 6 | 125 |
| 2-pyridyl | 7 | 126 |
| 3-pyridyl | 4 | 127 |
| 5-cyano-2-pyridyl | 7 | 128 |
| 2-pyrimidinyl | 7 | 129 |
| 6-chloro-3-pyridazinyl | 7 | 130 |
| 3-pyridazinyl | 8 | 131 |
| 2-furyl | 9 | 132 |
| 3-furyl | 10 | 133 |
| 2-thienyl | 11 | 134 |
| 3-thienyl | 11 | 135 |
| 4-methyl-2-oxazolyl | 12 | 136 |
| 2-thiazolyl | 13 | 137 |
| vinyl | | 140 |
| 4-methoxyphenyl | 4 | 141 |

-continued

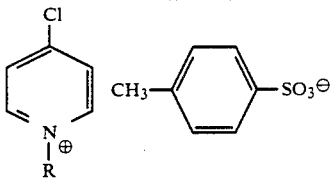

| R | Footnotes | Starting material for Example Number |
|---|---|---|
| 4-acetamidophenyl | 14 | 142 |
| 4-ethoxycarbonylphenyl | 5 | 143 |
| 4-dimethylaminocarboxyphenyl | 15 | 144 |
| 4-methylsulphonylphenyl | 16 | 145 |
| 5-trifluoromethyl-2-pyridyl | 7 | 146 |
| 4-acetoxyphenyl | 5 | 147 |
| 3-cyanopropyl | 17 | 148 |
| penta-2,4-dienyl | 18 | 149 |
| cis-3-chloroallyl | 19 | 150 |
| trans-3-chloroallyl | 19 | 151 |

Footnotes

1. The starting material was prepared as follows: A mixture of alpha-pyrone (880 mg.), 3,4-difluoroaniline (1.54 g.) and concentrated hydrochloric acid (0.8 ml.) in water (10 ml.) was stirred under reflux for 2 hours. The reaction mixture was cooled and basified with aqueous ammonia solution. The precipitated product was filtered off, washed with cold ethyl acetate (10 ml.) and dried in vacuo to yield 1-(3,4-difluorophenyl)-4-pyridone (1.10 g.) as a buff solid.
2. The starting material was prepared as follows: Sodium hydride (410 mg. of a 1% dispersion in mineral oil) was placed in an argon atmosphere, washed free of oil with n-pentane and suspended in DMF (10 ml.). Solid 4-hydroxypyridine (1.00 g.) was added in small portions to the suspension. Stirring was continued for 15 minutes after the evolution of hydrogen gas had ceased and then a solution of 4-fluorobenzonitrile (1.27 g.) in DMF (3 ml.) was added. The resulting mixture was stirred at 110° C. for 30 minutes and then poured whilst still hot into cold water (60 ml.). After cooling for 30 minutes in ice the crystalline precipitate of 1-(4-cyanophenyl)-4-pyridone (1.45 g.) was collected by filtration, washed with water, dried in vacuo and recrystallised from EtOAc.
3. The pyridone starting material was prepared by the method described in Footnote 2, using the appropriate substituted chlorobenzene in place of 4-fluorobenzonitrile.
4. The starting material was prepared by the method described in Example 2 using the appropriate aniline in place of 4-fluoroaniline.
5. The pyridone starting material was prepared by the method described in Footnote 2, using the appropriate substituted fluorobenzene in place of 4-fluorobenzonitrile.
6. The pyridone starting material was prepared as follows:
A mixture of alpha-pyridone (440 mg.), 4-tert-butoxyaniline (7.55 mg.) and HOAc (0.262 ml.) was stirred at 100° C. for 10 minutes in an argon atmosphere. The cooled reaction mixture was evaporated to dryness, using the azeotropic evaporation of added toluene to remove the last traces of HOAc. The residue was purified by chromatography on a column of Kieselgel 60, eluting with methylene chloride, then 95:5 v/v methylene chloride; methanol, to give 1-(4-tert-butoxyphenyl)-4-pyridone (340 mg.) having n.m.r. in CDCl3: 1.40 (s, 9H), 6.50 (d, 2H), 7.0–7.3 (m, 4H), 7.60 (d, 2H).
7. The pyridone starting material was prepared by the method described in Footnote 2, using the appropriate 2-chloroheterocycle in place of 4-fluorobenzonitrile.
8. The pyridone starting material was prepared as follows:
A solution of 1-(6-chloro-3-pyridazinyl)-4-pyridone (1.00 g.) and sodium acetate (0.50 g.) in EtOH (50 ml.) and water (3 ml.) containing 10% palladium on carbon (200 mg.) was stirred for 75 minutes in an atomosphere of hydrogen.
The mixture was filtered through kieselguhr and the filtrate was evaporated to dryness. Recrystallisation of the residue from EtOAc yielded 1-(3-pyridazinyl)-4-pyridone, (350 mg.) having n.m.r. in solvent A: 6.35 (d, 2H), 7.95 (q, 1H), 8.20 (q, 1H), 8.50 (d, 2H), 9.30 (q, 1H).
9. The pyridone starting material was prepared as follows:
Sodium hydride (1.69 g. of a 1% dispersion in mineral oil) was placed in an argon atmosphere, washed free of oil with n-pentane and suspended in DMSO (27 ml.). Solid 4-hydroxypyridine (4.12 g.) was added in small portions to the stirred suspension. Stirring was continued for 15 minutes after the evolution of hydrogen gas had ceased. Powdered methyl 5-nitro-2-furoate (6.18 g.) was then added and stirring was continued for 48 hours. The reaction mixture was evaporated to dryness and the dark brown residue was extracted with 95:5 v/v methylene chloride/MeOH (3×100 ml.). The extracts were passed through a column of Kieselgel 60 (50 mg.) and the eluent was evaporated to dryness. The residue was dissolved in methylene chloride (100 ml.) and the solution was filtered. The solution was filtered. The solution, on addition to ca 20 ml. deposited pale brown crystals of the methyl ester, 1-(5-methoxycarbonyl-2-furyl)-4-pyridone (3.07 g.), having m.p. 194°–6° C. Chromatography of the mother liquor on Kieselgel 60 afforded a further crop (863 mg.) of the same product.
The methyl ester (3.95 g.) was stirred in methanol (78 ml.) in an argon atmosphere, while a solution of potassium hydroxide (4.87 g.) in water (39 ml.) was added. The methyl ester rapidly dissolved. Stirring was continued overnight and the reaction mixture was evaporated to dryness. The residue was dissolved in the minimum volume of water and acidified with N-hydrochloric acid to pH. 1. The resulting precipitate was isolated by centrifugation, washed with water then acetone, and dried in vacuo to yield the acid, 1-(5-carboxy-2-furyl)-4-pyridone (3.74 g.)
A mixture of the acid (3.74 g.), copper bronze (1.64 g.) and quinoline (8 ml.) was stirred at 210° C. in an argon atmosphere until the evolution of carbon dioxide ceased (ca. 30 minutes). The cooled reaction mixture was dissolved in EtOAc and filtered through kieselguhr. The filtrate was evaporated to dryness and the residue was purified by chromatography on Kieselgel 60 (30 g.) eluting initially with methylene chloride to remove quinoline then with 95:5 v/v methylene chloride/MeOH to afford 1-(2-furyl)-4-pyridone (2.20 g.).
10. The pyridone starting material was prepared as follows:
A mixture of 3-bromofuran (2.50 g.), freshly sublimed 4-hydroxypyridine (1.61 g.), copper powder (2.20 g.) and powdered anhydrous potassium carbonate (4.80 g.) in DMF (25 ml.) was stirred at 150° C. for 2 hours in an argon atmosphere. The cooled reaction mixture was filtered through kieselguhr and the filtrate was evaporated to dryness. The residue was extracted with warm 95:5 v/v chloroform/MeOH (100 ml.). The resulting solution was applied to a column of Kieselgel 60 (30 g.). Elution with the same solvent gave 1-(3-furyl)-4-pyridone (1.17 g.).
11. The pyridone starting material was prepared by the method described in footnote 10, using the appropriate bromothiophene in place of 3-bromofuran.
12. The pyridone starting material was prepared by the method described in footnote 2, using 4-methyl-2-methylsulphinyloxazole in place of 4-fluorobenzonitrile.
13. The pyridone starting material was prepared by the method described in footnote 2, using 2-bromothiazole in place of 4-fluorobenzonitrile.
14. The starting material was prepared as follows: A solution of 1-(4-nitrophenyl)-4-pyridone (500 mg) in EtOH (5 ml) and DMF (5 ml) was stirred at 80° C. for 30 minutes with 10% palladium on carbon (150 mg) in an atmosphere of hydrogen. The reaction mixture was cooled and filtered through kieselguhr. The filtrate was evaporated to dryness and the solid residue was stirred overnight with a mixture of acetic anhydride (1 ml), pyridine (3 ml) and HOAc (3 ml). The reaction mixture was evaporated to dryness to yield 1-(4-acetamidophenyl)-4-pyridone (420 mg.) as a white solid.
15. The pyridone starting material was prepared as follows:
A mixture of 1-(4-ethoxycarbonylphenyl)-4-pyridone (1.0 g) and 33% w/v dimethylamine in ethanol was stirred during the dropwise addition of a solution of sodium ethoxide [prepared by the addition of sodium metal (50 mg) to ethanol (2.5 ml)]. Stirring was continued overnight, then the reaction mixture was evaporated to dryness to yield 1-(4-dimethylcarbamoylphenyl)-4-pyridone which was used without purification.
16. The pyridone starting material was prepared as follows:
Using the method described in Example 2, 4-methylthioaniline was converted into 1-(4-methylthiophenyl)-4-pyridone. A mixture of the pyridone (1.80 mg), HOAc (14 ml) and 100 volumes aqueous hydrogen peroxide (4.5 ml) were stirred at 70° C. for 2 hours. The cooled reaction mixture was diluted with water and extracted with ethyl acetate. The ethyl acetate solution was washed with aqueous sodium metabisulphite, dried with sodium sulphate, and evaporated to yield 1-(4-methylsulphonylphenyl)-4-pyridone (1.15 g) which was used without further purification.
17. The pyridone starting material was prepared by the method described in footnote 2, using 4-bromobutyronitrile in place of 4-fluorobenzonitrile.
18. The pyridone starting material was prepared as follows:
A mixture of 2-chloropenta-2,4-diene (1.49 g), 4-hydroxypyridine (1.39 g), powdered anhydrous potassium carbonate (4.14 g) and DMF (10 ml) was stirred for 90 minutes at 80° C. in an argon atmosphere. The reaction mixture was cooled and the DMF was evaporated. The residue was extracted with 9:1 v.v methylene chloride/methanol (200 ml). The exacts were filtered through a pad of Kieselgel 60 (30 g) and the filtrates were evaporated to dryness to give a brown oil. Chromatography of this oil on Kieselgel 60, eluting initially with methylene chloride, then 19:1 v/v methylene chloride/methanol, afforded 1-(penta-2,4-dienyl)-4-pyridone (1.36 g) as a pale orange oil.
19. The pyridone starting materials were prepared as follows:
A solution of 1,3-dichloropropene (cis/trans mixture, 1.97 ml) and 4-hydroxypyridine (2.00 g) in acetone (25 ml) was stirred with powdered anhydrous potassium carbonate (2.90 g) for 1 hour under reflux. Further portions of 1,3-dichloropropene (1.97 ml) and potassium carbonate (2.90 g) were added and the reaction mixture was stirred for a further hour under reflux. The cooled reaction mixture was filtered and the solid residue was washed well with acetone. The combined acetone filtrates were evaporated to dryness. The oily residue was chromatographed on a column of Kieselgel 60 (100 g) eluting with methylene chloride, then 19:1 v/v methylene chloride/methanol, to separate the cis and trans isomers of the product, 2-(3-chloroallyl)-4-pyridone.

EXAMPLES 152–158

To a solution of 3-aminomethyl-7-[2-(2-aminothiazol-4-yl)-2-[(Z)-1-carboxy-1-methylethoxyamino)acetamido]ceph-3-em-4-carboxylic acid (0.4 mmole) in DMF (11 ml.) and water (3 ml) at 0° was added sodium bicarbonate (4.8 mmole) dissolved in the minimum volume of water, followed by a solution of the appropriate pyridinium salt (0.5 mmole) in DMF (5 ml). After 1 hour the mixture was treated with HOAc (4.8 mmole) and evaporated to dryness under reduced pressure. The residue was dissolved in water and purified by chromatography on Diaion HP20SS resin.

Using this general process the following compounds were prepared 6.75 (s, 1H); 6.80 (m, 1H); 7.00 (dd, 1H); 7.45 (dd, 1H); 8.10 (d, 1H); 8.25 (d, 1H).
7. n.m.r. in solvent A: 1.45 (s, 6H); 1.95 (s, 3H); 3.40 (d, 1H); 3.60 (d, 1H); 4.25 (d, 1H); 4.40 (d, 1H); 4.90 (s, 2H); 5.15 (d, 1H); 5.30 (s, 1H); 5.85 (d, 1H); 6.75 (s, 1H); 6.95 (d, 1H); 7.10 (d, 1H); 8.00 (d, 1H); 8.20 (d, 1H).

The pyridinium salts used as starting materials in the above process may be prepared as follows:

A solution of 3-chloroperbenzoic acid (1.05 mmole)

[Structure: core cephalosporin-like compound with aminothiazole, oxime-OC(CH₃)₂CO₂H, β-lactam with CONH, and =CH-NHR side chain with CO₂⁻]

| Example | -R | Yield % | Footnotes |
|---|---|---|---|
| 152 | [4-methylpyridinium-CH₂-CH=CH-C₆H₄-NO₂] | 10 | 1 |
| 153 | [4-methylpyridinium-CH₂-CH=CH-CN] | 16 | 2 |
| 154 | [4-methylpyridinium-CH₂-CH=CH-C(O)-N(piperidinyl)] | 30 | 3 |
| 155 | [4-methylpyridinium-CH₂-CH=CH-C(O)-N(morpholinyl)] | 24 | 4 |
| 156 | [4-methylpyridinium-CH₂-CH=CH-C(O)-NH(CH₂)₂CH₃] | 44 | 5 |
| 157 | [4-methylpyridinium-CH₂-CH=CH-C(O)-NH₂] | 15 | 6 |
| 158 | [4-methylpyridinium-CH₂-C(CH₃)=CH-CN] | 8 | 7 |

1. n.m.r. in solvent A: 1.40 (s, 6H); 3.30 (d, 1H); 3.50 (d, 1H); 4.20 (d, 1H); 4.40 (d, 1H); 4.95 (d, 2H); 5.05 (d, 1H); 5.70 (d, 1H); 6.70 (s, 1H); 6.95 (d, 1H); 7.25 (d, 1H); 7.65 (d, 2H); 8.10 (d, 1H); 8.15 (d, 2H); 8.30 (d, 1H).
2. n.m.r. in solvent A: 1.45 (s, 6H); 3.27 (d, 1H); 3.50 (d, 1H); 4.21 (d, 1H); 4.43 (d, 1H); 4.95 (d, 2H); 5.04 (d, 1H); 5.68 (d, 1H); 6.28 (m, 1H); 6.74 (s, 1H); 6.90–7.45 (m, 3H); 8.02 (d, 1H); 8.20 (d, 1H).
3. n.m.r. in solvent A: 1.40 (m, 12H); 3.24 (d, 1H); 3.45 (m, 5H); 4.20 (d, 1H); 4.48 (d, 1H); 4.90 (broad, 2H); 5.05 (d, 1H); 5.70 (d, 1H); 6.70 (s, 1H); 6.80 (m, 1H); 6.95 (m, 2H); 7.50 (dd, 1H); 8.10 (d, 1H); 8.28 (d, 1H).
4. n.m.r. in solvent A: 1.44 (s, 6H); 3.55 (m, 10H); 4.25 (d, 1H); 4.40 (d, 1H); 4.90 (d, 2H); 5.15 (d, 1H); 5.83 (d, 1H); 6.65 (m, 2H); 6.75 (s, 1H); 6.95 (d, 1H); 7.07 (d, 1H); 8.10 (d, 1H); 8.27 (d, 1H).
5. n.m.r. in solvent A: 0.85 (t, 3H), 1.35 (m, 2H); 1.40 (s, 6H); 3.05 (m, 2H); 3.25 (d, 1H); 3.50 (d, 1H); 4.20 (d, 1H); 4.45 (d, 1H); 4.90 (d, 1H); 5.05 (d, 1H); 5.70 (d, 1H); 5.85 (d, 1H); 6.75 (s, 1H); 6.80 (m, 1H); 6.95 (dd, 1H); 7.40 (dd, 1H); 8.10 (d, 1H); 8.20 (d, 1H).
6. n.m.r. in solvent A: 1.40 (s, 6H); 3.25 (d, 1H); 3.50 (d, 1H); 4.20 (d, 1H); 4.50 (d, 1H); 4.95 (d, 2H); 5.05 (d, 1H); 5.70 (d, 1H); 5.80 (d, 1H);

in anhydrous methylene chloride (2 ml) was added dropwise to a stirred solution at the appropriate 1-substituted-4-methylthiopyridinium salt (0.5 mmole) in methylene chloride (5 ml) and TFA (0.1 ml) at 0°. The reaction mixture was allowed to warm to room temperature over 1 hour and was then evaporated to dryness. The residue was washed with ether to remove 3-chlorobenzoic acid and the insoluble residue, a mixture of the appropriate 4-methylsulphinyl- and 4-methylsulphonylpyridinium salts, was used directly in the above process.

Using this general procedure the following compounds were prepared:

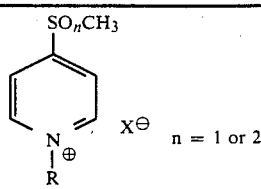

n = 1 or 2

| —R | X | Footnotes | Starting Material for Example No. |
|---|---|---|---|
| 4-nitrocinnamyl | Cl | 1 | 152 |
| trans-3-cyanoallyl | BF$_4$ | 2 | 153 |
| trans-3-(2-piperidino-carboxy)allyl | Br | 3 | 154 |
| trans-3-(1-morpholino-carboxy)allyl | Br | 4 | 155 |
| trans-3-(N-propyl-aminocarboxy)allyl | Br | 4 | 156 |
| trans-3-(amino-carboxy)allyl | Br | 4 | 157 |
| E-3-cyano-2-methyl-allyl | Br | 4 | 158 |

Footnotes
1. The 1-(4-nitrocinnamyl)-4-methylthiopyridinium chloride starting material was prepared as follows. A solution of 4-nitrocinnamyl chloride (181 mg) and 4-methylthiopyridine (125 mg) in acetonitrile (1 ml) was kept in the dark for 48 hours. The solvent was evaporated and the residue was triturated with ether to give the required starting material as an off-white solid (170 mg).
2. The 1-(trans-3-cyanoallyl)-4-methylthiopyridinium tetrafluoroborate starting material was prepared as follows. A solution of 4-bromo-crotononitrile (660 mg) and 4-methylthiopyridine (565 mg) in anhydrous methylene chloride (3 ml) was kept in the dark for 48 hours. The resulting black crystalline solid (888 mg) was filtered off and dried in vacuo. This solid was dissolved in a mixture of water (20 ml) and DMF (10 ml). To this stirred solution was added a solution of silver tetrafluoroborate (636 mg) in water (3 ml). After minutes the solution was filtered through celite and evaporated to dryness. The resulting gum was dissolved in water (20 ml), refiltered and freeze-dried to yield the starting material as a fluffy orange solid (810 mg).
3. The 1-[trans-3(1-piperidinocarboxy)]allyl-4-methylthiopyridinium bromide starting material was prepared as follows. A solution of trans-3-(1-piperidinocarboxy)allyl bromide (440 mg) and 4-methylthiopyridine (240 mg) in acetonitrile (5 ml) was kept in the dark for 24 hours. The solvent was evaporated and the residue was washed with ether to afford the required starting material as a gum.
4. The required starting material was prepared, using the procedure in Footnote 3, by reacting 4-methylthiopyridine with the appropriate substituted allyl bromide.

EXAMPLES 159–160

Using the general processes described in Example 116, with the appropriate 3-aminomethylcephalosporin and pyridinium salt starting materials the following compounds were prepared.

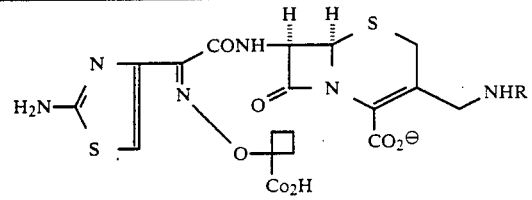

| Example | —R | Yield % | Footnotes |
|---|---|---|---|
| 159 | | 17 | 1 |
| 160 | =CH-CN) | 15 | 2 |

Footnotes
1. n.m.r. in solvent A: 2.40 (m, 6H); 3.40 (d, 1H); 3.60 (d, 1H); 4.25 (d, 1H); 4.38 (d, 1H); 4.80 (d, 1H); 5.15 (d, 1H); 5.85 (d, 1H); 6.20 (m, 1H); 6.70 (d, 1H); 6.75 (s, 1H); 6.90 (d, 1H); 7.10 (d, 1H); 8.05 (d, 1H); 8.25 (d, 1H).
2. n.m.r. in solvent A: 1.96 (s, 3H); 2.40 (m, 6H); 3.42 (d, 1H); 3.65 (d, 1H); 4.27 (d, 1H); 4.40 (d, 1H); 4.95 (s, 2H); 5.16 (d, 1H); 5.32 (s, 1H); 5.85 (d, 1H); 6.74 (s, 1H); 6.97 (d, 1H); 7.10 (d, 1H); 8.04 (d, 1H); 8.25 (d, 1H).

EXAMPLES 161–171

The general process described in Example 1 was repeated using the appropriate heterocyclic starting material. The reactions were carried out in DMF/water mixtures in the presence of NaHCO$_3$ at the temperature in the range ambient to 75° for 0.4–4 hours. The product was purified on a octadecylsilane column and the following compounds were thus prepared.

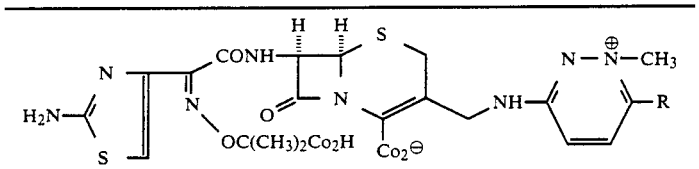

| Example | —R | Yield % | Footnotes |
|---|---|---|---|
| 161 | —CH$_3$ | 7 | 1,2,3 |
| 162 | —NH—CH$_2$CH=CH$_2$ | 18 | 4,5,6 |
| 163 | —NH—CH(CH$_3$)$_2$ | 22 | 7,8,9 |
| 154 | —N(CH$_3$)$_2$ | 25 | 10,11,12 |
| 165 | —NH—CH$_2$—C$_6$H$_4$—NO$_2$ | 14 | 13,14,15 |
| 166 | —NH—CH$_2$-(2-thienyl) | 4.5 | 16,17,18 |
| 167 | —NH—CH$_2$CH$_2$NH$_2$ | 12 | 19,20,21,22 |
| 168 | —NH—CH$_2$CH$_2$OH | 11 | 23,24,25 |

-continued

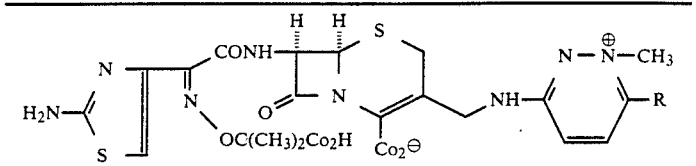

| Example | —R | Yield % | Footnotes |
|---|---|---|---|
| 169 | —NH—CH$_2$CH$_2$OCH$_3$ | 6 | 26,27,28 |
| 170 | —SCH$_3$ | 32 | 29,30,31 |
| 171 | —SCH$_2$CH$_2$NHCOCH$_3$ | 20 | 32,33,34 |

Footnotes
1. The starting material was prepared by reaction of 3-chloro-6-methylpyridazine with trimethyloxonium tetrafluoroborate in CH$_2$Cl$_2$ 15 hours at ambient temperature to give 3-chloro-1,6-dimethylpyridazinium tetrafluoroborate.
2. HPLC eluant MeOH/water/HOAc 15:84:1, v/v/v.
3. n.m.r. in solvent B; 1.53 (br.s, 6H); 2.62 (s, 3H); 3.6 (m, 2H); 4.14 (s, 3H); 5.15 (d, 1H); 4.85 (d, 1H); 7.05 (s, 1H); 7.55 (d, 1H); 7.85 (d, 1H).
4.(a) The starting material was obtained as follows. Reaction of 3,6-difluoropyridazine with trimethyloxonium tetrafluoroborate gave 3,6-difluoro-1-methylpyridazinium tetrafluoroborate.
(b) To this compound (1.5 mmole) in acetonitrile (5 ml) was added a solution of allylamine (1.5 mmole) in acetonitrile (3 ml) and NaHCO$_3$. After 2 hours at ambient temperature the mixture was filtered, and the filtrate was evaporated to yield an oil, which crystallised to give 3-fluoro-1-methyl-6-(allylamino)pyridazinium tetrafluoroborate.
5. HPLC eluant MeOH/water/HOAc 25:74:1 v/v/v.
6. n.m.r. in solvent B: 1.56 (br.s, 6H); 3.55 (m, 2H); 3.78 (s, 3H); 4.0 (m, 2H); 3.95 (d, 1H); 4.5 (d, 1H); 5.15 (m, 3H); 5.83 (m, 2H); 7.06 (s, 1H); 7.42 (s, 2H).
7. The starting material was prepared by reaction of 3,6-difluoro-1-methylpyridazinium tetrafluoroborate (Footnote 4a) with 2 equivalents of isopropylamine in acetonitrile at ambient temperature, to give 3-fluoro-1-methyl-6-isopropylamino-pyridazinium tetrafluoroborate.
8. HPLC eluant MeOH/water/HOAc 30:69:1 v/v/v.
9. n.m.r. in solvent B: 1.21 (s, 3H); 1.28 (s, 3H); 1.54 (br.s, 6H); 3.5 (m, 2H); 3.76 (s, 3H); 3.85 (d, 1H); 4.0 (m, 1H); 4.45 (d, 1H); 5.15 (d, 1H); 5.83 (d, 1H); 7.05 (s, 1H); 7.4 (d, 1H); 7.67 (d, 1H).
10. The starting material was prepared as follows. To a stirred solution of 3,6-difluoro-1-methylpyridazinium tetrafluoroborate (2.00 mmoles, Footnote 4a) in acetonitrile under argon at room temperature was added MgO (2.0 mmoles) followed by a solution of dimethylamine in toluene (4.0 mmoles). After 2 hours, the mixture was filtered, and the filtrate was evaporated to an oil, which crystallised after trituration with ether, to give 3-fluoro-1-methyl-6-(N,N-dimethylamino)-pyridazinium tetrafluoroborate.
11. HPLC eluant MeOH/water/HOAc 22.5:77.5:1 v/v/v
12. n.m.r. in solvent B: 1.53 (br.s, 6H); 3.06 (s, 6H); 3.45 (d, 1H); 3.7 (d, 1H); 3.89 (s, 3H); 4.05 (d, 1H); 4.5 (d, 1H); 5.13 (d, 1H); 5.80 (d, 1H); 7.05 (s, 1H); 7.32 (d, 1H); 7.52 (d, 1H).
13. The starting material was prepared by the method described in Footnote 7, using p-nitrobenzylamine, to give 3-fluoro-1-methyl-6-(p-nitrobenzylamino)pyridazinium tetrafluoroborate.
14. HPLC eluant MeOH/water/HOAc 35:64:1 v/v/v.
15. n.m.r. in solvent B: 1.53 (br.s, 6H); 3.5 (m, 2H); 3.86 (s, 3H); 3.95 (d, 1H); 4.45 (d, 1H); 5.14 (d, 1H); 5.8 (d, 1H); 7.05 (s, 1H); 7.36 (br.s, 2H); 7.62 (d, 2H); 8.18 (d, 2H).
16. The starting material was prepared by the method described in Footnote 4 to give 3-fluoro-1-methyl-6-(2-thenylamino)pyridazinium tetrafluoroborate.
17. HPLC eluant MeOH/aqueous ammonium carbonate (2 g/l) 30:70 v/v.
18. n.m.r. in solvent B: 1.53 (s, 6H); 3.55 (m, 2H); 3.93 (s, 3H); 3.95 (d, 1H); 4.45 (d, 1H); 4.95 (s, 2H); 5.15 (d, 1H); 5.8 (d, 1H); 7.05 (s, 1H); 6.97–7.7 (m, 5H).
19. The starting material was prepared by the method described in Footnote 4 using N-Boc ethylene diamine.
20. HPLC eluant MeOH/aqueous ammonium carbonate (2 g/l), 30:70 v/v.
21. Cleavage of the Boc protecting group was achieved after the HPLC by treatment with TFA for 5 minutes.
22. n.m.r. in solvent B: 1.56 (s, 6H); 3.1 (m, 2H); 3.85 (m, 4H); 3.94 (s, 3H); 4.64 (m, 2H); 5.27 (d, 1H); 5.98 (d, 1H); 7.06 (s, 1H); 8.05 (d, 1H); 8.85 (d, 1H).
23. The starting material was prepared by a slow addition of a solution of ethanolamine in acetonitrile under argon, followed by NaHCO$_3$. After 1 hour at ambient temperature the mixture was filtered, and the filtrate was evaporated to an oil, which crystallised to give 3-fluoro-6-(2-hydroxyethylamino)-1-methyl pyridazinium tetrafluoroborate.
24. HPLC eluant MeOH/water/HOAc 20:79:1 v/v/v.
25. n.m.r. in solvent B: 1.53 (s, 6H); 3.54 (m, 6H); 3.73 (s, 3H); 3.95 (d, 1H); 4.4 (d, 1H); 5.1 (d, 1H); 5.8 (d, 1H); 7.06 (s, 1H); 7.35 (d, 1H); 7.55 (d, 1H).
26. The starting material, 3-fluoro-6-(2-methoxyethylamino)-1-methyl-pyridazinium tetrafluoroborate was prepared by the method described in Footnote 7 using 2-methoxyethylamine.
27. HPLC eluant MeOH/water/HOAc 25:74:1 v/v/v.
28. n.m.r. in solvent B: 1.53 (s, 6H); 3.23 (s, 3H); 3.5 (m, 6H); 3.73 (s, 3H); 3.95 (d, 1H); 4.5 (d, 1H); 5.15 (d, 1H); 3.85 (d, 1H); 7.07 (s, 1H); 7.4 (d, 1H); 7.7 (d, 1H).
29. The starting material was obtained by reaction of 3,6-difluoro-1-methylpyridazinium tetrafluoroborate (Footnote 4a) with sodium thiomethylate in acetonitrile for 1 hour at ambient temperature to give 3-fluoro-1-methyl-6-methylthiopyridazinium tetrafluoroborate.
30. The crude condensation product was purified by chromatography on Diaion HP20 resin, eluting with increasing proportions of MeOH in water.
31. n.m.r. in solvent B: 1.54 (br.s, 6H); 2.76 (s, 3H); 3.56 (m, 2H); 4.07 (s, 3H); 4.02 (d, 1H); 4.55 (d, 1H); 5.15 (d, 1H); 5.85 (d, 1H); 7.06 (s, 1H); 7.6 (d, 1H); 7.95 (d, 1H).
32. The starting material was prepared by the method described in Footnote 7, using 2-acetamido-1-mercaptoethane to give 3-fluoro-1-methyl-6-(2-acetamidoethylthio)pyridazinium tetrafluoroborate as a paste.
33. HPLC eluant MeOH/water/HOAc 25:74:1 v/v/v.
34. n.m.r. in solvent B: 1.54 (s, 6H); 1.83 (s, 3H); 3.2–3.8 (m, 6H); 4.0 (s, 3H); 4.6 (m, 2H); 5.19 (d, 1H); 5.85 (d, 1H); 7.0 (s, 1H); 7.93 (s, 2H).

EXAMPLES 172–178

The general process described in Example 1 was repeated using the appropriate 3-aminomethylcephalosporin derivative and the appropriate heterocycle. The following compounds were obtained:

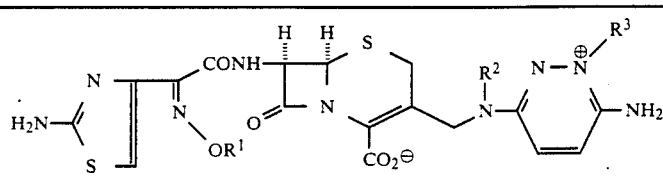

| Example No. | R$^1$ | R$^2$ | R$^3$ | Yield | Footnote |
|---|---|---|---|---|---|
| 172 | —CH$_3$ | —H | —CH$_3$ | 30 | 1,2,3 |
| 173 | —CH$_2$CH$_2$Cl | —H | —CH$_3$ | 24 | 1,4,5 |
| 174 | —C(CH$_3$)$_2$CO$_2$H | —H | 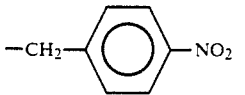 | 14 | 6,7,8 |

-continued

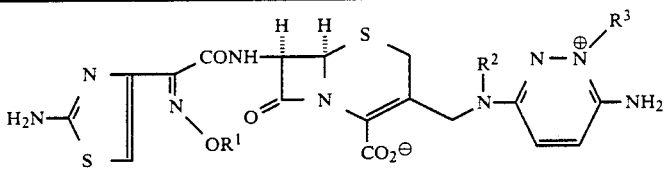

| Example No. | R¹ | R² | R³ | Yield | Footnote |
|---|---|---|---|---|---|
| 175 | " | —H | —CH₂CH=CH₂ | 18 | 9,10,11 |
| 176 | " | —H | —CH₂-C₆H₄-CF₃ | 23 | 12,13,14 |
| 177 | cyclobutyl-CO₂H | —C₂H₅ | —CH₃ | 12 | 1,15,16 |
| 178 | cyclopentyl-CO₂H | —H | —CH₃ | 32 | 1,17,18 |

Footnotes
1. The starting material was 6-amino-3-fluoro-1-methylpyridazinium tetrafluoroborate see Example 13, Footnote 16.
2. HPLC eluant MeOH/water/HOAc, 15:84:1 v/v/v.
3. n.m.r. in solvent B: 3.25–3.8 (m, 2H); 3.7 (s, 3H); 4.0 (s, 3H); 3.8 (d, 1H); 4.5 (d, 1H); 5.12 (d, 1H); 5.76 (d, 1H); 7.05 (s, 1H); 7.25 (s, 2H).
4. HPLC eluant MeOH/water/HOAc, 20:79:1, v/v/v.
5. n.m.r. in solvent B: 3.55 (m, 2H); 3.7 (s, 3H); 3.9–4.4 (m, 6H); 5.15 (d, 1H); 5.76 (d, 1H); 7.05 (s, 1H); 7.3 (s, 2H).
6. The starting material may be prepared as follows: 3,6-difluoropyridazine was mixed with a solution of ammonia (10 equivalents) in ethanol, and heated in a sealed tube for 3 hours at 80°–85° C. The solvent was evaporated and 6-amino-3-fluoropyridazine was extracted from the residue with EtOAc in a Soxhlet apparatus for 3.5 hours. This compound in EtOH was further treated with p-nitrobenzyl bromide for 2.5 hours at 40° C. The solvent was evaporated and the residue was washed twice with anhydrous ether, to give 6-amino-3-fluoro-1-(4-nitrobenzyl)-pyridazinium bromide.
7. HPLC eluant MeOH/water/HOAc, 35:64:1, v/v/v.
8. n.m.r. in solvent B: 1.57 (br.s., 6H); 3.5 (m, 2H); 4.0 (d, 1H); 4.45 (d, 1H); 5.15 (d, 1H); 5.45 (br.s, 2H); 5.87 (d, 1H); 7.1 (s, 1H); 7.47 (s, 2H); 7.65 (d, 2H); 8.35 (d, 2H).
9. The starting material may be prepared as follows: 6-amino-3-fluoropyridazine (2.5 mmoles; Footnote 6), and 2 ml of allyl bromide in the minimum of nitromethane were heated to 60° C. for 3 hours. Evaporation of the solvent, washing of the residue with ether and drying under vacuum over P₂O₅ gave 1-allyl-6-amino-3-fluoropyridazinium bromide.
10. HPLC eluant MeOH/water/HOAc, 30:69:1, v/v/v.
11. n.m.r. in solvent B: 1.6 (br.s, 6H); 3.57 (m, 2H); 3.8–4.9 (m, 4H); 5.1–5.45 (m, 3H); 5.85 (m, 2H); 7.17 (s, 2H); 7.4 (s, 2H).
12. The starting material was prepared as follows: 6-amino-3-fluoropyridazine (1.15 mmoles; Footnote 6) and alpha'-chloro-alpha,alpha,alpha-trifluoro-m-xylene in the minimum of DMF were heated to 60° C. for 4 hours. Evaporation of the solvent and trituration of the residue with anhydrous ether gave 6-amino-3-fluoro-1-(3-trifluoromethylbenzyl)-pyridazinium chloride.
13. HPLC eluant MeOH/water/HOAc, 45:54:1, v/v/v.
14. n.m.r. in solvent B: 1.54 (s, 6H); 3.5 (m, 2H); 4.03 (d, 1H); 4.45 (d, 1H); 5.11 (d, 1H); 5.43 (d, 1H); 5.9 (d, 1H); 7.1 (s, 1H); 7.45 (s, 2H); 7.62–7.95 (m, 4H).
15. HPLC eluant MeOH/water/HOAc, 25-30:74-69:1 v/v/v.
16. n.m.r. in solvent B: 1.07 (t, 3H); 1.9–3.0 (m, 6H); 3.46 (m, 4H); 4.25 (d, 1H); 4.6 (d, 1H); 5.2 (d, 1H); 5.86 (d, 1H); 6.98 (s, 1H); 7.4 (d, 1H); 7.76 (d, 2H).
17. HPLC eluant MeOH/water/HOAc, 25-30:74-69:1 v/v/v.
18. n.m.r. in solvent B: 1.72 (m, 4H); 2.15 (m, 4H); 3.55 (m, 2H); 3.7 (s, 3H); 4.05 (d, 1H); 4.55 (d, 1H); 5.15 (d, 1H); 5.83 (d, 1H); 7.06 (s, 1H); 7.3 (s, 2H).

EXAMPLES 179–180

The process described in Example 1 was repeated, using the appropriate heterocycle as starting material, to give the following compounds:

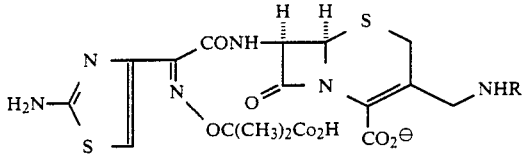

| Example No. | R | Yield % | Footnotes |
|---|---|---|---|
| 179 | tetrahydrocinnolinyl-N-methyl group | 15 | 1,2,3,4 |
| 180 | 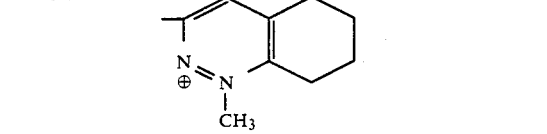 | 9 | 5,6,7,8 |

1. The starting material was obtained by reaction of 3-chloro-5,6,7,8-tetrahydrocinnoline (see Journal of Org. Chemistry 1955, Vol. 20, p.707) with trimethyloxonium tetrafluoroborate in CH₂Cl₂ overnight.
2. The condensation was performed in water at pH 7.6 (ambient temperature) with NaHCO₃ as base.
3. HPLC eluant, MeOH/water/HOAc, 30-40:69-59:1, v/v/v.
4. n.m.r. in solvent B: 1.54 (s, 6H); 1.86 (m, 4H); 2.81 (m, 4H); 3.60 (br.s, 2H); 3.96 (s, 3H); 4.55 (br.s, 2H); 5.16 (d, 1H); 5.88 (d, 1H); 7.04 (s, 1H); 7.73 (s, 1H).
5. The starting heterocycle may be prepared as follows: To a stirred solution of 7,7-dichlorobicyclo[3,2,0]heptan-6-one (see Tetrahedron, 1971, Vol.27, p.615) (52.7 mmoles) in MeOH (25 ml) at 0° C. was added dropwise hydrazine hydrate (3.3 ml.). Stirring was continued at 0° C. for 0.75 hours, the solvent was evaporated, the residue was taken up in water and extracted with CH₂Cl₂, and the organic phases were combined, washed with water and dried (MgSO₄). Evaporation of the solvent gave cis-1,1-dichloromethylcyclopentane carbohydrazide (yield 54%) having the following n.m.r. in CDCl₃: 2.0 (m, 6H); 2.8 (m, 2H); 3.92 (br.s, 2H); 5.96 (d, 1H); 7.0 (br.s, 1H).
The above hydrazide (28.7 mmoles) was dissolved in aqueous EtOH (40 ml.; 3:1 v/v) and heated at reflux for 1.75 hours. The reaction mixture was diluted with water and extracted with CH₂Cl₂. The combined CH₂Cl₂ extracts were washed with water and dried (MgSO₄), the solvent was evaporated to a small volume and ether was added to give 4,5-dihydro-4,5-trimethylenepyridazin-3(2H)-one (yield 87%). N.m.r. in CDCl₃: 1.5-2.4 (m, 6H); 2.6-3.0 (m, 2H); 6.95 (d, 1H); 7.7 (br.s, 1H). This dihydropyridazinone derivative (17.7 mmoles) was dissolved in HOAc (15 ml.) and bromine (17.6 mmoles) was added slowly with stirring. The reaction mixture was then heated 0.4 hours at 100° C., cooled and the HOAc evaporated. The residue was taken up in water and the pH adjusted to 10 with 12N NaOH. After stirring for 3 hours at room temperature, the reaction mixture was extracted with CH₂Cl₂, the combined CH₂Cl₂ extracts were washed with water, dried (MgSO₄), and the solvent was evaporated. The crude product was applied to a column of Kieselgel 60 (120 g). Elution with ether-MeOH, 5-7:95-93 v/v, gave 4,5-trimethylenepyridazin-3(2H)-one in 24% yield. N.m.r. in CDCl₃: 2.13 (q, 2H); 2.91 (t, 4H); 7.78 (s, 1H).

The above pyridazinone derivative (13.5 mmoles) was treated with 15 ml. of phosphorus oxychloride at 80° C. for 2 hours. After evaporation to dryness, the residue was taken up in water, neutralised with NaHCO₃ and extracted with CH₂Cl₂. The CH₂Cl₂ was evaporated and the residue was applied to a column of Kieselgel 60 (50 g). Elution with ether/MeOH, 95:5 v/v, gave 3-chloro-4,5-trimethylenepyridazine (yield 42%). N.m.r. in CDCl₃: 2.2 (q, 2H); 3.06 (t, 2H); 3.08 (t, 2H); 9.02 (s, 1H).

This compound was then treated with trimethyloxonium tetrafluoroborate in CH₂Cl₂ at ambient temperature for 0.5 hour to give a 9:1 mixture of 1-methyl and 2-methyl-4,5-trimethylenepyridazinium tetrafluoroborate in 90% yield. N.m.r. in CDCl₃ of the 1-methyl derivative is: 2.39 (q, 2H); 3.26 (t, 2H); 3.43 (t, 2H); 4.59 (s, 3H); 9.51 (s, 2H).
6. The condensation was performed in DMF/water at 60° C. for 6 hours in the presence of NaHCO₃.
7. HPLC eluant:MeOH/water/HOAc, 25:74:1, v/v/v.
8. n.m.r. in solvent B: 1.51 (s, 3H); 1.54 (s, 3H); 2.17 (m, 2H); 2.9 (m, 4H); 3.52 (m, 2H); 4.21 (s, 3H); 4.67 (m, 1H); 4.84 (m, 1H); 5.1 (d, 1H); 5.82 (d, 1H); 7.05 (s, 1H); 8.95 (s, 1H).

EXAMPLES 181-191

The general process described in Example 1 was repeated using the appropriate 3-aminomethyl-cephalosporin derivative and the appropriate heterocycle. The following compounds were obtained:

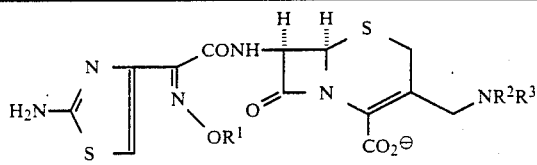

| Example No. | R¹ | R² | R³ | Yield % | Footnote |
|---|---|---|---|---|---|
| 181 | —C(CH₃)₂CO₂H | H | 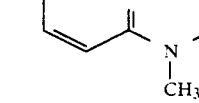 | 13 | 1,2,3 |
| 182 | —C(CH₃)₂CO₂H | H | 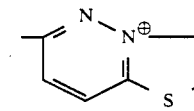 | 20 | 4,5,6 |
| 183 | " | Et | 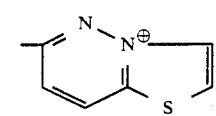 | 24 | 4,7,8 |
| 184 |  | Et | 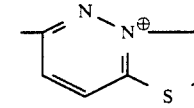 | 31 | 4,9,10 |
| 185 |  | H | 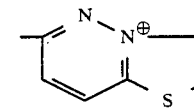 | 60 | 4,11,12 |
| 186 | —C(CH₃)₂CO₂H | H | 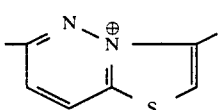 | 27 | 13,14,15 |
| 187 | " | Et | 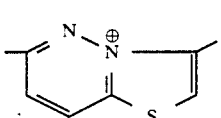 | 36 | 13,16,17 |
| 188 |  | H | 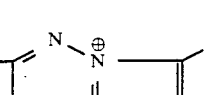 | 54 | 13,18,19 |

-continued

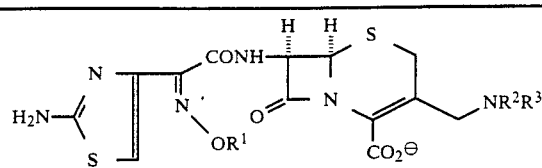

| Example No. | R¹ | R² | R³ | Yield % | Footnote |
|---|---|---|---|---|---|
| 189 | —C(CH₃)₂CO₂H | H | (imidazo[1,2-b]pyridazinium, N-CH₃) | 35 | 20,21,22 |
| 190 | (cyclopentyl)-CO₂H | H | (triazolo-pyridazinium, N-CH₃) | | 23,24,25 |
| 191 | " | H | (thieno-pyrimidinium, N⁺-CH₃) | | 26,27,28 |

1. 6-Fluoro-2,3-dihydro-1H-imidazo(1,2,3)-pyridazinium bromide was prepared according to the procedure described in Croat. Chem. Acta 41, 135 (1969) using 3,6-difluoropyridazine as starting material. The hydrobromide salt in MeOH was further treated with diazomethane to liberate the free base, 6-fluoro-2,3-dihydroimidazo(1,2-b)pyridazine. Upon evaporation of the MeOH, the compound was dissolved in CH₂Cl₂/nitromethane (5:3 v/v) and trimethyloxonium tetrafluoroborate was added to the reaction mixture. After 4 hours at ambient temperature, the mixture was filtered, and the filtrate was evaporated to give 6-fluoro-2,3-dihydro-1-methylimidazo(1,2-b)pyridazinium tetrafluoroborate.
2. HPLC eluant, MeOH/water/HOAc, 25:74:1 v/v/v.
3. n.m.r. in solvent B: 1.54 (s, 6H); 2.99 (s, 3H); 3.2–4.6 (m, 8H); 5.13 (d, 1H); 5.82 (d, 1H); 7.05 (s, 1H); 7.4 (d, 1H); 7.5 (d, 1H).
4. The starting material was 6-chloro-thiazolo[3,2-b]pyridazinium perchlorate, (see J. Org. Chem. 34, 996, (1969)).
5. HPLC eluant, MeOH/water/HOAc, 20:79:1, v/v/v.
6 n.m.r. in solvent B: 1.55 (s, 6H); 3.3 (d, 1H); 3.55 (d, 1H); 3.95 (d, 1H); 4.4 (d, 1H); 5.15 (d, 1H); 5.55 (d, 1H); 7.45 (d, 1H); 8.47–8.6 (m, 3H).
7. The product was purified by chromatography on Diaion HP20 resin, eluting with increasing proportions of CH₃CN in water.
8. n.m.r. in solvent B: 1.16 (br t, 3H); 1.51 (s, 6H); 3.5 (m, 2H); 3.6 (m, 2H); 4.45 (d, 1H); 3.65 (d, 1H); 5.18 (d, 1H); 5.85 (d, 1H); 7.0 (s, 1H); 7.9 (d, 1H); 8.54 (d, 1H); 8.66 (d, 1H); 8.7 (d, 1H).
9. HPLC eluant, MeOH/water/HOAc, 20-30:79-69:1 v/v/v.
10. n.m.r. in solvent B: 1.15 (br t, 3H); 1.91–2.4 (m, 6H); 3.6 (m, 4H); 4.5 (d, 1H); 4.8 (d, 1H); 5.17 (d, 1H); 5.85 (d, 1H); 6.98 (s, 1H); 7.85 (d, 1H); 8.65 (d, 1H); 8.5 (d, 1H); 8.6 (d, 1H).
11. HPLC eluant, MeOH/water/HOAc, 30:69:1, v/v/v.
12. n.m.r. in solvent B: 1.7 (m, 4H); 2.1 (m, 4H); 3.5 (d, 1H); 3.7 (d, 1H); 4.1 (d, 1H); 4.6 (d, 1H); 5.14 (d, 1H); 5.84 (d, 1H); 7.04 (s, 1H); 7.45 (d, 1H); 8.6 (d, 1H); 8.47 (d, 1H); 8.52 (d, 1H).
13. The starting material was 6-chloro-3-methylthiozolo[3,2-b]pyridazinium perchlorate (see J. Org. Chem. 34, 996, (1964)).
14. HPLC eluant, MeOH/water/HOAc, 25:74:1, v/v/v.
15. n.m.r. in solvent B: 1.52 (s, 3H); 1.54 (s, 3H); 3.55 (m, 2H); 4.1 (d, 1H); 4.65 (d, 1H); 5.15 (d, 1H); 5.85 (d, 1H); 7.0 (s, 1H); 7.47 (d, 1H)); 8.62 (d, 1H); 8.23 (s, 1H).
16. HPLC eluant, MeOH/water/HOAc, 30:69:1, v/v/v.
17. n.m.r. in solvent B: 1.15 (br.t 3H); 1.5 (br 6H); 2.51 (s, 3H); 3.4 (q, 2H); 3.65 (m, 2H); 4.5 (d, 1H); 4.8 (d, 1H); 5.17 (d, 1H); 5.87 (d, 1H); 7.0 (s, 1H); 7.87 (d, 1H); 8.64 (d, 1H); 8.2 (s, 1H).
18. HPLC eluant MeOH/water/HOAc, 30:69:1, v/v/v.
19. n.m.r. in solvent B: 1.7 (m, 4H); 2.1 (m, 4H); 2.52 (s, 3H); 3.56 (d, 1H); 3.6 (d, 1H); 4.3 (d, 1H); 4.6 (d, 1H); 5.15 (d, 1H); 5.86 (d, 1H); 7.04 (s, 1H); 7.47 (d, 1H); 8.61 (d, 1H); 8.61 (d, 1H); 8.22 (s, 1H).
20. The starting material was prepared by treating 6-fluoroimidazo(1,2-b)pyridazine, (obtained by a process described in Tetrahedron, 23, 387 (1967), with trimethyloxonium tetrafluoroborate in CH₂Cl₂ at ambient temperature for 5 hours. The precipitate was filtered, to give 6-fluoro-1-methylimidazo(1,2-b)pyridazinium tetrafluoroborate.
21. HPLC eluant, MeOH/water/HOAc, 20:79:1, v/v/v.
22. n.m.r. in solvent B: 1.56 (br.s, 6H); 3.61 (m, 2H); 3.98 (s, 3H); 4.1 (d, 1H); 4.6 (d, 1H); 5.15 (d, 1H); 5.83 (d, 1H); 7.02 (s, 1H); 7.31 (d, 1H); 8.04 (d, 1H); 8.09 (d, 1H); 8.21 (d, 1H).
23. For starting material see Example 229, Footnote 2.
24. HPLC eluant was MeOH/water/HOAc, 25:74:1, v/v/v.
25. n.m.r. in solvent B: 1.7 (m, 4H); 2.14 (m, 4H); 3.48 (d,·1H); 3.7 (d, 1H); 4.15 (s, 3H); 4.14 (d, 1H); 4.45 (d, 1H); 5.14 (d, 1H); 5.85 (d, 1H); 7.05 (s, 1H); 7.52 (d, 1H); 8.35 (d, 1H); 9.47 (s, 1H).
26. For starting material, see Example 222, Footnote 5.
27. HPLC eluant was MeOH/water/HOAc, 30:69:1, v/v/v.
28. n.m.r. in solvent B: 1.7 (m, 4H); 2.15 (m, 4H); 2.44 (d, 1H); 2.65 (d, 1H); 4.05 (s, 3H); 4.55 (d, 1H); 4.95 (d, 1H); 5.15 (d, 1H); 5.82 (d, 1H); 7.05 (s, 1H); 7.92 (s, 2H); 8.9 (s, 1H.

EXAMPLE 192

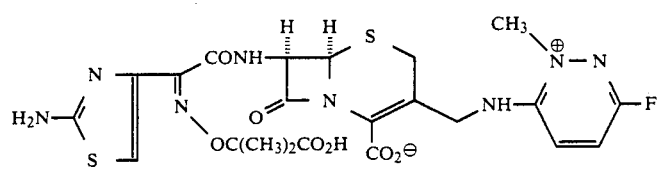

The starting material was 3-fluoro-6-methoxy-1-methyl-pyridazinium tetrafluoroborate, which was obtained by treatment of 6-fluoro-2-methylpyridazin-3-one with trimethyloxonium tetrafluoroborate in CH₂CL₂ at ambient temperature.

The condensation reaction was carried out in DMF/water in the presence of NaHCO₃ at ambient temperature for 0.5 hours. Yield 12%.

HPLC eluant, MeOH/water/HOAc, 25:74:1, v/v/v.
n.m.r. in solvent B: 1.54 (s, 6H); 3.6 (br.s, 2H); 3.93 (s, 3H); 3.45 (d, 1H); 3.85 (d, 1H); 5.16 (d, 1H); 5.88 (d, 1H); 7.04 (s, 1H); 7.98–8.17 (m, 2H).

EXAMPLE 193

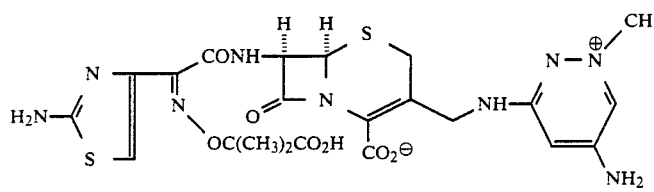

This compound was obtained as follows: To 5-amino-3-chloropyridazine (see Yakugaku Zasshi 82, 857–60, (1962); Chem. Abstracts 59, 1631j) in nitromethane was added trimethyloxonium tetrafluoroborate. After 3 hours at ambient temperature the solvent was evaporated, and the ether was added to give a mixture of 5-amino-3-chloro-1-methylpyridazinium and 5-amino-3-chloro-2-methylpyridazinium tetrafluoroborates, which were used without further separation. The standard procedure was used for the condensation, which was carried out in a DMF/water mixture in the presence of $NaHCO_3$ at 70° C. for 1.25 hours. The final compound was worked up by HPLC using MeOH/water/HOAc, 22.5:76.5:1 v/v/v, as eluant. Yield 25%. n.m.r. of the single isomer product in solvent B: 1.53 (br.s, 6H); 3.59 (m, 2H); 3.83 (s, 3H); 4.56 (m, 2H); 5.15 (d, 1H); 5.9 (d, 1H); 6.23 (d, 1H); 7.0 (s, 1H); 7.92 (d, 1H).

EXAMPLES 194–195

The general process described in Example 1 was repeated, using the appropriate 3-aminomethylcephalosporin derivative and the appropriate heterocycle, to give the following compounds:

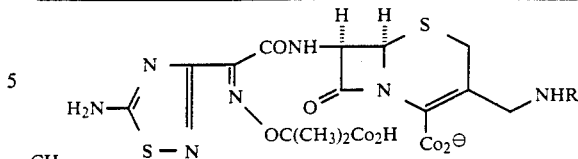

| Example No. | R | Yield % | Footnotes |
|---|---|---|---|
| 194 | ![pyridazinium-thio] | 37 | 1,2,3 |
| 195 | ![methylpyridazinium-amino] | 23 | 4,5,6 |

Footnotes:
1. For the quaternary heterocyclic starting material, see Example 182, Footnote 4.
2. HPLC eluant, MeOH/water/HOAc, 20–25:79–74:1, v/v/v.
3. n.m.r. in solvent B: 1.48 (s, 6H); 3.45 (d, 1H); 3.71 (d, 1H); 4.11 (d, 1H); 4.57 (d, 1H); 5.12 (d, 1H); 5.84 (d, 1H); 7.46 (d, 1H); 8.47 (d, 1H); 8.57 (d, 2H).
4. For the quarternary heterocyclic starting material, see Example 13, Footnote 6.
5. HPLC eluant, MeOH/water/HOAc, 20:79:1, v/v/v.
6. n.m.r. in solvent B: 1.47 (s, 6H); 3.5 (m, 2H); 3.6 (s, 3H); 3.91 (d, 1H); 4.42 (d, 1H); 5.09 (d, 1H); 5.83 (d, 1H); 7.26 (s, 2H).
7. The 3-aminomethyl cephalosporin starting material was obtained by adding the corresponding known 3-azidomethyl cephalosporin derivative to 90% v/v aqueous TFA and stirring for 3 hours at ambient temperature. After cooling at 0°, Raney nickel (wet-2.0 g) was added and the mixture was stirred for 0.5 hours at 0° and 1 hour at ambient temperature. The mixture was filtered, the filtrate evaporated and the crude product purified by chromatography on a Diaion HP 20 column, eluting with increasing proportions of acetonitrile in water. Appropriate fractions were combined, evaporated to a small volume and freeze-dried to give the required compound (0.81 g; yield 43%) having the following n.m.r. in solvent B: 1.49 (s, 6H); 3.5–4.0 (m, 4H); 5.18 (d, 1H); 5.9 (d, 1H).

EXAMPLES 196–218

The general procedure described in Examples 1–4 was used, except that the reaction was carried out at ambient temperature for 5 hours before quenching with HOAc. The appropriate 3-aminomethylcephalosporin was used, the reactions were worked up by chromatography on Diaion CHP20P resin to purify. The following compounds were made:

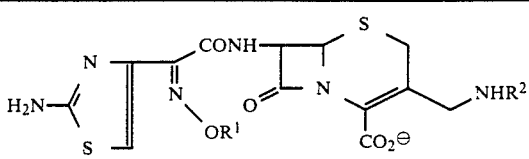

| Example No. | $R^1$ | $R^2$ | Yield % | Footnotes |
|---|---|---|---|---|
| 196 | $CH_2CO_2H$ | ![methylpyridazinium] | 46 | 1,2 |

-continued

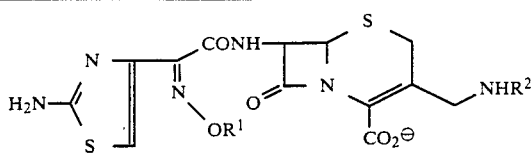

| Example No. | R¹ | R² | Yield % | Footnotes |
|---|---|---|---|---|
| 197 | $CH_2CO_2H$ | (pyrido-thiazolium bicyclic) | 40 | 3,4 |
| 198 | $CH_3$<br>$\|$<br>$CHCO_2H$<br>(m.p. isomer) | (N-methyl pyridazinium) | 34 | 1,5,6 |
| 199 | $CH_3$<br>$\|$<br>$CHCO_2H$<br>(l.p. isomer) | (N-methyl pyridazinium) | 40 | 1,6,7 |
| 200 | $CH_3$<br>$\|$<br>$CH-CO_2H$<br>(m.p. isomer) | (pyrido-thiazolium bicyclic) | 28 | 3,6,8 |
| 201 | $CH_3$<br>$\|$<br>$CH-CO_2H$<br>(l.p. isomer) | (pyrido-thiazolium bicyclic) | 22 | 3,6,9 |
| 202 | (cyclobutyl)$CO_2H$ | (pyrido-thiazolium bicyclic) | 29 | 3,10 |
| 203 | (cyclobutyl)$CO_2H$ | (N-methyl aminopyridazinium)$NH_2$ | 20 | 11,12 |
| 204 | $CH_2CONHCH_3$ | (N-methyl pyridazinium) | 67 | 1,13,14 |
| 205 | $CH_2CON(CH_3)_2$ | (N-methyl pyridazinium) | 64 | 1,15,16 |
| 206 | $CH_2CONHCH_2CF_3$ | (N-methyl pyridazinium) | 57 | 1,17,18 |

-continued

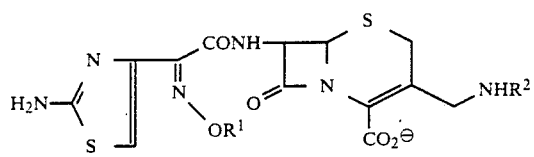

| Example No. | R¹ | R² | Yield % | Footnotes |
|---|---|---|---|---|
| 207 | ![structure with NH and O] | N-N⁺(CH₃) pyridazinium | 69 | 1,19,20 |
| 208 | $C_2H_5$ | N-N⁺(CH₃) pyridazinium with $NH_2$ | 18 | 11,21 |
| 209 | $\begin{array}{c}CH_2CH_3\\ -CH-CO_2H\end{array}$ (m.p. isomer) | N-N⁺(CH₃) pyridazinium | 60 | 1,22,23 |
| 210 | $\begin{array}{c}CH_2CH_3\\ CH-CO_2H\end{array}$ (l.p. isomer) | N-N⁺(CH₃) pyridazinium | 46 | 1,23,24 |
| 211 | cyclopentyl-$CO_2H$ | thiazolo-pyrimidinium | 33 | 3,25 |
| 212 | cyclopentyl-$CO_2H$ | thiazolo-pyrimidinium | 69 | 26,27 |
| 213 | cyclobutyl-$CO_2H$ | pyridinium-$CH_2$-C=C(CN)(N)S | 57 | 28,29 |
| 214 | cyclobutyl-$CO_2H$ | pyridinium-$CH_2$-C=C(N=N)S (thiadiazole) | 56 | 30,31 |
| 215 | $\begin{array}{c}CH_3\\ -CHCO_2H\end{array}$ (m.p. isomer) | pyridinium-$CH_2$-C=C(N=N)S | 53 | 30,32 |
| 216 | $\begin{array}{c}CH_2CH_3\\ -CHCO_2H\end{array}$ (m.p. isomer) | pyridinium-$CH_2$-C=C(N=N)S | 61 | 30,33 |

-continued

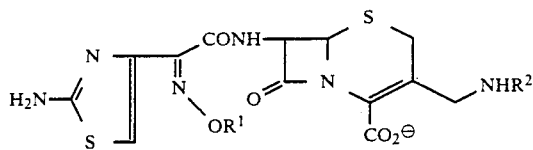

| Example No. | $R^1$ | $R^2$ | Yield % | Footnotes |
|---|---|---|---|---|
| 217 | —CH(CH₂CH₃)CO₂H (m.p. isomer) | pyridinium-CH₂-C(CH₃)=CH-CN | 42 | 34,35 |
| 218 | cyclopentyl-CO₂H | N–N⁺(CH₃)-pyridyl | 52 | 1,36 |

Footnotes
1. Starting material was 3-chloro-1-methylpyridazinium iodide.
2. n.m.r. in solvent A: 3.36 (d, 1H), 3.59 (d, 1H); 4.08 (d, 1H); 4.24 (s, 3H); 4.48 (d, 1H); 4.53 (s, 2H); 5.03 (d, 1H); 5.71 (d, 1H); 6.8 (s, 1H); 7.6 (m, 1H); 7.88 (m, 1H); 8.88 (m, 1H).
3. Starting material was 7-methylthiothiazolo[3,2-a]pyrimidinium tetrafluoroborate.
4. n.m.r. in solvent A: 3.35 (d, 1H); 3.6 (d, 1H); 4.25 (d, 1H); 4.51 (s, 2H); 4.64 (d, 1H); 5.03 (d, 1H); 5.73 (d, 1H); 6.81 (s, 1H); 7.04 (d, 1H); 7.65 (d, 1H); 8.08 (d, 1H); 8.79 (d, 1H).
5. n.m.r. in solvent A: 1.4 (d, 3H); 3.39 (d, 1H); 3.61 (d, 1H); 4.08 (d, 1H); 4.23 (s, 3H); 4.53 (d, 1H); 4.6 (q, 1H); 5.06 (d, 1H); 5.8 (d, 1H); 6.81 (s, 1H); 7.6 (m, 1H); 7.93 (m, 1H); 8.9 (m, 1H). Retention time 3.6 minutes on a reversed phase Partisil 10/25 ODS-2 column, using MeOH/H₂O/TFA, 35:65:0.2, v/v/v as eluant.
6. The 3-aminomethylcephalosporin may be prepared as follows: To a stirred suspension of 2-(2-formamidothiazol-4-yl)-2-oxoacetic acid (6.1 g) in DMF (50 ml) was added pyridine (2.65 ml) and 4N aqueous hydrochloric acid (8.52 ml.), followed by dropwise addition of t-butyl 2-aminoxypropionate (5.28 g). After stirring for 18 hours at ambient temperature, the mixture was diluted with water, acidified, and worked up in a conventional manner by extraction into EtOAc. Crude product was dissolved in a mixture of ether (80 ml) and EtOAc (40 ml), and N-methylmorpholine (7.6 ml) added. The precipitate was filtered to give 2-[(Z)-1-(tert-butoxycarbonyl)ethoxyimino]-2-(2-formamidothiazol-4-yl)acetic acid as its N-methyl- morpholine salt, having the following n.m.r. in d₆DMSO: 1.35 (d, 3H); 1.41 (s, 9H); 2.35 (s, 3H); 2.56 (t, 4H); 3.65 (t, 4H); 4.55 (q, 1H); 7.35 (s, 1H); 8.46 (s, 1H).
Oxalyl chloride (2.61 ml) and DMF (2.3 ml) were added to CH₂Cl₂ (100 ml) at −10° C., and stirred for 30 minutes. The above N-methylmorpholine salt (12.06 g) was added, followed by N-methylmorpholine (0.60 ml), and stirring continued for 30 minutes. Meanwhile, in a separate flask, a suspension of 7-amino-3-azidomethylceph-3-em-4-carboxylic acid (7.27 g) in CH₂Cl₂ (40 ml) was treated with N,O-bis(trimethylsilyl)acetamide (14.1 ml), and stirred for 1 hour to give a clear solution, which was transferred by syringe to the acid chloride solution. After stirring for 1 hour at −10° C., the temperature was allowed to come to ambient. The mixture was poured into water (100 ml) and organics extracted into EtOAc. Removal of solvent gave 3-azidomethyl-7-[2-((Z)-1-(t-butoxycarbonyl)ethoxyimino)-2-(2-formamidothiazol-4-yl)-acetamido]ceph-3-em-4-carboxylic acid, as a mixture of diastereoisomers, having the following n.m.r. in solvent A: 1.35 (s, 9H); 1.37 and 1.38 (2×d, 3H), 3.41 (2×d, 1H); 3.61 (d, 1H); 3.82 (2×d, 1H); 4.34 (d, 1H); 4.56 (2×q, 1H); 5.14 (2×d, 1H); 5.83 (d, 1H); 7.32 (2×s, 1H); 8.39 (s, 1H).
A solution of the above 3-azidomethyl compound (16.5 g) in a mixture of isopropanol (110 ml), water (20 ml) and concentrated hydrochloric acid (7.5 ml) was stirred for 3 days at ambient temperature. After cooling to 0° C., the pH was raised to 3 using triethylamine, solvents were evaporated, the residue treated with water (100 ml.) and organics extracted into EtOAc Evaporation gave 7-[2-(2-aminothiazol-4-yl)-2-((Z)-1-(t-butoxycarbonyl)ethoxyimino)acetamido]-3-azidomethylceph-3-em-4-carboxylic acid, as a mixture of diastereoisomers, having the following n.m.r. in solvent A: 1.4 and 1.42 (2×d, 3H); 1.44 (s, 9H); 3.46 (2×d, 1H); 3.66 (d, 1H); 3.88 (2×d, 1H); 4.39 (d, 1H); 4.55 (q, 1H); 5.18 (d, 1H); 5.84 (d, 1H); 6.74 (2×s, 1H).
The above deprotected 3-azidomethylcephem (12.2 g) was added to 90% v/v aqueous TFA (60 ml) precooled to 0° C., and stirred for 30 minutes. Raney nickel (wet, 2.5 g) was added, and the mixture stirred 20 minutes, allowing the temperature to rise to ambient. The mixture was filtered, solvents evaporated and the residue dissolved in water, and the pH raised to 3 with sodium acetate. Careful chromatography on Diaion HP20SS, eluting successively with water, then water/CH₃CN, 97.5:2.5 v/v and water/CH₃CN 95:5 v/v, allowed substantial separation of the two diastereoisomers of 3-aminomethyl-7-[2-(2-aminothiazol-4-yl)-2-((Z)-1-carboxyethoxyimino)acetamido]ceph-3-em-4-carboxylic acid. The more polar (m.p.) isomer, having retention time 3.05 minutes on a reversed phase Partisil PXS 10/25 ODS-2 column, using MeOH/HOAc 20:80:1 v/v/v as eluant, had the following n.m.r. in solvent A: 1.37 (d, 3H); 3.23 (d, 1H); 3.44 (d, 1H); 3.53 (d, 1H); 3.65 (d, 1H); 4.52 (q, 1H); 4.99 (d, 1H); 5.8 (d, 1); 6.79 (s, 1H).
The less polar (l.p.) isomer, having retention time 4.7 minutes under identical conditions to the above, had the following n.m.r. in solvent A: 1.43 (d, 3H); 3.2 (d, 1H); 3.42 (d, 1H); 3.53 (d, 1H); 3.64 (d, 1H); 4.52 (q, 1H); 5.0 (d, 1H); 5.72 (d, 1H); 6.81 (s, 1H). (d,
7. n.m.r. in solvent A: 1.42 (d, 3H); 3.45 (d, 1H); 3.64 (d, 1H); 4.08 (d, 1H); 4.24 (s, 3H); 4.56 (d, 1H); 4.63 (q, 1H); 5.12 (d, 1H); 5.81 (d, 1H); 6.79 (s, 1H); 7.6 (m, 1H); 7.95 (m, 1H); 8.95 (m, 1H). Retention time 4.6 min. on a reversed phase Partisil PXS 10/25 ODS-2 column, using MeOH/H₂O/TFA, 35:65:0.2 v/v/v, as eluant.
8. n.m.r. in solvent A: 1.38 (d, 3H); 3.31 (d, 1H); 3.59 (d, 1H); 4.27 (d, 1H); 4.56 (q, 1H); 4.59 (d, 1H); 5.02 (d, 1H); 5.77 (d, 1H); 6.78 (s, 1H); 7.05 (d, 1H); 7.66 (d, 1H); 8.1 (d, 1H); 8.69 (d, 1H). Retention time 3.3 minutes on a reversed phase Partisil 10/25 ODSO-2 column, using MeOH/H₂O/TFA, 40:60:0.2, v/v/v, as eluant.
9. n.m.r. in solvent A: 1.41 (d, 3H); 3.36 (d, 1H); 3.61 (d, 1H); 4.23 (d, 1H); 4.6 (m, 3H); 5.05 (d, 1H); 5.74 (d, 1H); 6.8 (s, 1H); 7.03 (d, 1H); 7.67 (d, 1H); 8.11 (d, 1H); 8.7 (d, 1H). Retention time 4.3 minutes on a reversed phase Partisil 10/25 ODS-2 column, using MeOH/H₂O/TFA, 40:60:0.2, v/v/v, as eluant.
10. n.m.r. in solvent A: 2.38 (t, 4H); 3.35 (d, 1H); 3.62 (d, 1H); 4.27 (d, 1H); 4.66 (d, 1H); 5.06 (d, 1H); 5.76 (d, 1H); 6.76 (s, 1H); 7.04 (d, 1H); 7.66 (d, 1H); 8.1 (d, 1H); 8.7 (d, 1H).
11. The basic procedure of Examples 1-4 was used, except the reaction mixture was heated at 60° C. for 2 hours, and product was isolated by chromatography on Diaion HP20SS. The starting heterocycle was 6-amino-3-fluoro-1-methylpyridazinium tetrafluoroborate.
12. n.m.r. in solvent A: 2.33 (m, 4H); 3.28 (d, 1H); 3.56 (d, 1H); 3.65 (s, 3H); 3.83 (d, 1H); 4.27 (d, 1H); 5.0 (d, 1H); 5.68 (d, 1H); 6.7 (s, 1H); 8.23 (s, 2H).
13. n.m.r. in solvent A: 2.66 (s, 3H); 3.35 (d, 1H); 3.61 (d, 1H); 4.08 (d, 1H); 4.26 (s, 3H); 4.47 (s, 2H); 4.51 (d, 1H); 5.03 (d, 1H); 5.72 (d, 1H); 6.87 (s, 1H); 7.62 (m, 1H); 7.94 (m, 1H); 8.91 (d, 1H).
14. The 3-aminomethylcephalosporin may be prepared as follows: Using the general procedure of Footnote 6 above, 2-((Z)-N-methylcarbamoylmethoxyimino)-2-(2-tritylaminothiazol-4-yl)acetic acid was condensed with 7-amino-3-azidomethylceph-3-em-4-carboxylic acid to give the appropriate 7-amido-3-azidomethylcephalosporin. This was then reduced, with accompanying removal of the trityl group, by the same general procedure to give 3-aminomethyl-7-[2-(2-aminothiazol-4-yl)-2-((Z)-N-methylcarbamoylmethoxyimino)acetamido]ceph-3-em-4-carboxylic acid, used without further characterisation in subsequent stages.
15. n.m.r. in solvent A: 2.8 (s, 3H); 2.92 (s, 3H); 3.3 (d, 1H); 3.61 (d, 1H); 4.06 (d, 1H); 4.24 (s, 3H); 4.49 (d, 1H); 4.81 (s, 2H); 5.02 (d, 1H); 5.71 (d, 1H); 6.82 (s, 1H); 7.6 (m, 1H); 7.93 (dd, 1H); 8.89 (d, 1H).
16. The 3-aminomethylcephalosporin may be prepared as follows: Using the general procedure of Footnote 6 above, 2-((Z)-N,N-dimethylcarbamoylmethoxyimino)-2-(2-tritylaminothiazol-4-yl)acetic acid was condensed with 7-amino-3-azidomethylceph-3-em-4-carboxylic acid, to give the appropriate 7-amido-3-azidomethylcephalosporin. This was reduced, by the same general procedure, to give, after chromatography on Diaion HP20SS resin and eluting with isopropanol/water, 3-aminomethyl-7-[2-(2-aminothiazol-4-yl)-2( (Z)-N,N-dimethylcarbamoylmethoxyimino)acetamido]ceph-3-em-4-carboxylic acid, used without further characterisation for subsequent stages.
17. n.m.r. in solvent A: 3.34 (d, 1H); 3.63 (d, 1H); 3.94 (m, 2H); 4.08 (d, 1H); 4.25 (s, 3H); 4.55 (d, 1H); 4.6 (s, 2H); 5.05 (d, 1H); 5.74 (d, 1H); 6.87 (s, 1H); 7.63 (m, 1H); 7.94 (dd, 1H); 8.92 (d, 1H).

18. The starting material may be obtained as follows: 2,2,2-Trifluoroethylamine hydrochloride (27.1 g) was suspended in dichloromethane (300 ml), cooled to 5°, and triethylamine (55.6 ml) was run in. A solution of bromoacetyl bromide (18 ml) in dichloromethane (200 ml) was run in over the course of 3 hours. After a conventional extractive work-up, the crude product was distilled to give N-(2,2,2-trifluoroethyl)-2-bronoacetamide, n.m.r. in CDCl$_3$: 3.93 (m, 4H); 6.9 (br, 1H).

Ethyl 2-(Z)-hydroxyimino-2-(tritylaminothiazol-4-yl)acetate hydrochloride (19.7 g) was dissolved in DMSO (150 ml), treated with potassium carbonate (15.4 g), and the above bromoacetamide (12.7 g) was added. After stirring for 24 hours, the reaction mixture was diluted with water (500 ml) and worked-up by conventional extraction. Product was purified by chromatography on silica gel, to give ethyl 2-[(Z)-N-(2,2,2-trifluoroethyl)carbamoylmethoxyimino]-2-(2-tritylaminothiazol-4-yl)acetate, n.m.r. in CDCl$_3$: 1.38 (t, 3H); 3.94 (m, 2H); 4.41 (q, 2H), 4.82 (s, 2H); 6.63 (s, 1H); 7.0 (m, 2H); 7.35 (m, 15H).

The ester was dissolved in methanol, and hydrolysed at ambient temperature by addition of aqueous sodium hydroxide. The sodium salt precipitated and was filtered off. After resuspension in water and acidification with 2N hydrochloric acid, there was obtained 2-[(Z)-N-(2,2,2-trifluoroethyl)carbamoylmethoxyimino]-2-(2-tritylaminothiazol-4-yl)acetic acid. Following the procedure outlined in Footnote 14 above, this was condensed with 7-amino-3-azidomethylceph-3-em-4-carboxylic acid, and the product was reduced, to give 3-aminomethyl-7-[2-(2-aminothiazol-4-yl 2-[(Z)-N-(2,2,2-trifluoroethyl)carbamoylmethoxyimino]acetamido]ceph-3-em-4-carboxylic acid, used without further purification for subsequent stages.

19. Product obtained as a 6:4 mixture of diastereoisomers, n.m.r. in solvent A: 2.26 (m, 2H); 3.22 (m, 2H); 3.32 (d, 1H); 3.59 (d, 1H); 4.06 (d, 1H); 4.25 (s, 3H); 4.48 (d, 1H); 4.68 and 4.74 (2×t, 1H); 5.01 (d, 1H); 5.66 (d, 1H); 6.78 and 6.81 (2×s, 1H); 7.61 (br, 1H); 7.93 (d, 1H); 8.91 (d, 1H).

20. The 3-aminomethylcephalosporin may be prepared as follows: Using the general procedure outlined in Footnote 6 above, 2-((Z,RS)-2-oxopyrrolidin-3-yloxyimino)-2-(2-tritylaminothiazol-4-yl)acetic acid was condensed with 7-amino-3-azidomethylceph-3-em-4-carboxylic acid to give 3-azidomethyl-7-[2-((Z,RS)-2-oxopyrrolidin-3-yloxyimino)-2-(2-tritylaminothiazol-4-yl)acetamido]ceph-3-em-4-carboxylic acid, n.m.r. in solvent A: 2.53 (m, 2H); 3.3–3.6 (m, 4H); 4.09 (d, 1H); 4.45 (d, 1H); 5.05 (m, 2H); 5.88 (d, 1H); 6.75 (s, 1H); 7.33 (m, 15H).

The azide was reduced by the standard procedure to give 3-aminomethyl-7-[2-(2-aminothiazol-4-yl)-2((Z,RS)-2-oxopyrrolidin-3-yloxyimino)acetamido]ceph-3-em-4-carboxylic acid as a 6:4 mixture of diastereoisomers, n.m.r. in solvent A: 2.3 (m, 2H); 3.1–3.8 (m, 6H); 4.73 and 4.78 (2×t, 1H); 5.02 (d, 1H); 5.72 (d, 1H); 6.81 and 6.83 (2×s, 1H).

21. n.m.r. in solvent A: 1.23 (t, 3H); 3.32 (d, 1H); 3.6 (d, 1H); 3.71 (s, 3H); 4.05 (m, 4H); 5.01 (d, 1H); 5.68 (d, 1H); 6.71 (s, 1H); 7.28 (s, 2H).

22. n.m.r. in solvent A: 0.93 (t, 3H); 1.78 (quintet, 2H); 3.34 (d, 1H); 3.58 (d, 1H); 4.06 (br, 1H); 4.22 (s, 3H); 4.42 (t, 1H); 4.46 (br, 1H); 5.02 (d, 1H); 5.75 (d, 1H); 7.59 (br, 1H); 7.91 (br, 1H); 8.9 (d, 1H). Retention time 5.8 minutes on a reversed phase Partisil PXS 10/25 ODS-2 column, using MeOH/water/TFA 40:60:0.2 v/v/v as eluant.

23. The 3-aminomethylcephalosporin may be prepared as follows: Hydrazine hydrate (15 ml) was added dropwise to a stirred solution of t-butyl 2-(N-phthalimido-oxy)butyrate (45.8 g) in dichloromethane (600 ml) at ambient temperature. After 2 hours, a mixture of 25% aqueous ammonia (120 ml) and water (200 ml) was added, and t-butyl-2-aminoxybutyrate isolated by a conventional extractive procedure. By following the procedure of Footnote 6, this was converted to 2-[(Z)-1-(t-butoxycarbonyl)propoxyimino]-2-(2-formamidothiazol-4-yl)acetic acid, precipitated as its triethylamine salt, having the following n.m.r. in d$_6$-DMSO: 0.94 (t, 3H); 1.21 (s, 9H); 1.46 (s, 9H); 1.73 (quintet, 2H); 3.03 (q, 6H); 4.3 (t, 1H); 7.25 (s, 1H); 8.51 (s, 1H).

Following the procedure of Footnote 6, the above acetic acid was condensed with 7-amino-3-azidomethylceph-3-em-4-carboxylic acid, the formyl group was removed by hydrolysis, and the resulting product was reduced to the 3-aminomethylcephem. Careful chromatography on Diaion HP20SS, eluting successively with water, water/CH$_3$CN, 97.5:2.5 v/v, water/CH$_3$CN, 95:5 v/v and water/CH$_3$CN, 92.5:7.5 v/v, allowed substantial separation of the diasteroisomers of 3-aminomethyl-7-[2-(2-aminothiazol-4-yl)-2-((Z)-1-carboxypropoxyimino)acetamido]ceph-3-em-4-carboxylic acid. The more polar (m.p.) isomer, having retention time 3.02 minutes on a reversed phase Partisil PXS 10/25 ODS-2 column, using MeOH/H$_2$O/HOAc 30:70:1 v/v/v as eluant, had the following n.m.r. in solvent A: 0.95 (t, 3H); 1.8 (m, 2H); 3.28 (d, 1H); 3.43 (d, 1H); 3.58 (d, 1H); 3.69 (d, 1H); 4.45 (t, 1H); 5.02 (d, 1H); 5.75 (d, 1H); 6.79 (s, 1H).

The less polar (l.p.) isomer, having retention time 3.76 minutes under identical conditions to the above, had the following n.m.r. in solvent A: 1.0 (t, 3H); 1.83 (m, 2H); 3.28 (d, 1H); 3.43 (d, 1H); 3.58 (d, 1H); 3.69 (d, 1H); 4.43 (t, 1H); 5.03 (d, 1H); 5.71 (d, 1H); 6.77 (s, 1H).

24. n.m.r. in solvent A: 0.94 (t, 3H); 1.79 (quintet, 2H); 3.34 (d, 1H); 3.56 (d, 1H); 4.05 (br, 1H); 4.22 (s, 3H); 4.37 (t, 1H); 4.47 (br, 1H); 5.03 (d, 1H); 5.69 (d, 1H); 6.77 (s, 1H); 7.6 (br, 1H); 7.92 (br, 1H); 8.9 (d, 1H). Retention time 6.8 minutes on a reversed phase Partisil PXS 10/25 ODS-2 column, using MeOH/water/TFA 40:60:0.2 v/v/v as eluant.

25. n.m.r. in solvent A: 1.65 (m, 4H); 2.03 (m, 4H); 3.34 (d, 1H); 3.61 (d, 1H); 4.25 (d, 1H); 4.65 (d, 1H); 5.03 (d, 1H); 5.72 (d, 1H); 6.75 (s, 1H); 7.03 (d, 1H); 7.67 (d, 1H); 8.1 (d, 1H); 8.7 (d, 1H).

26. Starting material was 2,3-dihydro-7-methylthiothiazolo[2,3-a]pyrimidinium tetrafluoroborate.

27. n.m.r. in solvent A: 1.67 mm, 4H); 2.04 (m, 4H); 3.27 (d, 1H); 3.58 (d, 1H); 3.69 (t, 2H); 4.22 (d, 1H); 4.55 (d, 1H); 4.6 (t, 1H); 5.04 (d, 1H); 5.73 (d, 1H); 6.67 (d, 1H); 6.75 (s, 1H); 8.12 (d, 1H).

28. The starting material was prepared by dissolving 1-(2-cyanothiazol-4-yl)methyl-4-methylthiopyridinium chloride (242 mg) in a mixture of dichloromethane (11 ml) and TFA (2 ml), cooling in ice, and treating with 3-chloroperoxybenzoic acid (232 mg). After stirring for 40 minutes solvents were evaporated and the residue was treated with water (8 ml) and extracted with ether (3 portions of 5 ml). The aqueous layer containing 1-(2-cyanothiazol-4-yl)methyl-4-methylulphinylpyridinium salts was used as such.

29. n.m.r. in solvent A: 1.82 (m, 2H); 2.37 (t, 4H); 3.29 (d, 1H); 3.52 (d, 1H); 4.21 (d, 1H); 4.41 (d, 1H); 5.04 (d, 1H); 5.53 (s, 2H); 5.72 (d, 1H); 6.75 (s, 1H); 6.95 (dd, 1H); 7.34 (dd, 1H); 8.17 (dd, 1H); 8.29 (s, 1H); 8.34 (dd, 1H).

30. The starting material was prepared as in Footnote 28, but starting from 4-methylthio-1-(1,2,3-thiadiazol-4-yl)methylpyridinium methanesulphonate.

31. n.m.r. in solvent A: 1.82 (m, 2H); 2.38 (t, 4H); 3.28 (d, 1H); 3.51 (d, 1H); 4.2 (d, 1H); 4.41 (d, 1H); 5.05 (d, 1H); 5.71 (d, 1H); 5.82 (s, 2H); 6.73 (s, 1H); 6.94 (dd, 1H); 7.35 (dd, 1H); 8.25 (d, 1H); 8.43 (d, 1H); 9.26 (s, 1H).

32. n.m.r. in solvent A: 1.41 (d, 3H); 3.27 (d, 1H); 3.51 (d, 1H); 4.21 (d, 1H); 4.51 (d, 1H); 4.59 (q, 1H); 5.06 (d, 1H); 5.74 (d, 1H); 5.86 (s, 2H); 6.76 (s, 1H); 6.95 (dd, 1H); 7.35 (dd, 1H); 8.27 (d, 1H); 8.45 (d, 1H); 9.27 (s, 1H).

Retention time 5.0 minutes on a reversed phase Partisil PXS 10/25 ODS-2 column using MeOH/water/TFA 35:65:0.2 v/v/v as eluant.

33. n.m.r. in solvent A: 0.92 (t, 3H); 1.78 (quintet, 2H); 3.27 (d, 1H); 3.36 (d, 1H); 4.21 (d, 1H); 4.42 (d, 1H); 4.44 (t, 1H); 5.04 (d, 1H); 5.72 (d, 1H); 5.86 (s, 2H); 6.76 (s, 1H); 6.95 (dd, 1H); 7.32 (dd, 1H); 8.27 (d, 1H); 8.45 (d, 1H); 9.26 (s, 1H). Retention time 7.6 minutes on a reversed phase Partisil PXS 10/25 ODS-2 column, using MeOH/water/TFA 35:65:0.2 v/v/v as eluant.

34. The starting material was prepared as in Footnote 28, but starting with 1-(E-3-cyano-2-methyl allyl)-4-methylthiopyridinium bromide, and using two equivalents of 3-chloroperoxybenxoic acid, to give substantially 1-(E-3-cyano-2-methylallyl)-4-methanesulphonylpyridinium bromide.

35. n.m.r. in solvent A: 0.95 (t, 3H); 1.8 (quintet, 2H); 1.96 (d, 3H); 3.29 (d, 1H); 3.54 (d, 1H); 4.24 (d, 1H); 4.43 (d, 1H); 4.45 (t, 1H); 4.93 (s, 2H); 5.06 (d, 1H); 5.23 (d, 1H); 5.74 (d, 1H); 6.78 (s, 1H); 6.96 (dd, 1H); 7.31 (dd, 1H); 8.01 (dd, 1H); 8.19 (dd, 1H).

Retention time 4.3 minutes on a reversed phase Partisil PXS 10/25 ODS-2 column, using MeOH/Water/TFA 40:60:0.2 v/v/v as eluant 36. n.m.r. in solvent A: 1.67 (br, 4H); 2.0 (br, 4H); 3.31 (d, 1H); 3.61 (d, 1H); 4.24 (s+m, 4H); 4.46 (d, 1H); 5.01 (d, 1H); 5.71 (d. 1H); 6.72 (s, 1H); 7.6 (m, 1H); 7.82 (m, 1H); 8.84 (d, 1H).

EXAMPLE 219

The general procedure of Examples 7–14 was repeated using DMF as solvent at ambient temperature, with the appropriate starting materials. Products were worked up by chromatography on Diaion CHP20P resin, eluting with CH$_3$CN/water mixtures. The following compounds were made.

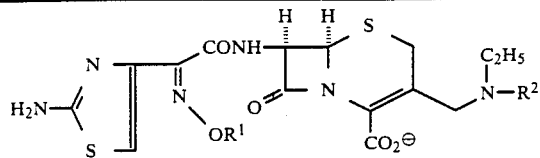

| Example No. | R¹ | R² | Yield % | Footnotes |
|---|---|---|---|---|
| 219 | CH₃<br>│<br>—CHCO₂H<br>(m.p. isomer) | (heterocycle structure shown) | 48 | 1,2,3 |

Footnotes
1. Starting material was 1-methyl-4-methylthiothieno[2,3-d]pyrimidinium tetrafluoroborate.
2. n.m.r. in solvent A: 1.29 (t, 3H); 1.38 (d, 3H); 3.21 (d, 1H); 3.44 (d, 1H); 4.01 (s+m, 5H); 4.56 (q, 1H); 4.86 (d, 1H); 5.05 (d, 1H); 5.22 (d, 1H); 5.74 (d, 1H); 6.75 (s, 1H); 7.8 (d, 1H); 7.9 (d, 1H); 8.81 (s, 1H).
Retention time 5.1 minutes on a reversed phase Partisil PXS 10/25 ODS-2 column, using MeOH/H₂O/TFA 40:60:0.2 as eluant.
3. The cephalosporin intermediate may be prepared as follows: To a stirred solution of triethylamine (0.18 ml) in MeOH (50 ml) was added 3-aminomethyl-7-[2-(2-aminothiazol-4-yl)-2-((Z)-1-carboxyethoxyimino)acetamido]ceph-3-em-4-carboxylic acid (more polar isomer, 0.6 g), followed by sodium cyanoborohydride (0.08 g). A solution of acetaldehyde (0.07 ml) in MeOH (5 ml) was added over 40 minutes, then the solvent was removed and the residue was dissolved in water (100 ml). After reducing the pH to 3.5, the solution was loaded onto a column of Diaion CHP20P resin. Elution with 95:5 H₂O:CH₃CN gave 7-[2-(2-aminothiazol-4-yl)-2-((Z)-1-carboxyethoxyimino)acetamido]-3-ethylaminomethylceph-3-em-4-carboxylic acid (more polar isomer), having the following n.m.r. in solvent A: 1.19 (t, 3H); 1.43 (d, 3H); 2.94 (q, 2H); 3.37 (d, 1H); 3.41 (d, 1H); 3.6 (d, 1H); 3.76 (d, 1H); 4.61 (q, 1H); 5.03 (d, 1H); 5.75 (d, 1H); 6.78 (s, 1H).
Retention time 3.25 minutes on a reversed phase Partisil PXS 10/25 ODS-2 column, using MeOH/water/HOAc 25:75:1 as eluant.

EXAMPLE 220

Dry dichloromethane (5 ml) was cooled to −10° and oxalyl chloride (1.15 mM), followed by DMF (1.15 mM), was added, and the mixture was stirred at −15° to −10° for 1 hour. To this was then added 1-(Z)-chloroethylene-2-(2-formamidothiazol-4-yl)acetic acid (1 mM), followed by N-methylmorpholine (1.15 mM), and the mixture was stirred for 1 hour at −15° to −10°.

In another flask a solution of 7-amino-3-(1-methyl-4-pyridinio)aminomethylceph-3-em-4-carboxylic acid (1.15 mM), as its partial salt with 1.76 moles TFA, in dimethylacetamide (6 ml) was treated with N-methylmorpholine (2.08 mM), and the pink suspension was syringed into the flask containing the activated acid, followed by N-methylmorpholine (1.15 mM). After stirring for 1 hour, at −10° and 1 hour at ambient temperature, the mixture was filtered. The solution was evaporated to dryness, and deformylated by solution in methanol (20 ml) and treating with concentrated hydrochloric acid (0.5 ml), at ambient temperature for 2 hours. After removal of the methanol, the residue was dissolved in water, the pH was adjusted to 5.2 with aqueous NaHCO₃, and the product was purified by chromatography on Diaion CHP20P resin to give 7-[2-(2-aminothiazol-4-yl)-2-(Z)-chloromethyleneacetamido]-3-(1-methyl-4-pyridinio)aminomethylceph-3-em-4-carboxylic acid, in 5% yield, having the following n.m.r. in solvent A: 3.27 (d, 1H); 3.5 (d, 1H); 3.84 (s, 3H); 4.19 (d, 1H); 4.41 (d, 1H); 5.07 (d, 1H); 5.66 (d, 1H); 6.38 (s, 1H); 6.82 (s, 1H); 6.89 (d, 1H); 7.26 (d, 1H); 8.01 (d, 1H); 8.18 (d, 1H).

EXAMPLES 221–228

To a stirred suspension of 3-aminomethyl-7-[2-(2-aminothiazol-4-yl)-2-((Z)-1-carboxy-1-methylethoxyimino)acetamido]ceph-3-em-4-carboxylic acid (240 mg, 0.5 mmole) and triethylamine (200 ul, 1.4 mmole) in EtOH (10 ml) at 25° was added 1-methyl-4-methylthioquinazolinium iodide (160 mg, 0.5 mmole). After 1.5 hours the solution was evaporated to dryness under reduced pressure, the residue dissolved in water (10 ml), the solution acidified with excess 5% v/v aqueous HOAc and the insoluble material filtered off. The filtrate was applied to a Diaion HP20 column and the product purified by gradient elution with MeOH. Using this general process and the appropriate quaternary heterocycle, the following compounds were obtained:

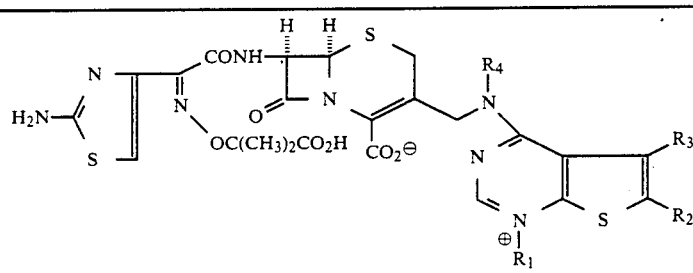

| Example No. | R₁ | R₂ | R₃ | R₄ | Yield % | Footnotes |
|---|---|---|---|---|---|---|
| 221 | CH₃ | CH₃ | CH₃ | H | 11 | 1,2,3 |
| 222 | CH₃ | H | H | H | 9 | 4,5,6 |
| 223 | —CH₂CH=CH₂ | H | H | H | 44 | 7,8,6 |
| 224 | —CH₂—⟨phenyl⟩—NO₂ | H | H | H | 33 | 9,10,6 |
| 225 | CH₃ | H | H | CH₂CH₃ | 29 | 11,12,13,5,6 |
| 226 | —CH₂CH=CH₂ | H | H | CH₂CH₃ | 22 | 14,15,13,8,6 |

-continued

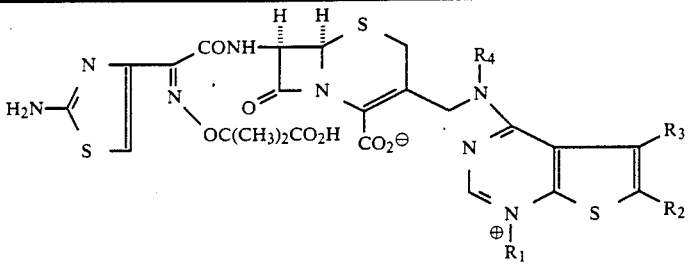

| Example No. | $R_1$ | $R_2$ | $R_3$ | $R_4$ | Yield % | Footnotes |
|---|---|---|---|---|---|---|
| 227 | $-CH_2CH=CH_2$ | H | H | $-CH_2-\underset{\substack{N\\H}}{\overset{N}{\diagdown}}-F$ | 46 | 16,17,18, 19,8,6 |
| 228 | $CH_3$ | H | H | $-CH_2-\underset{N}{\diagdown}$ | 35 | 20,21,22, 5,6 |

Footnotes 1. n.m.r. in solvent A: 1.41 (s, 3H); 1.43 (s, 3H); 2.52 (m, 6H); 3.49 (d, 1H); 3.72 (d, 1H); 3.94 (s, 3H); 4.26 (d, 1H); 4.82 (d, 1H); 5.02 (d, 1H); 5.76 (d, 1H); 6.75 (s, 1H); 8.74 (s, 1H).
2. The 1,5,6-trimethyl-4-methylthiothieno[2,3-d]pyrimidinium iodide may be prepared as follows: A solution of 5,6-dimethyl-4-methylthiothieno[2,3-d]pyrimidine in $CH_2Cl_2$ was treated with trimethyloxonium tetrafluoroborate and stirred, under argon, at room temperature overnight. The solution was evaporated to dryness to give a white solid. N.m.r. in $d_6DMSO$: 2.6 (s, 6H); 2.8 (s, 3H); 4.2 (s, 3H); 9.4 (s, 1H).
3. 5,6-Dimethyl-4-methylthiothieno[2,3-d]pyrimidine may be prepared as follows: A solution of 5,6-dimethyl-1H-thieno[2,3-d]pyrimidin-4-one in $CH_3CN$ was treated, at reflux for 3 hr, with Lawesson's reagent. The reaction mixture was poured into water and extracted with ethyl acetate. The organic extracts were combined and extracted several times with 2N NaOH. The aqueous extracts were acidified with HCl and re-extracted with ethyl acetate, the extracts washed with water, dried and evaporated to dryness. The crude 5,6-dimethyl-1H-thieno[2,3-d]pyrimidin-4-thione so obtained ($M^+ = 196$) was alkylated with methyl iodide in aqueous sodium hydroxide to give, after chromatography on silica, 5,6-dimethyl-4-methylthiothieno[2,3-d]pyrimidine. n.m.r. in $CDCl_3$: 2.5 (s, 6H); 2.6 (s, 3H); 8.7 (s, 1H). This product was quaternised by heating with excess methyl iodide under reflux for 18 hours.
4. n.m.r. in solvent A: 1.4 (s, 3H); 1.44 (s, 3H); 3.46 (d, 1H); 3.62 (d, 1H); 4.02 (s, 3H); 4.55 (d, 1H); 4.9 (d, 1H); 5.02 (d, 1H); 5.82 (d, 1H); 6.72 (s, 1H); 7.90 (s, 1H); 8.85 (s, 1H).
5. The 1-methyl-4-methylthiothieno[2,3-d]pyrimidinium tetrafluoroborate was prepared from 4methylthiothieno[2,3-d]pyrimidine and trimethyloxonium tetrafluoroborate by a procedure analogous to that described in footnote 2. n.m.r. in $d_6DMSO$: 2.9 (s, 3H); 4.34 (s, 3H); 7.88 (d, 1H); 8.28 (d, 1H); 9.52 (s, 1H).
6. The 4-methylthiothieno[2,3-d]pyrimidine was prepared from 1H-thieno[2,3-d]pyrimidine-4-one by a two-stage procedure analogous to that described in footnote 3. n.m.r. in $CDCL_3$: 2 72 (s, 3H); 7.35 (d, 1H); 7.45 (d, 1H); 8.85 (s, 1H).
7. n.m.r. in solvent A: 1 36 (s, 3H); 1.38 (s, 3H); 3.36 (d, 1H); 3.6 (d, 1H); 4.56 (d, 1H); 4.88 (d, 1H); 5.04 (d, 3H); 5.42 (d, 1H); 5.48 (d, 1H); 5.75 (d, 1H); 6.04 (m, 1H); 6.75 (s, 1H); 7.86 (d, 1H); 7.93 (d, 1H); 8.92 (s, 1H).
8. The 1-allyl-4-methylthiothieno[2,3-d]pyrimidinium bromide was prepared from 4-methylthiothieno[2,3-d]pyrimidine and allyl bromide in refluxing acetonitrile. The excess allyl bromide and solvent were removed by evaporation. n.m.r. in $d_6DMSO$: 2.9 (s, 3H); 5.45 (d, 2H); 5.6 (d, 1H); 5.75 (d, 1H); 6.18 (m, 1H); 7.88 (d, 1H); 8.32 (d, 1H); 9.72 (s, 1H).
9. n.m.r. in solvent A: 1.42 (s, 3H); 1.44 (s, 3H); 3.40 (d, 1H); 3.62 (d, 1H); 4.6 (d, 1H); 4.92 (d, 1H); 5.08 (d, 1H); 5.76 (d, 1H); 5.84 (s, 2H); 6.74 (s, 1H); 7.75 (d, 1H); 7.8 (d, 1H); 7.92 (d, 1H); 8.24 (d, 1H); 9.18 (s, 1H).
10. The 4-methylthio-1-p-nitrobenzylthieno[2,3-d]pyrimidinium bromide was prepared as follows: 4-Methylthiothieno[2,3-d]pyrimidine in $CH_3CN$ was treated with p-nitrobenzyl bromide and the solution refluxed for 8 hr. The solution was evaporated to dryness and the residue triturated with $CH_2Cl_2$. The insoluble solid was filtered off, and dried. n.m.r. in $d_6DMSO$: 2.94 (s, 3H); 6.16 (s, 2H); 7.82 (dd, 2H); 8.2 (d, 1H); 8.25 (d, 1H); 9.8 (s, 1H).
11. To a stirred suspension of 3-ethylaminomethyl-7-[2-(2-aminothiazol-4-yl)-2-((Z)-1-carboxy-1-methylethoxyimino)acetamido]ceph-3-em-4-carboxylic acid (260 mg, 0.5 mM) in DMF (5 ml) was added $Et_3N$ (150 μl, 1.1 mM) followed by 1-methyl-4-methylthiothieno[2,3-d]pyrimidinium tetrafluoroborate (150 mg, 0.53 mM). The mixture was stirred at room temperature overnight before being poured into $H_2O$ (100 ml). The pH of the solution was adjusted to 3.5 with glacial acetic acid and the solution applied to a Diaion HP20SS column. The product was eluted using $H_2O$ and $CH_3CN$ and the appropriate fractions were freeze-dried.
12. n.m.r. in solvent A: 1.35 (br t, 3H); 1.43 (s, 3H); 1.44 (s, 3H); 3.38 (d, 1H); 3.54 (d, 1H); 4.06 (m, 2H); 4.06 (s, 3H); 4.79 (d, 1H); 5.16 (d, 1H); 5.28 (d, 1H); 5.85 (d, 1H); 6.71 (s, 1H); 7.82 (d, 1H); 7.95 (d, 1H); 8.85 (s, 1H).
13. The 3-ethylaminomethyl-7-[2-(2-aminothiazol-4-yl)-2-((Z)-1-carboxy-1-methylethoxyimino)acetamido]ceph-3-em-4-carboxylic acid was prepared as follows:
3-Aminomethyl-7-[2-(2-aminothiazol-4-yl)-2-((Z)-1-carboxy-1-methylethoxyimino)acetamido]ceph-3-em-4-carboxylic acid (2 g, 4 mM) was suspended in MeOH (200 ml), and $Et_3N$ (570 μl, 4.1 mM) followed by sodium cyanoborohydride were added. The mixture was stirred, under argon, at room temperature and treated, dropwise, during 40 min. with a solution of acetaldehyde (276 μl., 4.9 mM) in methanol (2 ml). After 3 hr. the methanol was evaporated under reduced pressure and the product was purified by chromatography on Diaion HP20SS using $H_2O$ and $CH_3CN$ in a graded elution. The appropriate fractions were combined and freeze dried. N.m.r. in solvent A: 1.15 (t, 3H); 1.44 (s, 3H); 1.46 (s, 3H); 2.82 (q, 2H); 3.36 (d, 1H); 3.45 (d, 1H); 3.59 (d, 1H); 3.76 (d, 1H); 5.0 (d, 1H); 5.77 (d, 1H); 6.74 (s, 1H).
14. The procedure described in Footnote 11 was followed, but starting with 1-allyl-4-methylthiothien[2,3-d]pyrimidinium bromide.
15. n.m.r. in solvent A: 1.32 (t, 3H); 1.45 (br s, 6H); 3.24 (d, 1H); 3.46 (d, 1H); 4.10 (m, 2H); 4.91 (d, 1H); 5.08 (d, 1H); 5.26 (d, 1H); 5.45 (d, 1H); 5.52 (d, 1H); 5.72 (d, 1H); 6.05 (m, 1H); 6.7 (s, 1H); 7.79 (d, 1H); 7.92 (d, 1H); 8.89 (s, 1H).
16. The procedure described in Footnote 11 was followed, but starting with 3-(2-fluoro-1H-imidazol-4-ylmethyl)aminomethyl-7-[2-(2-aminothiazol-4-yl)-2-((Z)-carboxy-1-methylethoxyimino)acetamido]ceph-3-em-4-carboxylic acid and 1-allyl-4-methylthio-thieno[2,3-d]pyrimidinium bromide.
17. n.m.r. in solvent A: 1.42 (s, 3H); 1.46 (s, 3H); 3.12 (d, 1H); 3.37 (d, 1H); 4.93 (d, 1H); 4.97 (d, 1H); 5.0-5.1 (m, 4H); 5.18 (d, 1H); 5.44 (d, 1H); 5.5 (d, 1H); 5.72 (d, 1H); 6.02 (m, 1H); 6.72 (s, 1H); 6.82 (s, 1H); 7.79 (d, 1H); 8.04 (d, 1H); 8.87 (s, 1H).
18. 3-(2-Fluoro-1H-imidazol-4-ylmethyl)aminomethyl-7-[2-(2-aminothiazol-4-yl)-2-((Z)-1-carboxy-1-methylethoxyimino)-acetamido]ceph-3-em-4-carboxylic acid was prepared from 3-(2-fluoro-1-triphenylmethylimidazol-4-ylmethyl)aminomethyl-7-[2-(2-aminothiazol-4-yl)-2-((Z)-1-carboxy-1-methylethoxyimino)acetamido]ceph-3-em-4-carboxylic acid by treatment in $CH_2Cl_2$ at room temperature with p-toluene sulphonic acid $H_2O$. The reaction mixture was poured into water and the aqueous layer applied to a Diaion HP20SS column. The product was obtained by gradient elution with $CH_3CN/H_2O$ and freeze-drying the appropriate fractions. N.m.r. in solvent A: 1.45 (br s, 6H); 3.42 (d, 1H); 3.54 (d, 1H); 3.68 (d, 1H); 3.83 (d, 1H); 3.92 (s, 2H); 5.03 (d, 1H); 5.75 (d, 1H); 6.76 (s, 1H); 6.93 (s, 1H).
19. The 3-(2-fluoro-1-triphenylmethylimidazol-4-ylmethyl)aminomethyl-7-[2-(2-aminothiazol-4-yl)-2-((Z)-1-carboxy-1-methylethoxyimino)acetamido]ceph-3-em-4-carboxylic acid was prepared from 3-aminomethyl-7-[2-(2-aminothiazol-4-yl)-2-((Z)-1-carboxy-1-methylethoxy imino)acetamido]ceph-3-em-4-carboxylic acid and 2-fluoro-4-formyl-1-triphenylmethylimidazole by a procedure analogous to that described in footnote 13. N.m.r. in solvent A: 1.44 (s, 3H); 1.46 (s, 3H);

3.32 (d, 1H); 3.4 (d, 1H); 3.58 (d, 1H); 3.75 (d, 1H); 3.92 (s, 2H); 5.0 (d, 1H); 5.71 (d, 1H); 6.75 (s, 1H); 6.8 (s, 1H); 7.13 (d, 6H); 7.43 (m, 9H).
20. The procedure described in Footnote 11 was followed but starting with 3-(pyrid-3-ylmethyl)aminomethyl-7-[2-(2-aminothiazol-4-yl)-2-((Z)-1-carboxy-1methylethoxyimino)acetamido]ceph-3-em-4-carboxylic acid.
21. N.m.r. in solvent A: 1.42 (s, 6H); 3.35 (br d, 1H); 3.54 (br d, 1H); 4.04 (s, 3H); 5.02 (d, 1H); 5.05–5.55 (m, 4H); 5.74 (d, 1H); 6.72 (s, 1H); 7.35 (m, 1H); 7.79 (br d, 1H); 7.92 (m, 2H); 8.48 (br s, 1H); 8.93 (s, 1H).
22. 3-(Pyrid-3-ylmethyl)aminomethyl-7-[2-(2-aminothiazol-4-yl)-2-((Z)-1-carboxy-1-methylethoxyimino)acetamido]ceph-3-em-4-carboxylic acid was prepared following the procedure described in Footnote 3, but with 3-formylpyridine as the aldehyde. N.m.r. in solvent A: 1.4 (s, 3H); 1.44 (s, 3H); 3.39 (d, 1H); 3.48 (d, 1H); 3.65 (d, 1H); 3.73 (d, 1H); 4.12 (s, 2H); 5.02 (d, 1H); 5.76 (d, 1H); 6.76 (s, 1H); 7.38 (m, 1H); 7.87 (d, 1H); 8.54 (br s, 1H); 8.62 (s, 1H).

EXAMPLES 229–233

To a stirred suspension of the appropriate 3-aminomethylceph-3-em-4-carboxylic acid (0.82 mmole) and triethylamine (1.8 mmole) in DMF (10 ml) at 25° was added the appropriate 6-chloro-1,2,4-triazolo[4,3-b]pyridazinium iodide (0.84 mmole). After stirring overnight, the mixture was poured into water (100 ml), the pH adjusted to 3.5 with glacial acetic acid and the solution filtered. The filtrate was applied to a Diaion HP20P resin column, and the product was obtained by gradient elution using water and acetonitrile. The appropriate fractions were freeze-dried.

was filtered off, washed with a little ether and dried under vacuum, m.pt. 238°–40°.
3. n.m.r. in solvent A: 1.42 (s, 3H); 1.45 (s, 3H); 3.38 (d, 1H); 3.64 (d, 1H); 4.1 (br s, 4H); 4.38 (m, 1H); 5.02 (d, 1H); 5.73 (d, 1H); 6.74 (s, 1H); 7.53 (bs, 1H); 8.35 (d, 1H); 9.65 (s, 1H).
4. The 6-chloro-1,2,4-triazolo[4,3-b]pyridazinium iodide may be prepared as follows: 6-chloro-1,2,4-triazolo[4,3-b]pyridazine and methyl iodide were refluxed in acetonitrile for 4 hr. The reaction mixture was cooled and the solid which had precipitated during the reaction was filtered off, washed with a little acetonitrile, and dried, m pt 208°–210°.
5. n.m.r. in solvent A: 1.42 (s, 3H); 1.44 (s, 3H); 3.45 (d, 1H); 3.66 (d, 1H); 4.1 (m, 4H); 4.5 (d, 1H); 5.04 (d, 1H); 5.78 (d, 1H); 6.74 (s, 1H); 7.57 (m, 1H); 8.34 (d, 1H).
6. The 3,6-dichloro-1-methyl-1,2,4-triazolo [4,3-b]pyridazinium iodide was prepared from 3,6-dichloro-1,2,4-triazolo[4,3-b]pyridazine and methyl iodide in acetonitrile. N.m.r. in $d_6$ DMSO: 4.38 (s, 3H); 8.45 (d, 1H); 9.12 (d, 1H).
7. Prepared from 3-ethylaminomethyl-7-[2-(2-aminothiazol-4-yl)-2-((Z)-1-carboxy-1methylethoxyimino)acetamido]ceph-3-em-4-carboxylic acid.
8. n.m.r. in solvent A: 1.14 (t, 3H); 1.42 (s, 6H); 3.2 (d, 1H); 3.46 (d, 1H); 3.6 (m, 1H); 3.75 (m, 1H); 4.18 (s, 3H); 4.64 (m, 2H); 5.06 (d, 1H); 5.7 (d, 1H); 6.72 (s, 1H); 8.2 (br s, 1H); 8.52 (d, 1H); 9.69 (s, 1H).
9. Sodium hydrogen carbonate was used in place of triethylamine. Yield 3%.
10. n.m.r. in solvent A: 1.42 (s, 3H); 1.45 (s, 3H); 3.42 (d, 1H); 3.65 (d, 1H); 4.07 (s, 3H); 4.24 (d, 1H); 4.46 (d, 1H); 5.01 (d, 1H); 5.72 (d, 1H); 6.74 (s, 1H); 7.82 (d, 1H); 7.87 (d, 1H); 8.64 (dd, 1H); 8.91 (dd, 1H).
11. The 3-chloro-1-methyl-1,2,4-triazolo[4,3-b]pyradizinium iodide was prepared from 3-chloro-1,2,4-triazolo[4,3-b]pyridazine and methyl iodide in acetonitrile. The product which separated from solution was filtered off washed with a little $CH_3CN$ and ether and dried, m.pt. 225°–227°.

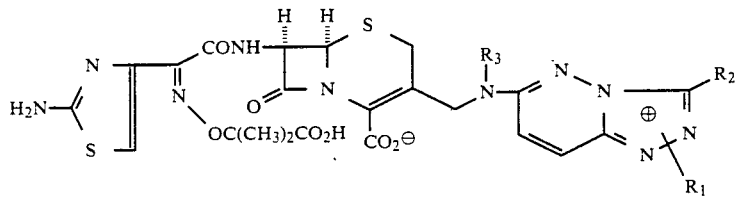

| Example No. | $R_1$ | $R_2$ | $R_3$ | Yield % | Footnotes |
|---|---|---|---|---|---|
| 229 | 2-$CH_3$ | H | H | 8 | 1,2 |
| 230 | 1-$CH_3$ | H | H | 21 | 3,4 |
| 231 | 1-$CH_3$ | Cl | H | 16 | 5,6 |
| 232 | 1-$CH_3$ | H | $CH_2CH_3$ | 12 | 7,8,4 |
| 233 | | | | | 9,10,11 |

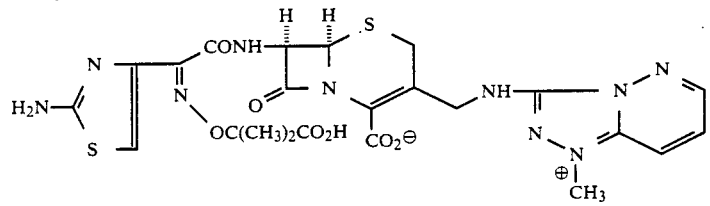

Footnotes
1. n.m.r. in solvent A: 1.46 (br s, 6H); 3.42 (d, 1H); 3.65 (d, 1H); 4.0–4.2 (br s, 4H); 4.3–4.5 (br s, 1H); 5.04 (d, 1H); 5.75 (d, 1H); 6.74 (s, 1H); 7.3 (d, 1H); 8.04 (d, 1H); approximately 11.0 (s, 1H).
2. The triazolopyridazinium salt may be prepared as follows: 6-chloro-1,2,4-triazolo[4,3-b]pyridazine in methanol was treated with methyl iodide, and the solution was refluxed for 2 hr. Anhydrous ether was then added to the reaction mixture and the precipitated solid so obtained

EXAMPLE 234

The process described in Example 221 was repeated using the appropriate 3-ethylaminomethyl cephem and quaternary heterocycle to give the following compound:

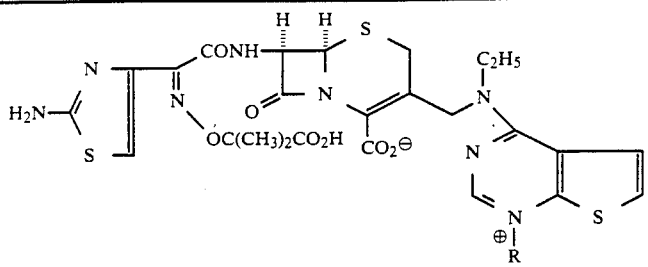

| Example No. | R | Yield % | Footnotes |
|---|---|---|---|
| 234 | —CH₂C(CH₃)=CH(CN) [—CH2C=CN with CH3 and H] | 44 | 1,2,3 |

Footnotes
1. n.m.r. in solvent A: 1.34 (m, 3H); 1.42 (br s, 6H); 2.08 (s, 3H); 3.38 (d, 1H); 3.53 (d, 1H); 4.02 (m, 2H); 4.80 (d, 1H); 5.14 (d, 1H); 5.2–5.45 (overlapping s, d, 3H); 5.68 (s, 1H); 5.84 (d, 1H); 6.7 (s, 1H); 7.79 (d, 1H); 7.9 (d, 1H); 8.84 (s, 1H).
2. The chemical shifts quoted probably refer to the major E isomer, but there is also evidence of the minor Z in the n.m.r. spectrum.
3. The starting material was prepared from 4-methylthiothieno[2,3-d]pyrimidine and 2-bromomethyl-1-cyanoprop-1-ene (mixture of E and Z isomers in the ratio 9:1) in CH₃CN. The precipitate was filtered off and washed with CH₃CN and dried. N.m.r. in d₆ DMSO: 2.1 (s, 3H); 2.92 (s, 3H); 5.64 (s, 2H); 5.86 (s, 1H); 7.86 (d, 1H); 8.24 (d, 1H); 9.6 (s, 1H).

EXAMPLE 235

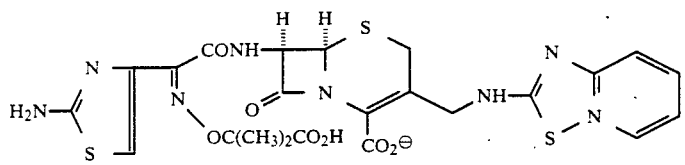

3-Aminomethyl-7-[2-(2-aminothiazol-4-yl)-2-((Z)-1-carboxy-1-methylethoxyimino)acetamido]ceph-3-em-4-carboxylic acid (242 mg, 0.5 mmole) was suspended in DMF (3 ml) and water (1 ml) and treated with 2-methylthio-1,2,4-thiadiazolo[2,3-a]pyridinium bromide (132 mg, 0.5 mmole) and then with sodium hydrogen carbonate (240 mg, 2.5 mmole) suspended in water (0.5 ml). The solution was stirred at room temperature overnight before being diluted with water (25 ml) and applied to a Diaion HP20SS column. Following gradient elution with acetonitrile/water the product was obtained by freeze-drying the appropriate fractions. Yield 11%. N.m.r. in solvent A: 1.45 (s, 3H); 1.46 (s, 3H), 3.64 (d, 1H); 3.76 (d, 1H); 4.34 (d, 1H); 4.88 (d, 1H); 5.07 (d, 1H); 5.78 (d, 1H); 6.73 (s, 1H); 7.0 (m, 1H); 7.13 (d, 1H); 7.72 (m, 1H); 8.17 (dd, b 1H).

EXAMPLES 236–243

A solution of 3-aminomethyl-7-[2-(2-aminothiazol-4-yl)-2-((Z)-1-carboxy-1-methylethoxyimino)acetamido]-ceph-3-em-4-carboxylic acid (0.5 mM) and NaHCO₃ (2.5 mM) in water (5 ml) was treated with an appropriate chloro- or methylsulphinyl-substituted quaternary heterocycle, at room temperature for 18 hrs. The solution was acidified with HOAc and sufficient sodium acetate added to redissolve any precipitate. The product was isolated by chromatography on an HP20 gravity column, eluting with CH₃CN/H₂O mixtures and then freeze-drying the appropriate fractions. The following compounds were obtained:

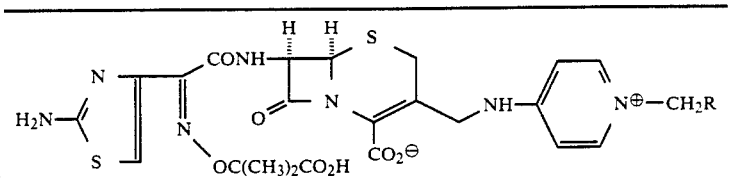

| Example No. | R | Yield % | Footnotes |
|---|---|---|---|
| 236 | 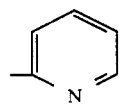 | 34 | 1,2 |
| 237 | 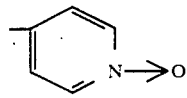 | 36 | 3,4 |

-continued

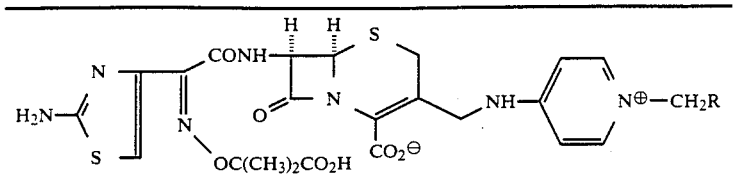

| Example No. | R | Yield % | Footnotes |
|---|---|---|---|
| 238 | (2-pyridyl-N-oxide) | 27 | 5,6 |
| 239 | (2,6-dichloropyridyl) | 26 | 7,8 |
| 240 | (methyl-NH-C(=O)-N(H)-C(=O)- pyrimidinone) | 33 | 9,10 |
| 241 | (3,5-dimethylisoxazolyl) | 57 | 11,12 |
| 242 | (2-hydroxy-6-cyclopropylpyridyl) | 48 | 13,14 |
| 243 | (1-methyl-isatin-yl) | 16 | 15,16 |

Footnotes
1. n.m.r. in solvent A: 1.45 (2xs, 6H); 3.4 (q, 2H); 4.3 (q. 2H); 5.05 (d, 1H); 5.45 (s, 2H); 5.7 (d, 1H); 6.7 (s, 1H); 6.9-8.5 (6xm, 8H).
2. The starting pyridinium salt was obtained by adding 4-hydroxypyridine (10 mM) to a stirred suspension of hexane-washed sodium hydride (10 mM) in DMF (15 ml). To this solution was added a solution of 4-chloromethylpyridine (10 M) in ether (5 ml), (obtained by treating the corresponding 4-chloromethylpyridine hydrochloride with NaHCO$_3$ in aqueous solution, extracting with ether and drying), and the mixture was stirred at room temperature for 18 hrs. The solvents were evaporated, and the residue was purified by MPLC, on Merck silica gel 9385, eluting with MeOH/CH$_2$Cl$_2$, 8-10:92-90, to give 1-(2-pyridylmethyl)-pyrid-4-one. Yield 65%. N.m.r. in CDCl$_3$: 5.0 (s, 2H); 7.2-7.8 (m, 4H); 6.35 (d, 2H); 8.6 (d, 2H).
This pyridone (1.5 mM) and tosyl chloride (1.65 mM) were heated in DMF at 80° for 45 minutes, the solvent was evaporated, and the residue triturated with CH$_2$Cl$_2$ to give 4-chloro-1-(2-pyridylmethyl)pyridinium tosylate in 70% yield. N.m.r. in d$_6$DMSO: 2.3 (s, 3H); 6.0 (s, 2H); 7.1 (d, 2H); 7.5 (d, 2H); 7.4-8.6 (m, 6H); 9.15 (d, 2H).
3. N.m.r. in solvent A: 1.45 (2×s, 6H); 3.4 (q, 2H), 4.3 (q, 2H); 5.1 (d, 1H); 5.35 (s, 2H); 5.8 (d, 1H); 6.75 (s, 1H); 6.95 (q, 1H); 7.1 (q, 1H); 7.4 (d, 2H); 8.2 (d, 1H); 8.3 (d, 2H); 8.4 (d, 1H).
4. The starting pyridinium salt was obtained as follows:
A solution of 4-chloromethyl-1-oxidopyridinium chloride (5 mM) in ether was basified with NaHCO$_3$ solution. The ether solution was separated and dried, 4-methylthiopyridine was added, the solvent was evaporated and the residue was kept at room temperature for 18 hrs. Trituration gave 4-methylthio-1-(1-oxidopyrid-4-ylmethyl)pyridinium chloride. N.m.r. in d$_6$ DMSO: 2.7 (s, 3H); 5.75 (s, 2H); 7.6 (d, 2H); 8.0 (d, 2H); 8.25 (d, 2H); 9.05 (d, 2H).
This thiomethyl compound (2 mM) was suspended in CH$_2$Cl$_2$ (10 ml) at 0°, and sufficient TFA was added to give a solution. A solution of MCPBA (2 mM) in CH$_2$Cl$_2$ (3 ml) was added, and the solution was allowed to warm to room temperature, then stirred for 1 hr. The solvents were evaporated, and the residue was triturated several times with ether, to remove excess MCPBA, to give 4-methylsulphinyl-1-(1-oxido-pyrid-4-ylmethyl)-pyridinium chloride, which was used without further purification or characterisation.
5. N.m.r. in solvent A: 1.4 (2×s, 6H); 3.35 (q, 2H), 4.3 (q, 2H); 5.05 (d, 1H); 5.45 (s, 2H); 5.7 (d, 1H); 6.7 (s, 1H); 6.5-8.4 (6×m, 8H).
6. The starting pyridinium salt was prepared by the process of Footnote 4, except that the reactants were warmed together to form a homogeneous melt, then heated at 100° for 15 minutes, cooled and triturated with CH$_2$Cl$_2$. N.m.r. in d$_6$ DMSO: 2.7 (s, 3H); 5.9 (s, 2H); 7.5, 7.95 and 8.35 (m, 6H); 8.95 (d, 2H). The methylthio compound was then oxidised to the required methylsulphinyl compound as described in Footnote 4.
7. Reaction solvent was H$_2$O/CH$_2$CN, (4:1). N.m.r. in solvent A: 1.45 (2×s, 6H); 3.4 (q, 2H), 4.3 (q, 2H); 5.05 (d, 1H); 5.4 (s, 2H); 5.7 (d, 1H); 6.7 (s, 1H); 6.95 (q, 1H); 7.4 (q, 1H); 7.55 (s, 2H); 8.15 (q, 1H); 8.35 (q, 1H).
8. The starting pyridinium salt was prepared by the process of Footnote 4, from 4-bromomethyl-2,6-dichloropyridine, except that this starting material reacted exothermically with 4-methylthiopyridine, so the reaction mixture was kept below 40° until the reaction was largely complete, then heated at 100° for 5 minutes. The product was crystallised from HCl/EtOH. N.m.r. in d$_6$ DMSO: 2.75 (t, 3H); 5.95 (s, 2H); 7.75 (s, 2H); 7.95 (d, 2H); 9.05 (d, 2H). The methylthio compound was oxidised to the required methylsulphinyl compound as in Footnote 4. N.m.r. in d$_6$-DMSO/CDCl$_3$: 2.95 (s, 3H); 5.95 (s, 2H); 7.7 (s, 2H); 8.4 (d, 2H); 9.3 (d, 2H).
9. N.m.r. in solvent A: 1.4 (2×s, 6H); 2.25 (s, 3H); 3.4 (q, 2H); 4.3 (q, 2H); 5.05 (d, 1H); 5.3 (s, 2H); 5.7 (d, 1H); 6.7 (s, H); 6.9 (d, 1H); 7.25 (d), 8.05 (d, 1H); 8.8 (d, 1H).

10. The starting pyridinium salt was obtained as follows: 5-Hydroxymethyl-6-methyluracil (15 mM) was suspended in glacial acetic acid (10 ml) and the mixture was saturated with HCl gas, then heated under reflux for ½ hour until the solid material was dissolved, and filtered. On cooling, 5-chloromethyl-6-methyluracil was obtained, n.m.r. in d$_6$ DMSO: 2.15 (s, 3H); 4.45 (s, 2H). This compound was treated with a solution of 4-methylthiopyridine in CH$_2$Cl$_2$, the solvent was evaporated, and the residue was heated at 100° for 10 minutes. It stayed solid throughout, but formed the required quaternary salt. Yield 93%. N.m.r. in d$_6$ DMSO: 2.25 (s, 3H); 2.65 (s, 3H); 5.3 (s, 2H); 7.8 (d, 2H); 8.7 (d, 2H). This material was oxidised to the required 4-methylsulphinyl starting material, as in Footnote 4.

11. N.m.r. in solvent A: 1.45 (2×s, 6H); 2.1 (s, 3H); 2.45 (s, 3H); 3.4 (q, 2H); 4.3 (q, 2H); 5.0 (d, 1H); 5.2 (s, 2H); 5.7 (d, 1H); 6.75 (s, 1H); 6.9 (q, 1H); 7.3 (q, 1H); 8.0 (q, 1H); 8.25 (q, 1H).

12. The starting pyridinium salt was obtained by the process of Footnote 4. N.m.r. of 4-methylthio pyridinium salt, in d$_6$ DMSO: 2.15 (s, 3H); 2.5 (s), 2.7 (s, 3H); 5.75 (s, 2H); 7.95 (d, 2H); 8.85 (d, 2H). The compound was oxidised to the required 4-methylsulphinyl starting material as in Footnote 4.

13. n.m.r. in solvent A: 0.8–1.0 (m, 4H); 1.45 (2×s, 6H); 1.9 (partially obscured by solvent peaks); 3.4 (q, 2H); 4.3 (q, 2H); 5.0 (s, 2H); 5.05 (d, 1H); 5.7 (d, 1H); 6.0 (s, 1H); 6.7 (s, 1H); 6.9 (d, 1H); 7.15 (d, 1H); 8.0 (d, 1H); 8.15 (d, 1H).

14. The starting pyridinium salt was obtained as follows: 6-Chloromethyl-2-cyclopropyl-4-hydroxypyridine (10 mM) and 4-methylthiopyridine (10 mM) were thoroughly mixed and heated at 100° for ½ hour. The mixture partly melted, then re-solidified. On cooling, the product was triturated with CH$_2$Cl$_2$ to give the 4-methylthiopyridinium salt. Yield 73%. N.m.r. in d$_6$ DMSO 0.6–1.1 (m, 4H); 2.0 (m, 1H); 2.7 (s, 3H); 5.55 (s, 2H); 6.2 (s, 1H); 7.95 (d, 2H); 8.7 (d, 2H). This product was oxidised to the required 4-methylsulphinyl pyridinium salt, as in Footnote 4.

15. N.m.r. in solvent A: 1.4 (s, 6H); 3.1 (s, 3H); 3.4 (q, 2H); 4.3 (q, 2H); 5.05 (d, 1H); 5.3 (s, 2H); 5.75 (d, 1H); 6.75 (s, 1H); 7.15 (d, 1H); 7.7 (d, 1H); 6.9–8.45 (m, 5H).

16. The starting pyridinium salt, in this case the tetrafluoroborate, was obtained by reacting 5-bromomethyl-1-methylisatin with 4-methylthiopyridine to give 1-(1-methyl-5-isatinylmethyl)-4-methylthiopyridinium bromide, m.p. 227.5–228.5 (crystallised from EtOH). This salt was dissolved in MeOH/H$_2$O, 1:1 v/v (30 ml) and the solution was stirred while silver tetrafluoroborate (1 mM) in water (5 ml) was added. The yellow silver bromide was filtered off through kieselguhr, the filter cake was suspended in water (5 ml) and again filtered, and the filtrates were combined and evaporated to give the required tetrafluoroborate salt.

EXAMPLES 244–245

7-[2-(2-aminothiazol-4-yl)-2-((Z)-1-carboxy-1-methylethoxyimino)acetamido]-3-ethylaminomethylceph-3-em-4-carboxylic acid (205 mg) was dissolved in a mixture of sodium bicarbonate (336 mg) in water (5 ml), and acetonitrile (5 ml). 4-Chloro-1-(4-nitrobenzyl)-pyridinium chloride (168 mg) was added, stirred for 10 minutes to achieve solution, then stood at room temperature overnight. The solvent was evaporated, and the residue was purified by running on an RP18 column (in sodium salt form), eluting with H$_2$O/CH$_3$CN, 100-70-:0-30, to give 7-[2-(2-aminothiazol-4-yl)-2-((Z)-1-carboxy-1-methylethoxyimino)acetamido]-3-[N-(1-p-nitrobenzyl-4-pyridinio)-N-ethyl]aminomethylceph-3-em-4-carboxylic acid. Yield 27.5%. N.m.r. in solvent A: 1.1 (t, 3H), 1.45 (2×s, 6H); 3.2–3.7 (m, 4H); 4.5–4.7 (q, 2H); 5.15 (d, 1H); 5.55 (s, 2H); 5.85 (d, 1H); 6.7 (s, 1H); 7.1–7.4 (m, 2H); 7.7 (d, 2H); 8.3 (d, 2H); 8.45 (d, 2H).

In a similar manner, using the corresponding N-carboxymethyl cephem, there was obtained 7-[2-(2-aminothiazol-4-yl)-2-((Z)-1-carboxy-1-methylethoxyimino)-acetamido]-3-[N-carboxymethyl-N-(1-p-nitrobenzyl-4-pyridinio]aminomethylceph-3-em-4-carboxylic acid. Yield 19%.

N.m.r. in solvent A: 1.4 (2×s, 6H); 3.25–3.6 (q, 2H); 4.4 (s, 2H); 4.6 (s, 2H); 5.15 (d, 1H); 5.55 (s, 2H); 5.85 (d, 1H); 6.7 (s, 1H); 7.05–7.2 (m, 1H); 7.4–7.55 (m, 1H); 7.6–7.7 (d, 2H); 8.2–8.3 (d, 2H); 8.4–8.6 (m, 2H).

EXAMPLES 246

The process of Example 244 was repeated, using the appropriate N-substituted cephem starting material, to give the following compound:

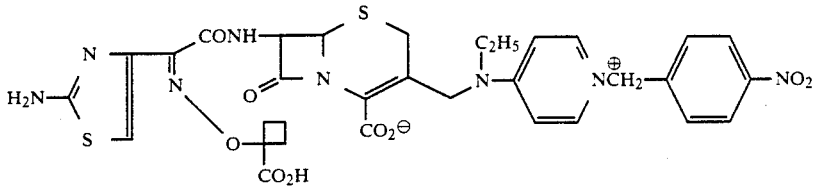

N.m.r. in solvent A: 1.15 (t, 3H); 1.7–1.9 (m, 2H); 2.2–2.5 (m, 4H); 3.0–3.5 (q, 2H); 3.5–3.8 (m, 2H); 4.4–4.8 (q, 2H); 5.05 (d, 1H); 5.5 (s, 2H); 5.7 (d, 1H); 6.7 (s, 1H); 7.05–7.25 (m, 1H); 7.6–7.7 (m, 3H); 8.2–8.3 (d, 2H); 8.35–8.4 (d, 2H).

EXAMPLE 247

3-Acetoxymethyl-7-[2-(2-aminothiazol-4-yl)-2-((Z)-1-carboxycyclobutyloxyimino)acetamido]ceph-3-em-4-carboxylic acid (460 mg) was suspended in water (20 ml) with sufficient NaHCO$_3$ to obtain a solution. 5-Amino-2-methylisoquinolinium iodide (244 mg) was added, and the solution was heated under argon for 3 hrs. at 85°, maintaining the pH at 7.5 by small additions of HOAc or aqueous NaHCO$_3$. The solution was cooled, made to pH5 with HOAc, and run onto a column of HP20SS resin. The column was eluted with H$_2$O/CH$_3$CN, 100-80:0-20. The fractions containing the product, 7-[2-(2-aminothiazol-4-yl)-2-((Z)-1-carboxycyclobutyloxyimino)acetamido]-3-[(2-methyl-5-isoquinolinio)aminomethyl]ceph-3-em-4-carboxylic acid, were combined and lyophilised. N.m.r. in solvent A: 1.85 (m, 2H); 2.35 (m, 4H); 3.45 (m, 2H); 4.4 (m, 2H); 4.4 (s, 3H); 5.05 (d, 1H); 5.75 (d, HH); 6.75 (s, 1H); 7.3 (d, 1H); 7.55 (d, 1H); 7.75 (t, 1H); 8.54 (d, 1H); 8.65 (d, 1H); 9.7 (s, 1H).

EXAMPLE 248

The process described in Example 221 was repeated, using 7-[2-(2-aminothiazol-4-yl)-2-((Z)-1-carboxy-1-methylethoxyimino)acetamido]-3-(3-pyridylmethylaminomethyl)ceph-3-em-4-carboxylic acid and 1-allyl-4-chloropyridinium bromide as starting materials, to give 3-[N-(1-allyl-4-pyridinio)-N-(3-pyridylmethyl)aminomethyl]-7-[2-(2-aminothiazol-4-yl)-2-((Z)-1-carboxy-1-methylethoxyimino)acetamido]ceph-3-em-4-carboxylic acid. N.m.r. in solvent A: 1.65 (s, 3H), 1.7 (s, 3H); 3.35 (d, 1H); 3.7 (d, 1H); 4.7–5.3 (m, 7H), 5.4 (d, 1H); 5.5 (d, 1H); 5.95 (d, 1H); 6.1 (m, 1H); 7.0 (s, 1H); 7.1–7.5 (br m, 2H); 7.65 (t, 1H); 8.0 (d, 1H); 8.3 (m, 2H); 8.7 (s, 2H).

The cephem starting material was obtained as in Example 62, Footnote 14.

1-Allyl-4-chloropyridinium bromide was obtained by quaternising 4-chloropyridine with allyl bromide.

EXAMPLE 249–254

The process described in Example 54 was repeated, to obtain the following compounds:

[Structure: cephem core with CONH at 7-position connected to aminothiazole-oxime side chain (H2N-thiazole-C(=N-OC(CH3)2CO2H)-CONH-), and at 3-position a CH2-NRR1 group]

| Example No. | R | R¹ | Yield % | Footnotes |
|---|---|---|---|---|
| 249 | Et | [thiazolo-pyridinium, N⊕ bridgehead with S] | 6 | 1,2 |
| 250 | Et | [pyrido-pyridinium / naphthyridinium, N⊕] | 22 | 3 |
| 251 | Et | [dihydrothiazolo-pyridinium, N⊕] | 26 | 4 |
| 252 | —(CH$_2$)$_2$CN | [dihydrothiazolo-pyridinium, N⊕] | 20 | 5 |
| 253 | H | [5-methylcinnolinium, N-CH$_3$⊕] | 9 | 6,7 |
| 254 | —(CH$_2$)$_2$CN | [pyridinium-N-CH$_2$CH=CH$_2$⊕] | 9 | 8 |

Footnotes

1. Initially, 1 eq. of quaternary heterocyclic salt and NaHCO$_3$ reacted with the CAZAMCA derivative, and further portions of salt and NaHCO$_3$ were subsequently added up to a total of 5 eq. and 10 eq. respectively.
2. Eluant portion 20-35:80-65:1. N.m.r. in solvent B : 1.85 (s, 3H); 1.55 (s, 6H); 3.5 (m, 2H); 3.7 (m, 2H); 4.55 (d, 1H); 5.15 (d, 1H); 5.2 (d, 1H); 5.8 (d, 1H); 7.05 (s, 1H); 7.45 (d, 1H); 7.8 (d, 1H); 8.2 (d, 1H); 9.0 (d, 1H).
3. Reaction was carried out in DMF, using 2 eq. of Et$_3$N in place of NaHCO$_3$. Eluant portion 25-30:75-70:1. N.m.r. in solvent B: 1.2 (t, 3H); 2.15 (s, 6H); 3.4–3.8 (m, 4H); 4.5–4.8 (m, 2H); 5.1 (d, 1H); 5.9 (d, 1H); 6.05 (m, 1H); 7.1 (s, 1H); 7.25 (s, 1H); 7.25 (m, 1H); 8.35 (d, 1H); 8.4 (m, 1H); 8.9 (m, 1H).
4. Reaction as in Footnote 3. Eluant proportion 20-25:80-75:1. N.m.r. in solvent B: 1.15 (t, 3H); 1.55 (s, 6H); 3.4 (q, 2H); 3.4–3.8 (m, 4H); 4.4–5.2 (m, 4H); 5.25 (d, 1H); 5.95 (d, 1H); 6.95 (d, 1H); 7.05 (s, 1H); 8.35 (d, 1H).
5. Reaction as in Footnote 3. Eluant proportion 20:80:1. N.m.r. in solvent B: 1.55 (s, 6H); 2.7–3.0 (m, 2H); 3.3–4.2 (m, 6H); 4.4–4.8 (m, 3H); 5.0–5.3 (m, 2H); 5.85 (d, 1H); 7.0 (s, 1H); 7.15 (s, 1H); 8.45 (d, 1H).
6. Reaction as in Footnote 1, for 2 hr. at room temperature. Eluant proportion as in Footnote 4. N.m.r. in solvent B: 1.55 (s, 6H); 3.55 (s, 2H); 4.55 (s, 2H); 4.7 (s, 3H); 5.2 (d, 1H); 5.85 (d, 1H); 7.05 (s, 1H); 7.15 (d, 1H); 7.35 (d, 1H); 8.05 (t, 1H); 8.85 (d, 1H); 9.35 (d, 1H).
7. The starting material quaternary heterocyclic salt was obtained from 5-aminocinnoline and methyl iodide. N.m.r. in solvent B: 4.65 (s, 3H); 7.2 (d, 1H); 7.25 (d, 1H); 7.95 (t, 1H); 8.9 (d, 1H); 9.25 (d, 1H).
8. Eluant was MeOH/aqueous ammonium carbonate buffer, 1.3:8.7 v/v. N.m.r. in solvent B; 1.55 (s, 6H); 2.7–2.9 (m, 2H); 3.3–3.7 (m, 2H); 3.8–4.1 (m, 2H); 4.6–5.0 (m, 4H); 5.2 (d, 1H); 5.2–5.4 (m, 2H); 5.9 (d, 1H); 7.0 (s, 1H); 7.3 (d, 1H); 8.3 (d, 1H).

EXAMPLE 255

The process described in Example 61, Footnote 13 was repeated, using 7-[2-(2-aminothiazol-4-yl)-2-((Z)-1-carboxycyclobutyloxyimino)acetamido]-3-ethylaminoethylceph-3-em-4-carboxylic acid as the cephem starting material, to give 3-[N-(1-[2-aminoethyl]-4-pyridinio)-N-ethylaminomethyl]-7-[2-((Z)-1-carboxycyclobutyloxyimino)acetamido]ceph-3-em-4-carboxylic acid. The product was purified by MPLC on a HP20SS column eluting with H$_2$O/CH$_3$CN, 100–93:0–7. N.m.r. in solvent A: 1.1 (t, 3H); 1.85 (m, 2H); 2.35 (m, 4H); 3.05 (d, 1H); 3.3 (m, 2H); 3.45 (d, 1H); 3.55–3.8 (m, 2H); 4.35–4.5 (m, 3H); 4.8 (d, 1H); 5.05 (d, 1H); 5.7 (d, 1H); 6.75 (s, 1H); 7.1 (m, 1H); 7.65 (m, 1H); 8.2 (d, 2H).

EXAMPLE 256

The general process described in Example 6 was repeated, using the appropriate heterocyclic starting material and cephem derivative, to give the following compound in 31% yield:

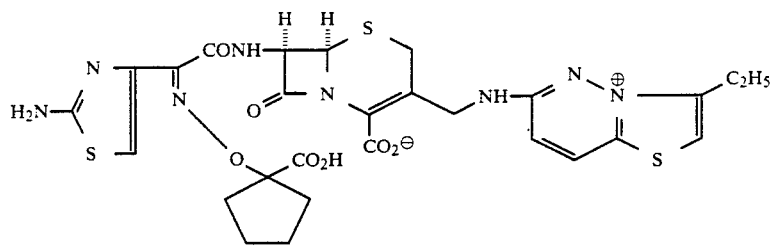

HPLC eluant MeOH/water/HOAc, 30-35:69-64:1 v/v/v.

N.m.r. in solvent B: 1.3 (t, 3H); 1.7 (m, 4H); 2.15 (m, 4H); 2.95 (q, 2H); 3.55 (m, 2H); 4.2 (d, 1H); 4.6 (d, 1H); 5.1 (d, 1H); 5.85 (d, 1H); 7.05 (s, 1H); 7.45 (d, 1H); 8.1 (s, 1H); 8.55 (d, 1H).

The starting material was 6-chloro-3-ethyl-thiazolo[3,2-b]pyridazinium perchlorate which was prepared by the general procedure described in J. Org. Chem., 34, 996, (1964).

EXAMPLE 257

The process described in Example 247 was repeated, using the appropriate 3-acetoxymethyl cephem and 5-amino-2-methylisoquinolinium iodide as starting materials. The reaction was carried out in water at pH 7.5 (adjusted by addition of HOAc or NaHCO3 as necessary), for 2.5 hrs. at 80°. HPLC eluant was MeOH/H2O/HOAc, 30-35:69-64:1 v/v/v. N.m.r. in solvent B: 1.7 (m, 4H); 2.15 (m, 4H); 3.6 (m, 2H); 4.4 (m, 5H); 5.15 (d, 1H); 5.85 (d, 1H); 7.05 (s, 1H); 7.15 (d, 1H); 7.5 (d, 1H); 7.6 (dd, 1H); 7.75 (dd, 1H); 8.5 (d, 1H); 8.65 (d, 1H); 9.75 (s, 1H).

The cephalosporin starting material may be obtained as follows:

To a stirred mixture of DMF (0.85 ml) in anhydrous CH2Cl2 (40 ml) at −10° C. was added dropwise a solution of oxalyl chloride (0.87 ml) in anhydrous CH2Cl2 (10 ml). Stirring was continued at −10° C. for 30 minutes. To this stirred suspension was added in one portion 2-[(Z)-(tert-butoxycarbonyl)cyclopentyloxyimino]-2-(2-tritylaminothiazol-4-yl)acetic acid (5.97 g) followed by N-methylmorpholine (1.32 ml). Stirring was continued for 30 minutes at −10° C.

In another flask a suspension of 7-aminocephalosporanic acid (2.72 g) in anhydrous CH2Cl2 (25 ml) was stirred for 1 hour with N,O-bis (trimethylsilyl) acetamide (4 ml) to give a clear solution. This was transferred by syringe to the above acid chloride solution which was stirred at −10° C. during the addition. The reaction mixture was then allowed to warm to room temperature and stirred for a further 1.5 hours. The reaction mixture was poured into water and extracted with CH2Cl2. The combined CH2Cl2 extracts were washed with water, dried (MgSO4) and the solvent was evaporated under reduced pressure to yield a foam. The crude product was dissolved in EtOAc and applied to a column of Kieselgel 60. Elution with EtOAc gave, after precipitation from CH2Cl2 with n-hexane, 3-acetoxymethyl-7-[2-(2-tritylaminothiazol-4-yl)-2-((Z)-1-tert-butoxycarbonyl)cyclopentyloxyimino)acetamido]ceph-3-em-4-carboxylic acid (6.6 g) as a white solid. This compound, (2.61 g) was then stirred for 1 hour at 0° C. with a mixture of TFA (12 ml) and water (1.2 ml). The reaction mixture was evaporated to dryness, the residue taken up in water and extracted with EtOAc. The solvent was evaporated under reduced pressure to give a solid which was dissolved in a minimum MeOH and precipitated with ether to give 3-acetoxymethyl-7-[2-(2-aminothiazol-4-yl)-2-((Z)-1-carboxy-1-cyclopentyloxyimino)acetamido]ceph-3-em-4-carboxylic acid (1.1 g) as a white solid having the following n.m.r. in solvent B: 1.7 (m, 3H); 1.95 (s, 3H); 2.15 (m, 4H); 3.4 (d, 1H); 3.65 (d, 1H); 4.7 (d, 1H); 4.95 (d, 1H); 5.15 (d, 1H); 5.85 (d, 1H); 7.05 (d, 1H).

EXAMPLE 258

Method A of Example 108 was repeated, using the appropriate starting materials, and water as solvent to give the compound:

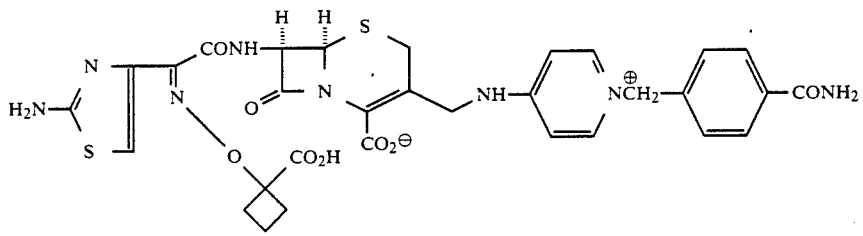

in 17.5% yield. N.m.r. in solvent B: 2.4-2.7 (m, 4H); 3.4-3.85 (ABq, 2H); 4.3-4.7 (Abq, 2H); 5.25 (d, 1H); 5.55 (s, 2H); 5.9 (d, 1H); 6.95 (s, 1H); 7.15 (d, 1H); 7.35-7.5 (m, 1H); 7.6 (d, 2H); 8.05 (d, 2H); 8.3 (d, 1H); after MPLC on HP20SS (as the sodium salt), and precipitation from aqueous solution with acetic acid.

The starting quaternary pyridinium salt was the tetrafluoroborate described in Example 243, Footnote 16.

EXAMPLE 259

The process described in Example 221 was repeated, using the appropriate 3-ethylaminomethyl cephem and 1-methyl-4-methylthioquinazolinium iodide, to give

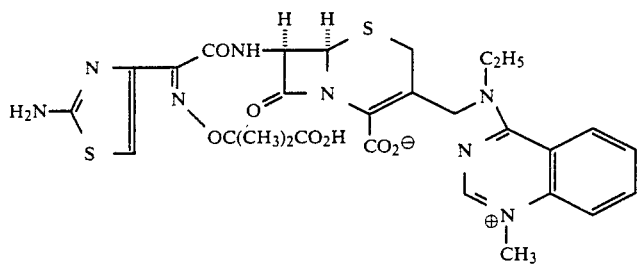

n.m.r. in solvent A: 1.4 (br s, 9H); 3.1–3.5 (dd, 2H); 3.98 (br s, 5H); 5.04 (d, 1H); 5.1–5.5 (m, 2H); 5.68 (d, 1H); 6.71 (s, 1H); 7.8 (t, 1H); 7.99 (d, 1H); 8.12 (t, 1H); 8.28 (d, 1H); 8.85 (s, 1H).

EXAMPLE 260

The process described in Example 236 was repeated, using the appropriate 3-aminomethyl cephem and 1-furfuryl-4-methylsulphinylpyridinium chloride, to give in 20% yield, n.m.r. spectrum in solvent A: 0.93 (t, 3H); 1.1 (t, 3H); 1.78 (quintet, 2H); 3.2 (d, 1H); 3.43 (d, 1H); 3.64 (m, 2H); 4.29 (s, 3H); 4.43 (t, 1H); 4.55 (d, 1H); 4.69 (d, 1H); 5.04 (d, 1H); 5.73 (d, 1H); 6.76 (s, 1H); 8.05 (m, 2H); 8.93 (t, 1H). Retention time 5.3 minutes on a reversed phase Partisil PXS 10/25 ODS-2 column, using MeOH/water/TFA 40:60:0.2 v/v/v as eluant.

The cephalosporin starting material may be prepared as follows: To a stirred solution of 3-aminomethyl-7-[2-(2-aminothiazol-4-yl)-2-((Z)-1-carboxypropox-

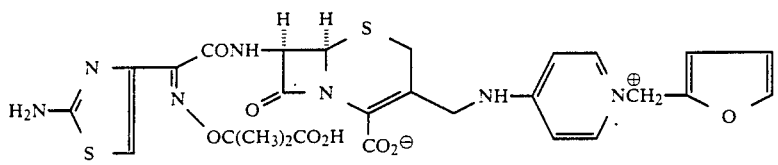

n.m.r. in solvent A: 1.42 2xs 6H ; 3.35 q, 2H ; 4.3 (q, 2H); 5.01 (d, 1H); 5.37 (s, 2H); 5.67 (d, 1H); 6.45 (q, 1H); 6.62 (d, 1H); 6.73 (s, 1H); 6.93 (m, 1H); 7.4 (m, 1H); 7.64 (m, 1H); 8.12 (d, 1H); 8.28 (d, 1H).

The starting pyridinium salt was obtained by the general process described in Example 237, Footnote 4. The 1-furfuryl-4-methylthiopyridinium chloride had n.m.r. in $d_6$-DMSO: 2.72 (s, 3H); 5.92 (s, 2H); 6.52 (q, 1H); 6.84 (d, 1H); 7.75 (m, 1H); 8.0 (d, 2H); 8.96 (d, 2H). This compound was oxidised to the required sulphoxide, as described in Example 237, Footnote 4, and used without further purification.

EXAMPLE 261

The process described in Examples 1 to 4 was repeated, using the appropriate 3-ethylaminomethyl cephem and 3-chloro-1-methylpyridazinium iodide. The reaction was carried out for 18 hrs. at room temperature before quenching with HOAc, and isolating the product by chromatography on Diaion CHP20P resin, to give, in 51% yield, the more polar isomer of yimino)acetamido]ceph-3-em-4-carboxylic acid (more polar isomer, 2.6 g) in 2.5% (w/v) pH 5.5 sodium acetate buffer (50 ml) was added sodium cyanoborohydride (0.34 g), followed by acetaldehyde (0.3 ml) in water (5 ml) over 40 minutes. The reaction mixture was then concentrated, diluted to 50 ml with water, and the pH adjusted to 3.5 with HOAc. Careful chromatography on Diaion HP20SS, eluting with $H_2O/CH_3CN$, (92.5:7.5) gave 7-[2-(2-aminothiazol-4-yl)-2-((Z)-1-carboxypropoxyimino)acetamido]-3-ethylaminomethyl-ceph-3-em-4-carboxylic acid, having the following n.m.r. spectrum in solvent A: 0.96 (t, 3H); 1.18 (t, 3H); 1.81 (quintet, 2H); 2.94 (q, 2H); 3.38 (d, 1H); 3.42 (d, 1H); 3.61 (d, 1H); 3.78 (d, 1H); 4.46 (t, 1H); 5.03 (d, 1H); 5.76 (d, 1H); 6.88 (s, 1H). Retention time 4.2 minutes on a reversed phase Partisil PXS 10/25 ODS-2 column, using MeOH/$H_2O$/HOAc, 30:70:1, v/v/v, as eluant.

EXAMPLE 262

The general process described in Example 244 was repeated, using 1-(4-carbamoylbenzyl)-4-chloropyridinium bromide as the starting material, to give

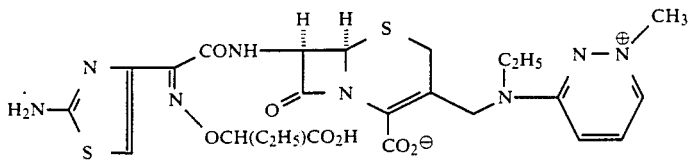

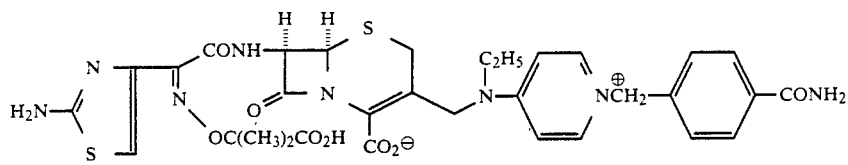

n.m.r. in solvent A: 1.05-1.2 (t, 3H); 1.4 (2×s, 6H); 3.2-3.7 (m, 4H); 4.45-4.7 (q, 2H); 5.15 (d, 1H); 5.45 (s, 2H); 5.8 (d, 1H); 6.7 (s, 1H); 7.0-7.4 (m, 2H); 7.4-7.5 (d, 2H); 7.85-7.95 (d, 2H); 8.35-8.45 (d, 2H).

The starting pyridinium salt was obtained by quaternising 4-chloropyridine with 4-bromomethylbenzamide in DMF at room temperature for 4 hours.

EXAMPLES 263-269

The general procedure described in Examples 1-4 was repeated, except that the solvent was DMF and the base was $Et_3N$. The appropriate 3-ethylaminomethyl-cephalosporin was used, and products were purified by chromatography on Diaion CHP20P resin. Retention times are quoted for a reversed phase Partisil PXS 10/25 ODS-2 column.

The following compounds were made:

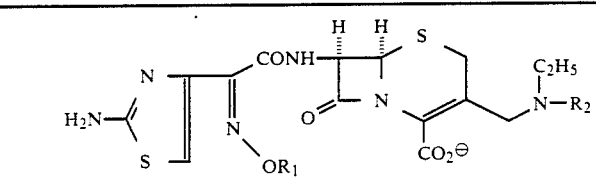

| Example | $R_1$ | $R_2$ | Yield (%) | Footnotes |
|---|---|---|---|---|
| 263 | $C_2H_5$<br>\|<br>—CH—$CO_2H$<br>(m.p. isomer) | N—N⊕(CH₃)<br>with NH₂ substituted ring | 19 | 1,2,3 |
| 264 | $CH_3$<br>\|<br>—CH—$CO_2H$<br>(m.p. isomer) | N—N⊕(CH₃)<br>with NH₂ substituted ring | 5 | 1,4,5 |
| 265 | $C_2H_5$<br>\|<br>—CH—$CH_2H$<br>(m.p. isomer) | pyridazine-S ring with N⊕ | 12 | 6,7,8 |
| 266 | $C_2H_5$<br>\|<br>—CH—$CO_2H$<br>(m.p. isomer) | thieno-pyrimidinium ring with N⊕—$CH_3$ | 60 | 7,9,10 |
| 267 | $CH_3$<br>\|<br>—CH—$CO_2H$<br>(m.p. isomer) | bicyclic N,S ring with N⊕ | 50 | 7,11,12 |
| 268 | $CH_3$<br>\|<br>—CH—$CO_2H$<br>(m.p. isomer) | pyridinium ring with N⊕—$CH_2$—CH=$CH_2$ | 50 | 13,14,15 |

-continued

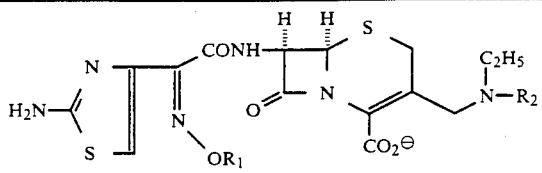

| Example | R₁ | R₂ | Yield (%) | Footnotes |
|---|---|---|---|---|
| 269 | $-\underset{\underset{CH_3}{|}}{CH}-CO_2H$ (m.p. isomer) | pyridinium-$NCH_2$-C₆H₄-$NO_2$ | 56 | 16,17,18 |

1. Starting material was 6-amino-1-methylpyridazinium tetrafluoroborate.
2. Reaction mixture heated 24 hours at 45° C. before quenching with acetic acid
3. N.m.r. in solvent A: 0.93 (t, 3H), 1.04 (t, 3H), 1.8 (m, 2H), 3.27 (d, 1H), 3.44 (d, 1H), 3.48 (m, 2H), 3.75 (s, 3H), 4.32 (d, 1H), 4.47 (t, 1H), 4.57 (d, 1H), 5.07 (d, 1H), 5.88 (d, 1H), 6.88 (s, 1H), 7.36 (d, 1H), 7.75 (d, 1H). Retention time 4.6 minutes, eluting with MeOH/H₂O/HOAc, 40:60:1, v/v/v.
4. Reaction mixture heated at 65° C. for 3 hours before quenching with acetic acid. After a preliminary purification on Diaion CHP20P, the product was re-purified by preparative HPLC on a reversed phase Partisil ODS2 column, eluting in MeOH/H₂O/HOAc, 75:25:1 v/v/v.
5. N.m.r. in solvent A: 1.05 (t, 3H), 1.39 (d, 3H), 3.24 (d, 1H), 3.43 (d, 1H), 3.48 (m, 2H), 3.74 (s, 3H), 4.31 (d, 1H), 4.53 (d, 1H), 4.6 (q, 1H), 5.07 (d, 1H), 5.75 (d, 1H), 6.87 (s, 1H), 7.33 (d, 1H), 7.88 (d, 1H). Retention time 4.5 minutes, eluting with MeOH/water/HOAc, 65:35:1, v/v/v.
6. Starting material 6-fluoro-thiazolo[3,2-b]pyridazinium perchlorate.
7. Reaction carried out at ambient temperature for 18 hours before quenching with HOAc.
8. N.m.r. in solvent A: 0.92 (t, 3H), 1.15 (t, 3H), 1.79 (m, 2H), 3.32 (d, 1H), 3.51 (d, 1H), 3.68 (m, 2H), 4.45 (t, 1H), 4.58 (d, 1H), 4.79 (d, 1H), 5.05 (d, 1H), 5.77 (d, 1H), 6.76 (s, 1H), 7.89 (d, 1H), 8.46 (d, 1H), 8.76 (d, 1H), 8.78 (d, 1H). Retention time 4.7 minutes, eluting with MeOH/H₂O/HOAc, 40:60:1, v/v/v.
9. Starting material was 1-methyl-4-methylthiothieno[2,3-d]pyrimidinium tetrafluoroborate
10. N.m.r. in solvent A: 0.9 (t, 3H), 1.3 (m, 3H), 1.77 (m, 2H), 3.24 (d, 1H), 3.46 (d, 1H), 3.98 (m, 2H), 4.0 (s, 3H), 4.44 (t, 1H), 4.84 (d, 1H), 5.06 (d, 1H), 5.25 (d, 1H), 5.77 (d, 1H), 6.76 (s, 1H), 7.76 (d, 1H), 7.87 (d. 1H), 8.77 (s, 1H). Retention time 4.1 minutes, eluting with MeOH/H₂O/TFA, 45:65:0.1, v/v/v.
11. Starting material was 6,7-dihydro-2-methylthio-thiazolo [3,2-a] pyrimidinium tetrafluoroborate.
12. N.m.r. in solvent A: 1.11 (t, 3H), 1.39 (d, 3H), 3.16 (d, 1H), 3.43 (d, 1H), 3.66 (m, 4H), 4.6 (m, 4H), 4.96 (d, 1H), 5.06 (d, 1H), 5.78 (d, 1H), 6.77 (s, 1H), 6.83 (d, 1H), 8.23 (d, 1H). Retention time 5.0 minutes, eluting with MeOH/H₂O/TFA, 40:60:0.2, v/v/v.
13. Prepared by the standard aqueous/DMF conditions of Examples 1–4, except that the reaction was carried out for 65 hours at ambient temperature before quenching with HOAc.
14. Starting material was 1-allyl-4-chloropyridinium tosylate.
15. N.m.r. in solvent A: 1.12 (t, 3H), 1.39 (d, 3H), 3.15 (d, 1H), 3.45 (d, 1H), 3.63 (m, 2H), 4.5 (d, 1H), 4.58 (q, 1H), 4.71 (d, 1H), 4.78 (d, 1H), 5.06 (d, 1H), 5.25 (d, 1H), 5.33 (d, 1H), 5.77 (d, 1H), 6.03 (m, 1H), 6.75 (s, 1H), 7.1 (br, 1H), 7.4 (br, 1H), 8.19 (d, 2H). Retention time 3.9 minutes, eluting with MeOH/H₂O/TFA, 40:60:0.1, v/v/v.
16. Prepared using the procedure of Footnote 13 above, except that the crude product was chromatographed without acidification on CHP20P, to give the product as a mono-sodium salt, after precipitation from water by acetone.
17. Starting material was 4-chloro-1-(4-nitrobenzyl)-pyridinium tosylate.
18. N.m.r. in solvent A: 1.11 (t, 3H), 1.37 (d, 3H), 3.1 (d, 1H), 3.51 (d, 1H), 3.76 (m, 2H), 4.48 (d, 1H), 4.57 (q, 1H), 4.77 (d, 1H), 5.0 (d, 1H), 5.52 (s, 2H), 5.7 (d, 1H), 6.75 (s, 1H), 7.1 (br, 1H), 7.55 (br, 1H), 7.63 (d, 2H), 8.25 (d, 2H), 8.36 (d, 2H). Retention time 8.5 minutes in MeOH/H₂O/TFA, 40:60:0.2, v/v/v.

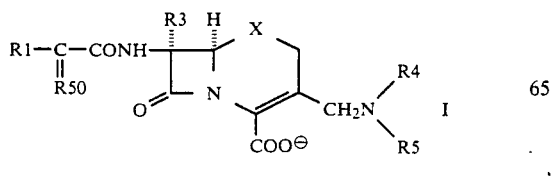

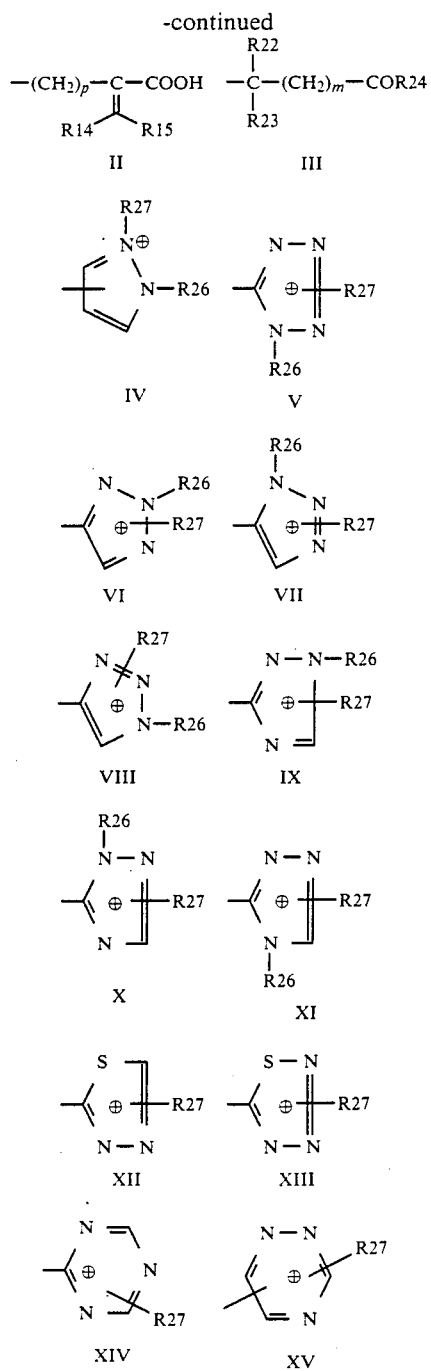

-continued

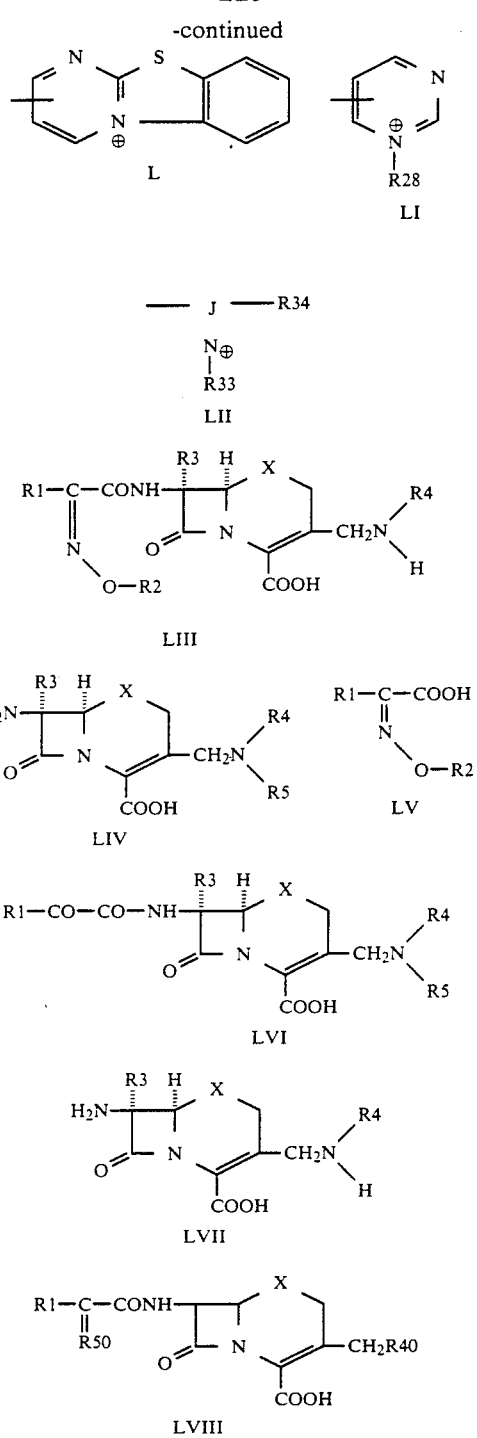

What we claim is:

1. A cephalosporin derivative of the formula I:

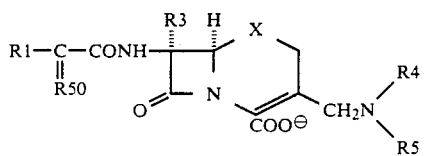

in which X is sulphur or sulphinyl (R or S configuration);

R1 is 2-aminothiazol-4-yl or 2-aminooxazol-4-yl each optionally substituted in the 5-position by fluorine, chlorine or bromine, or R1 is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R50 is chloromethylene or a radical of the formula =N.O.R2, wherein R2 is hydrogen, (1–6C)alkyl, (3–8C)cyclo-alkyl, (1–3C)alkyl(3–6C)cycloalkyl, (3–6C)cycloalkyl(1–3C)alkyl, (3–6C)alkenyl, optionally substituted by carboxy, (5–8C)cycloalkenyl, (3–6C)alkynyl, (2–5C)alkylcarbamoyl, phenylcarbamoyl, benzylcarbamoyl, (1–4C)alkylcarbamoyl(1–4C)alkyl, di(1–4C)alkylcarbamoyl(1–4C)alkyl, (1–4C)haloalkylcarbamoyl(1–4C)alkyl, triphenylmethyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, (2–6C)aminoalkyl, (1–4C)alkyl-amino(1–6C)alkyl, (2–8C)dialkylamino(2–6C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl or 2-oxotetrahydrofuran-3-yl, or —R2 is the formula —(CH$_2$)$_n$—R6 in which n is 1 to 4 and R6 is piperidino, pyrrolidino, morpholino, piperazino or N-methylpiperazine, each value of R6 being optionally substituted by (1–4C)alkyl, phenyl or benzyl, or —R2 is of the formula —(CH$_2$)$_m$—W—R7 in which m is 0 to 3, W is sulphur or a direct bond, and R7 is phenyl or pyridinio(1–4C)alkylene or R7 is pyridyl, imidazolyl, 1,3,4-thiadiazolyl, tetrazolyl, 1-(1–4C)alkyltetrazolyl, thiazolyl, isothiazolyl or isoxazolyl in which the link with W is via a carbon or uncharged nitrogen, each value of R7 being optionally substituted, where possible, by one or two groups selected from (1–4C)alkyl, amino, hydroxy, carboxy, carbamoyl, nitro, (2–5C)alkoxycarbonyl, cyano or sulpho, or —R2 is of the formula —(CH$_2$)$_n$—CO—R8 in which n is 1 to 4 and R8 is (1–4C)alkyl, phenyl or benzyl, or —R2 is of the formula —COR9 or —(CH$_2$)$_n$—OCO—R9 in which n is 1–4 and R9 is hydrogen, (1–4C)alkyl, (1–4C)haloalkyl, phenyl or benzyl, or —R2 is of the formula —G—CH$_2$—R10 in which G is carbonyl or a direct bond and R10 is phthalimido, or —R2 is of the formula II:

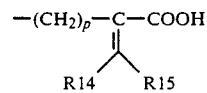

in which p is 1 or 2 and R14 and R15 are hydrogen or (1–4C)alkyl, or —R2 is of the formula —P(O)R16R17 in which R16 is hydroxy, (1–4C)alkoxy, (2–8C)dialkylamino, phenoxy, phenylamino or one of the values given above for R6, and R17 is (1–4C)alkyl, (1–4C)alkoxy, (2–8C)dialkylamino, phenoxy, phenylamino, piperidino, pyrrolidino, morpholino, piperazino or N-methylpiperazino, or —R2 is of the formula —CH₂P(O)R18R19 in which R18 and R19 are hydroxy or (1-4C)alkoxy,
or —R2 is of the formula —CH(SR20)COOR21 in which R20 is (1-4C)alkyl and R21 is hydrogen or (1-6C)alkyl,
or —R2 is of the formula III:

(III)

in which m is 0–3, R22 is hydrogen, (1-3C)alkyl or methylthio, R23 is hydrogen, (1-3C)alkyl, (C₃-C₇-)cycloalkyl, cyano, carboxy, (2-5C)carboxyalkyl or methanesulfonylamino, or phenyl optionally substituted by amino or hydroxy, or R22 and R23 are joined to form, together with the carbon to which they are attached, a (3-7C) carbocyclic ring, and R24 is hydroxy, amino, (1-4C)alkoxy, (1-4C)alkylamino, phenylamino or of the formula R6 given above or of the formula NHOR25 in which R25 is hydrogen, (1-4C)alkyl, phenyl or benzyl, provided that when R2 contains phenyl, and unless otherwise stated, the phenyl is optionally substituted by 1 or 2 groups selected from halogen, hydroxy, amino, carboxy, nitro, carbamoyl, cyano and aminomethyl;

R3 is hydrogen or methoxy;

R4 is hydrogen, (1-4C)alkyl, halo(1-4C)alkyl, hydroxy(1-4C)alkyl, (1-4C)alkoxy(1-4C)alkyl, carboxy (1-4C)alkyl, amino(1-4C)alkyl, cyano(1-4C)alkyl, (1-4C)alkanoylamino(1-4C)alkyl, allyl, furfuryl, benzyl or pyridyl(1-4C)alkyl;

R5 is an aromatic heterocyclic ring system which is linked via carbon and is one of the formula IV to L, excluding XLII,

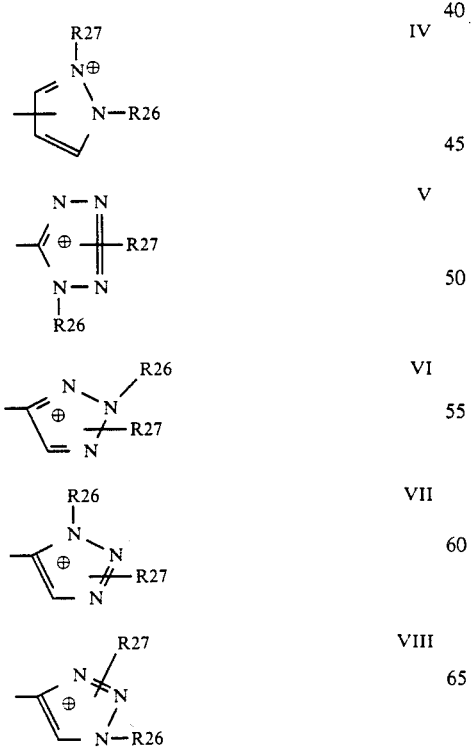

IV

V

VI

VII

VIII

-continued

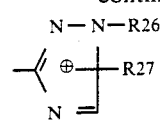 IX

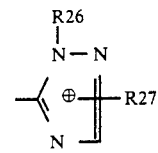 X

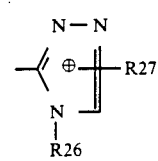 XI

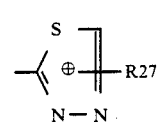 XII

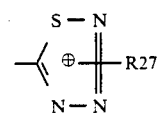 XIII

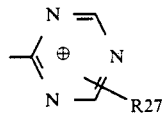 XIV

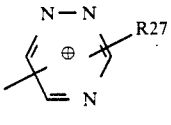 XV

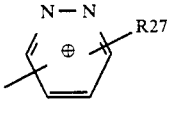 XVI

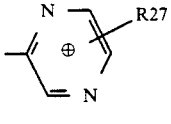 XVII

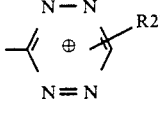 XVIII

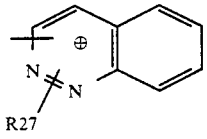 XIX

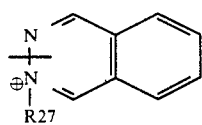 XX

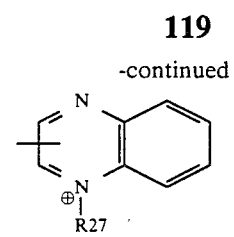 XXI
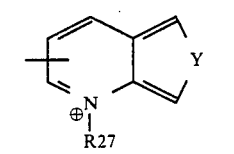 XXII
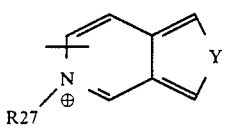 XXIII
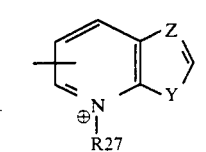 XXIV
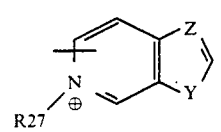 XXV
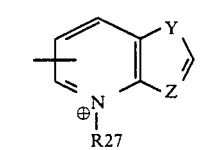 XXVI
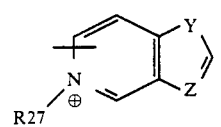 XXVII
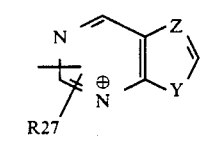 XXVIII
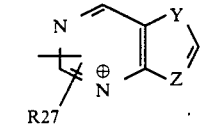 XXIX
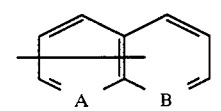 XXX
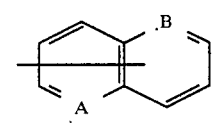 XXXI
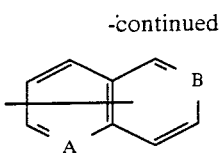 XXXII
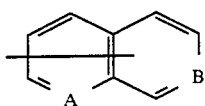 XXXIII
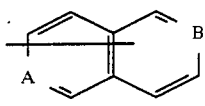 XXXIV
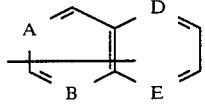 XXXV
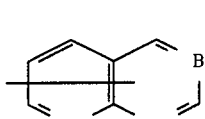 XXXVI
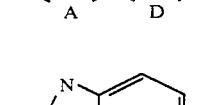 XXXVII
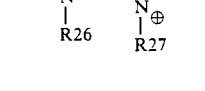 XXXVIII
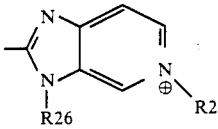 XXXIX
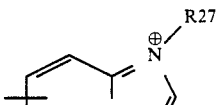 XL
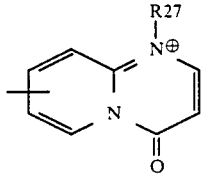 XLI
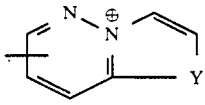 XLIII -continued

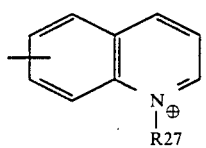
XLIV (Linked through benzene ring)

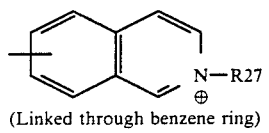
XLV (Linked through benzene ring)

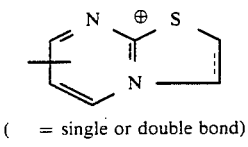
XLVI ( = single or double bond)

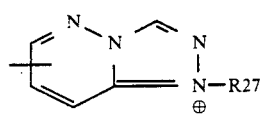
XLVII

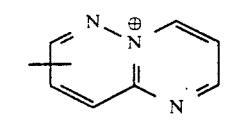
XLVIII

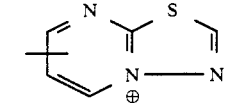
XLIX

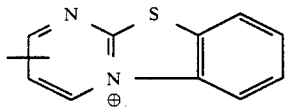
L each of these ring systems being optionally substituted where possible, on a carbon atom or atoms, by one, two or three substituents selected from halogen, (1-6C)alkyl, carboxy, (2-6C)alkoxycarbonyl, (2-6C)-alkoxycarbonyl(1-4C)alkyl, (1-6C)alkoxy, (1-6C)alkylthio, cyano, (2-4C)cyanoalkyl, amino, (1-6C)alkylamino, (2-8C)dialkylamino, benzylamino (optionally substituted in the benzene ring thereof by nitro), thenylamino, allylamino, (1-6C)aminoalkylamino, (1-6C)alkoxy(1-6C)alkylamino, (1-6C)hydroxyalkylamino, hydroxy, mercapto, carbamoyl, (2-6)alkylcarbamoyl, (3-10C)dialkylcarbamoyl, phenylthio and heteroarylthio wherein heteroaryl is a 5- or 6-membered ring containing 1, 2 or 3 hetero atoms selected from oxygen, nitrogen and sulphur;
and in which Y is oxygen, sulphur or NR27;
Z is hydrogen or CH;
one of A, B, D and E is +NR27 and the remainder are nitrogen;
and ring systems of Formula IV, XVI or XVII,

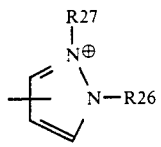
IV

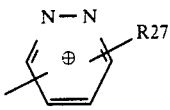
XVI

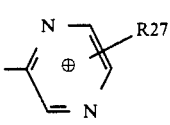
XVII which are optionally fused, or a carbon-carbon bond, with 5- or 7-membered saturated carbocyclic ring;
R27 is nitrogen-linked and is (1-6C)alkyl, (1-6C)alkyl(2-6C)alkenyl, (2-6C)alkenyl, (2-8C)alkoxyalkyl, carboxy(1-6C)alkyl, [(1-6C)alkoxy]carbonyl(1-6C)alkyl, carbamoyl(1-6C)alkyl, carboxyaminocarbonyl(1-6C)alkyl, [(1-6C)alkoxy]carbonylamino-carbonyl(1-6C)alkyl, [(2-8C)alkanoyl]methyl, benzoylmethyl, (1-6C)hydroxyalkyl, (1-6C)alkylamino, or phenyl(1-6C)alkyl or phenyl, each optionally substituted by 1 or 2 groups selected from halogen, hydroxy, amino, carboxy, nitro, carbamoyl, cyano, trifluoromethyl, and aminomethyl;
R26 is hydrogen, (1-6C)alkyl, phenyl or benzyl;
and the salts formed with acids and bases which afford pharmaceutically acceptable anions and cations, respectively.

2. The cephalosporin derivative according to claim 1 wherein $R^5$ is of the formula XXII to XXIX.

3. The cephalosporin derivative according to claim 1 wherein $R^5$ is of the formula XXX to XXXVII.

4. The cephalosporin derivative according to claim 1, wherein $R^5$ is of the formula XL to XLI.

5. The cephalosporin derivative according to claim 1, wherein $R^5$ is of the formula XLIII, XLVI to L.

6. The cephalosporin derivative according to claim 1, wherein $R^5$ is of the formula XLIV to XLV.

7. The cephalosporin derivative according to claim 1, wherein $R^5$ is of the formula XXXVIII to XXXIX.

8. The cephalosporin derivative according to claim 1, wherein $R^5$ is of the formula IV.

9. The cephalosporin derivative according to claim 1, wherein $R^5$ is of the formula V.

10. The cephalosporin derivative according to claim 1, wherein $R^5$ is of the formula VI to XI.

11. The cephalosporin derivative according to claim 1, wherein $R^5$ is of the formula XII to XIII.

12. The cephalosporin derivative according to claim 1, wherein $R^5$ is of the formula XIV to XV or XVIII.

13. A cephalosporin derivative as claimed in claim 1 wherein the ring substituents are selected from chlorine, fluorine, methyl, ethyl, n-propyl, isopropyl, carboxy, methoxycarbonylmethyl, ethoxycarbonylmethyl, methoxy, ethoxy, methylthio, amino, isopropylamino, dimethylamino, p-nitrobenzylamino, allylamino, 2-aminoethylamino, 2-methoxyethylamino, 2-hydroxyethylamino and hydroxy;
R27 is (1-6C)alkyl, allyl or phenyl optionally substituted by nitro or trifluoromethyl; and R4 is hydrogen, (1-4C)alkyl, halo(1-4C)alkyl, hydroxy(1-4C)alkyl, (1-4C)alkoxy(1-4C)alkyl, carboxy(1-4C)alkyl, amino(1-4C)alkyl, cyano(1-4C)alkyl, (1-4C)alkanoylamino(1-4C)alkyl, allyl, furfuryl, benzyl or pyridyl(1-4C)alkyl.

14. A cephalosporin derivative as claimed in claim 13 wherein the ring substituents are selected from chlorine, fluorine, methyl, ethyl, n-propyl, isopropyl, carboxy, methoxycarbonylmethyl, ethoxycarbonylmethyl, methoxy, ethoxy, methylthio, amino, isopropylamino, dimethylamino, p-nitrobenzylamino, allyamino, 2-aminoethylamino, 2-methoxyethylamino, 2-hydroxyethylamino and hydroxy; and R4 is hydrogen, methyl, ethyl, 2-fluoroethyl, 2-chloroethyl, 2-hydroxyethyl, 2-methoxyethyl, carboxymethyl, 2-aminoethyl, 2-cyanoethyl, 2-formamidoethyl, allyl, furfuryl, benzyl or 4-pyridylmethyl.

15. A cephalosporin derivative as claimed in claim 1 wherein R5 is of the formula XVI wherein the ring is substituted by (1-6C)alkyl and/or amino; of the formula XXVIII wherein Y is sulphur, Z is CH2 and R27 is (1-6C)alkyl; or of the formula XLIII wherein Y is sulphur; of the formula XLVI wherein the optional bond is a double bond; of the formula XLVII wherein R27 is methyl.

16. A pharmaceutical composition having antibacterial properties, which comprises a cephalosporin derivative as claimed in claim 1 in association with a pharmaceutically-acceptable diluent or carrier.

17. A method of treating a bacterial infection in an animal host which comprises administering to said host an antibacterially effective amount of a cephalosporin derivative as claimed in claim 1.

18. A cephalosporin derivative of the formula I:

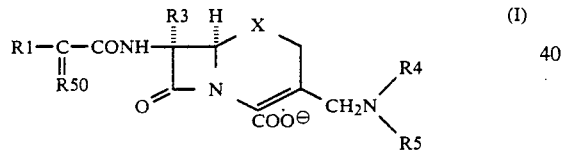

in which X and R1 have the meanings stated in claim 1:

R50 is chloromethylene or a radical of the formula =N.O.R2, wherein R2 is hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, ally, cyclopentenyl, cyclohexenyl, propargyl, methylcarbamoyl, ethylcarbamoyl, phenylcarbamoyl, benzylcarbamoyl, triphenylmethyl, 2-chloroethyl, 2-fluoroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidinothio)ethyl, 2-(N-aminoamidinothio)ethyl, tetrahydropyran-2-yl, thietan-3-yl, or 2-oxo-tetrahydrofuran-3-yl, or R2 is the formula —(CH2)n—R6 in which n is 1 to 4 and R6 is piperidino, pyrrolidino, morpholino, piperazino or N-methylpiperazine, each optionally substituted by methyl, phenyl or benzyl, or R2 is of the formula —(CH2)m—W—R7 in which m is 0 to 3, W is sulphur or a direct bond, and R7 is phenyl, pyridiniomethylene, 2-pyridinioethylene or pyridyl, imidazolyl, 1,3,4-thiadiazolyl, tetrazolyl, 1-methyltetrazolyl, thiazolyl, isothiazolyl or isoxazolyl in which the link with W is via a carbon or uncharged nitrogen, and each value of R7 is optionally substituted, where possible, by one or two groups selected from methyl, amino, hydroxy, carboxy, carbamoyl, nitro, methoxycarbonyl, ethoxycarbonyl, cyano or sulpho, or R2 is of the formula —(CH2)n—CO—R8 in which n is 1 to 4, and R8 is methyl, ethyl, phenyl or benzyl, or R2 is of the formula —COR9 or —(CH2)n—OCO—R9 in which n is 1-4, and R9 is hydrogen, methyl, chloromethyl, bromomethyl, 2-chloroethyl, 2-bromoethyl, phenyl or benzyl, or R2 is of the formula —G—CH2—R10, in which G is carbonyl or a direct bond and R10 is phthalimido, or R2 is of the formula II:

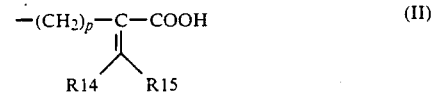

in which p is 1 or 2, and R14 and R15 are hydrogen or methyl, or R2 is of the formula —P(O)R16R17 in which R16 is hydroxy, methoxy, ethoxy, dialkylamino, diethylamino, phenoxy, phenylamino, or one of the particular values given above for R6, and R17 is methyl, ethyl, methoxy, ethoxy, dialkylamino, diethylamino, phenoxy, phenylamino, piperidino, pyrrolidino, morpholino, piperazino or N-methylpiperazino, or R2 is of the formula —CH2P(O)R18R19, in which R18 and R19 are hydroxy, methoxy or ethoxy, or R2 is of the formula —CH(SR20)COOR21 in which R20 is methyl or ethyl and R21 is hydrogen, methyl, ethyl or isopropyl, or R2 is of the formula III:

in which m is 0-3, R22 is hydrogen, methyl or methylthio, R23 is hydrogen, methyl, cyclopropyl, cyclobutyl, cyclopentyl, cyclohexyl, cyano, carboxy, carboxymethyl, 2-carboxyethyl or methanesulfonylamino, or phenyl optionally substituted by amino or hydroxy, or R22 and R23 are joined to form, together with the carbon to which they are attached, a cyclopropane, cyclobutane, cyclopentane, cyclohexane or cycloheptane ring and R24 is hydroxy, amino, methoxy, ethoxy, methylamino, ethylamino, phenylamino or one of the particular values for R6 given above or of the formula NHOR25 in which R25 is hydrogen, methyl, ethyl, phenyl or benzyl, and when R2 contains phenyl, and unless otherwise stated above, the phenyl is optionally substituted by 1 or 2 groups selected from fluorine, chlorine, bromine, hydroxy, amino, carboxy, nitro, carbamoyl, cyano and aminomethyl;

R3 is hydrogen or methoxy;

R4 is hydrogen, methyl, ethyl, n-propyl, isopropyl, 2-fluoroethyl, 2-chloroethyl, 2-hydroxymethyl, 2-methoxyethyl, carboxymethyl, (R) and (S)-1-carboxyethyl, 2-aminoethyl, 2-cyanoethyl, 2-formamidoethyl, allyl, furfuryl, benzyl or 4-pyridylmethyl;

R5 has the meaning stated in claim 1, wherein the optional substituent on one of the ring systems of the formula IV to L, excluding XLII, is one, two or three substituents selected from fluorine, chlorine, bromine, methyl, ethyl, n-propyl, isopropyl, carboxy, methoxycarbonyl, ethoxycarbonyl, methoxycarbonylmethyl, ethoxycarbonylmethyl, methoxy, ethoxy, methylthio, ethylthio, cyano, cyanomethyl, 2-cyanoethyl, amino, methylamino, ethylamino, isopropylamino, dimethylamino, benzylamino, (optionally substituted in the benzene ring by nitro), allylamino, 2-aminoethyl-amino, 2-methoxyethylamino, 2-hydroxyethylamino, hydroxy, mercapto, carbamoyl, methylcarbamoyl, ethylcarbamoyl, dimethylcarbamoyl, phenylthio and heteroarylthio in which the heteroaryl ring is a furan, thiophene, imidazole, thiazole, pyrazole, thiadiazole, pyridine, pyrimidine, pyrazine or pyridazine;

R27 is methyl, ethyl, n-propyl, isopropyl, allyl, methoxymethyl, 2-methoxyethyl, carboxymethyl, 2-carboxyethyl, methoxycarbonylmethyl, 2-methoxycarbonylethyl, carbamoylmethyl, carbamoylethyl, carboxyaminocarbonylmethyl, 2-(carboxyaminocarbonyl)ethyl, methoxycarbonylaminocarbonylmethyl, 2-(methoxycarbonylaminocarbonyl)ethyl, acetylmethyl, propionylmethyl, benzoylmethyl, hydroxymethyl, 2-hydroxyethyl, methylamino, ethylamino, benzyl or 2-phenethyl, or phenyl optionally substituted by 1 or 2 groups selected from fluorine, chlorine, bromine hydroxy, amino, carboxy, nitro, carbamoyl, cyano, trifluoromethyl and aminomethyl;

R26 is hydrogen, methyl, ethyl, n-propyl, isopropyl, phenyl or benzyl;

and the hydrochloride, hydrobromide, phosphate, sulphate, citrate or maleate thereof, and the potassium, magnesium, triethylamine, morpholine, N-methylpiperidine, N-ethylpiperidine, procaine, dibenzylamine or N,N'-dibenzylethylenediamine salts thereof, and other amine salts which have been used with cephalosporins.

19. A cephalosporin derivative as claimed in claims 1 and 18 wherein R1 is 2-aminothiazol-4-yl or 5-amino-1,2,4-thiadiazol-3-yl, R50 is —NOR2 wherein R2 is 1-carboxy-1-methylethyl, 1-carboxyethyl, 1-carboxypropyl, 1-carboxycyclobutyl or 1-carboxycyclopentyl, R3 is hydrogen, X is sulphur, R4 is hydrogen, methyl or ethyl, and R5 is of the formula XVI, XXVIII, XLIII, XLVI, or XLVII,

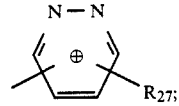 (XVI)

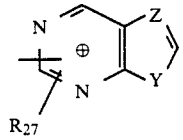 (XXVIII)

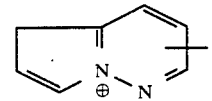 (XLIII)

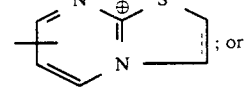 (XLVI)

 (XLVII)

= single or double bond these ring systems being optionally substituted, where possible, on a carbon atom or atoms, by one or two substituents selected from halogen, (1–6C)alkyl, carboxy, (2–6C)alkoxycarbonyl(1–4C)alkyl, (1–6C)alkoxy, (1–6C)alkylthio, amino (1–6C)alkylamino, (2–8C)dialkylamino, benzylamino optionally substituted in the benzene ring thereof by nitro, allylamino, (1–6C)aminoalkylamino, (1–6C)-alkoxy(1–6)alkylamino, (1–6C)hydroxyalkylamino and hydroxy.

20. A cephalosporin derivative selected from the group of compounds listed in the following Table, and the salts thereof with acids and bases which afford pharmaceutically acceptable anions and cations:

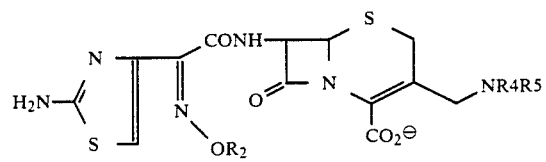

| Example | R2 | R4 | R5 |
|---|---|---|---|
| 60 | —C(CH₃)₂CO₂H | C₂H₅ | 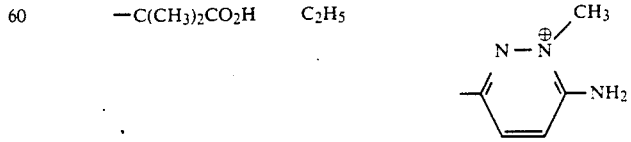 |

-continued

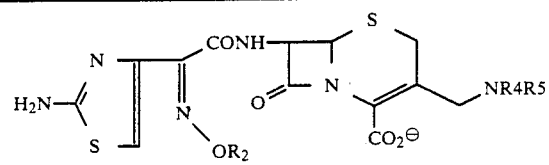

| Example | R2 | R4 | R5 |
|---|---|---|---|
| 81. | —C(CH₃)₂CO₂H | H | (5-methyl-isoquinolinium-N-CH₂CONH₂) |
| 87. | —C(CH₃)₂CO₂H | H | (5-methyl-1-methylquinolinium) |
| 110. | 1-(CO₂H)cyclobutyl | C₂H₅ | (4-methyl-1-methylthieno[2,3-d]pyrimidinium) |
| 111. | 1-(CO₂H)cyclobutyl | C₂H₅ | (methyl-thiazinopyridinium) |
| 177. | 1-(CO₂H)cyclobutyl | C₂H₅ | (3-amino-2-methylpyridazinium, 6-methyl) |
| 178. | 1-(CO₂H)cyclopentyl | H | (3-amino-2-methylpyridazinium, 6-methyl) |
| 184. | 1-(CO₂H)cyclobutyl | C₂H₅ | (thieno-pyridazinium, methyl) |
| 185. | 1-(CO₂H)cyclopentyl | H | (thieno-pyridazinium, methyl) |
| 188. | 1-(CO₂H)cyclopentyl | H | (methyl-thieno-pyridazinium with CH₃) |
| 195. | —C(CH₃)₂CO₂H | H | (3-amino-2-methylpyridazinium) |

-continued

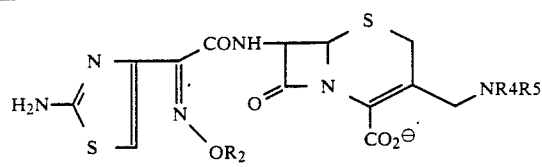

| Example | R2 | R4 | R5 |
|---|---|---|---|
| 202. | cyclobutyl-CO₂H | H | (N=C-S fused ring with N⊕) |
| 209. | —CH(C₂H₅)CO₂H (m.p. isomer) | H | (N=N⊕-CH₃ pyridazinium with CH₃) |
| 218. | cyclopentyl-CO₂H | H | (N=N⊕-CH₃ pyridazinium with CH₃) |
| 219. | —CH(CH₃)CO₂H (m.p. isomer) | H | (thieno[2,3-d]pyrimidinium, N⊕-CH₃) |
| 225. | —C(CH₃)₂CO₂H | C₂H₅ | (thieno[2,3-d]pyrimidinium, N⊕-CH₃) |
| 226. | —C(CH₃)₂CO₂H | C₂H₅ | (thieno[2,3-d]pyrimidinium, N⊕-CH₂CH:CH₂) |
| 232. | —C(CH₃)₂CO₂H | C₂H₅ | (pyrazolo-pyridazinium, N⊕-CH₃) |
| 249. | —C(CH₃)₂CO₂H | C₂H₅ | (N=C-S fused ring with N⊕) |
| 251. | —C(CH₃)₂CO₂H | C₂H₅ | (N=C-S fused ring with N⊕, ethyl) |

-continued
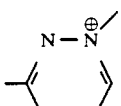
| Example | R2 | R4 | R5 |
|---|---|---|---|
| 261 | —CH($C_2H_5$)$CO_2H$ (m.p. isomer) | $C_2H_5$ | 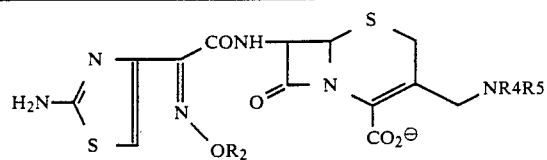 |
* * * * *